(12) United States Patent
Andrieux et al.

(10) Patent No.: US 11,613,753 B2
(45) Date of Patent: Mar. 28, 2023

(54) METHODS AND PHARMACEUTICAL COMPOSITIONS FOR TREATING TUBULIN CARBOXYPEPTIDASES ASSOCIATED DISEASES

(71) Applicants: LES LABORATOIRES SERVIER, Suresnes (FR); INSERM (INSTITUT NATIONAL DE LA SANTE ET DE LA RECHERCHE MEDICALE), Paris (FR); UNIVERSITE GRENOBLE ALPES, Saint Martin d'Hères (FR); COMMISSARIAT A L'ENERGIE ATOMIQUE ET AUX ENERGIES ALTERNATIVES, Paris (FR)

(72) Inventors: Annie Andrieux, Grenoble (FR); Marie-José Moutin, Eybens (FR); Christophe Bosc, Grenoble (FR); Chrystelle Aillaud, Romans sur Isère (FR); Leticia Peris, Moirans (FR); Philippe Delagrange, Issy les Moulineaux (FR)

(73) Assignees: LES LABORATOIRES SERVIER, Suresnes (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 156 days.

(21) Appl. No.: 16/758,104

(22) PCT Filed: Oct. 26, 2018

(86) PCT No.: PCT/EP2018/079448
§ 371 (c)(1),
(2) Date: Apr. 22, 2020

(87) PCT Pub. No.: WO2019/081730
PCT Pub. Date: May 2, 2019

(65) Prior Publication Data
US 2020/0407726 A1 Dec. 31, 2020

(30) Foreign Application Priority Data
Oct. 26, 2017 (EP) ..................................... 17306476

(51) Int. Cl.
*A61P 25/28* (2006.01)
*C12N 15/113* (2010.01)
*C12Q 1/37* (2006.01)

(52) U.S. Cl.
CPC .......... *C12N 15/1137* (2013.01); *A61P 25/28* (2018.01); *C12Q 1/37* (2013.01); *C12N 2310/14* (2013.01); *G01N 2333/948* (2013.01)

(58) Field of Classification Search
CPC ....................................................... A61P 21/00
See application file for complete search history.

(56) References Cited

U.S. PATENT DOCUMENTS

2016/0009790 A1   1/2016   Sato

OTHER PUBLICATIONS

Affara, Muna, et al., "Vasohibin-1 is identified as a master-regulator of endothelial cell apoptosis using gene network analysis", BMC Genomics, 14:23, 2013, pp. 1-12.
Aillaud, Chrystell, et al., "Vasohibins/SVBP are tubulin carboxypeptidases (TCPs) that regulate neuron differentiation", Science. 358, 2017, pp. 1448-1453.
Barisic, Marin, et al., "The tubulin code: a navigation system for chromosomes during mitosis", Trends in Cell Biology, vol. 26, No. 10, Oct. 2016, pp. 766-775.
Fonrose, Xavier, et al., "Parthenolide inhibits tubulin carboxypeptidase activity", Cancer Res, 67:(7), 2007, Apr. 1, 2007. pp. 3371-3378.
Fukumitsu, Ryu, et al., "Expression of vasohibin-1 in human carotid atherosclerotic plaque", Journal of Atherosclerosis and Thrombosis, vol. 22, No. 9, 2015, pp. 942-948.
International Search Report for PCT/EP2018/079448 dated Mar. 11, 2019.
Neiuwenhuis, Joppe, et al., "Vasohibins encode tubulin detyrosinating activity", Science, 358, 2017, pp. 1453-1456.
Suzuki, Yasuhiro, et al., "Isolation of a small vasohibin-binding protein (SVBP) and its role in vasohibin secretion", Journal of Cell Science, 123, 2010, pp. 3094-3101.

*Primary Examiner* — Tekchand Saidha
(74) *Attorney, Agent, or Firm* — Hueschen and Sage

(57) ABSTRACT

Using chemical proteomics with a potent unique irreversible inhibitor, inventors found that major brain tubulin carboxypeptidase (TCP) is a complex of vasohibin-1 (VASH1) with the Small Vasohibin-Binding Protein (SVBP). VASH1 and its homologue vasohibin-2 (VASH2), when complexed with SVBP, exhibit robust and specific Tyr/Phe carboxypeptidase activity on microtubules. Accordingly inventors are the first to identify the enzymatic activity of vasohibin and vasohibin/SVBP complex. Knock down of vasohibins or SVBP in cultured neurons results in a marked reduction of tyrosinated α-tubulin levels and onset of severe differentiation defects. Furthermore, knock down of vasohibins disrupts neuronal migration in developing mouse neocortex. These results establish vasohibin/SVBP complexes as TCP enzymes. Accordingly, the present invention relates methods and pharmaceutical compositions for treating tubulin carboxypeptidases (TCP) associated diseases such as neurological disorders and cardiovascular diseases with an inhibitor of activity or expression of Vasohibin or Vasohibin/SVBP complex.

2 Claims, 27 Drawing Sheets
Specification includes a Sequence Listing.

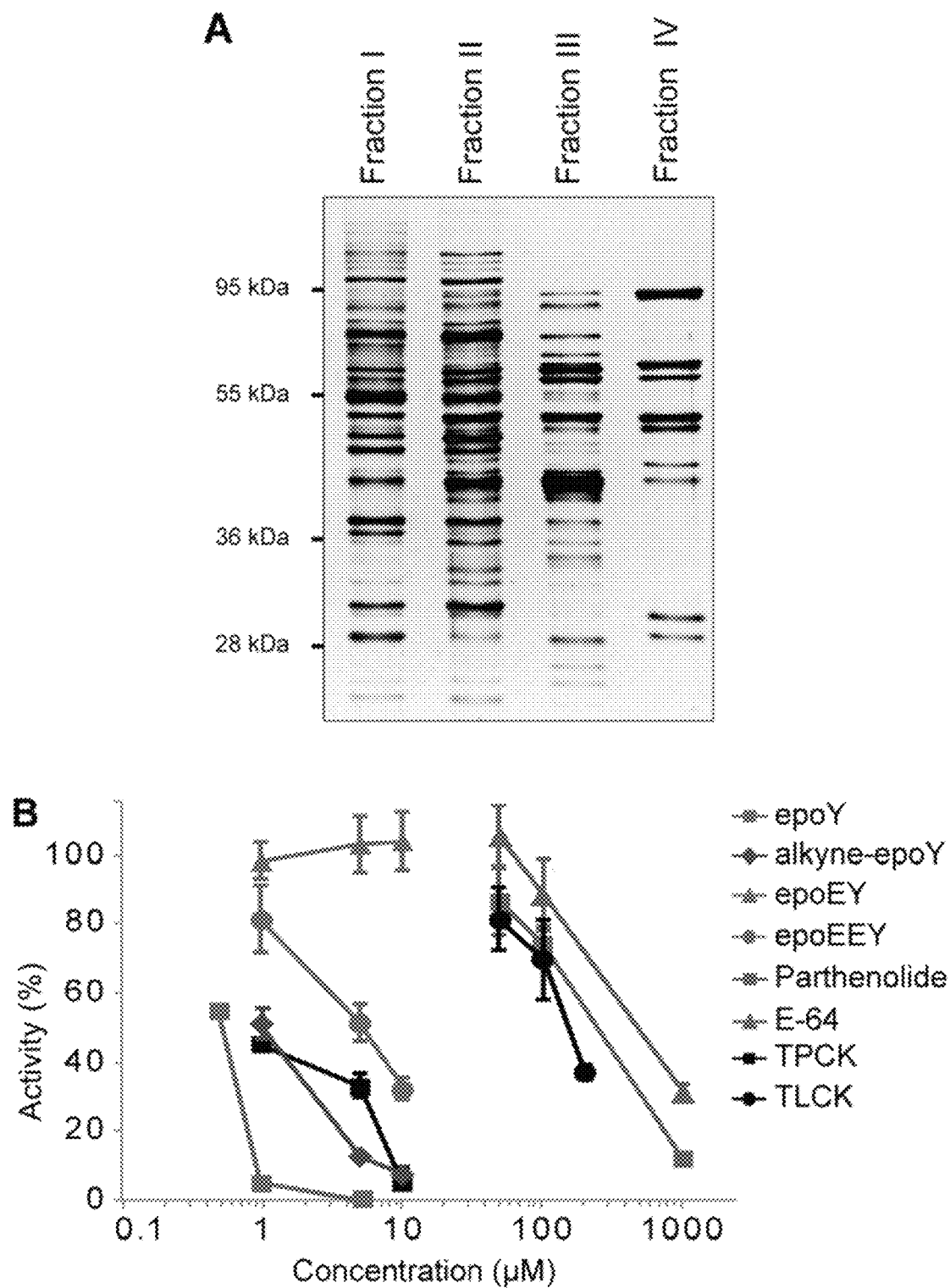
Figure 1 A and B

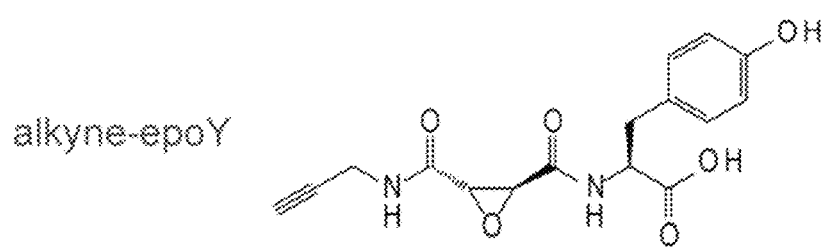
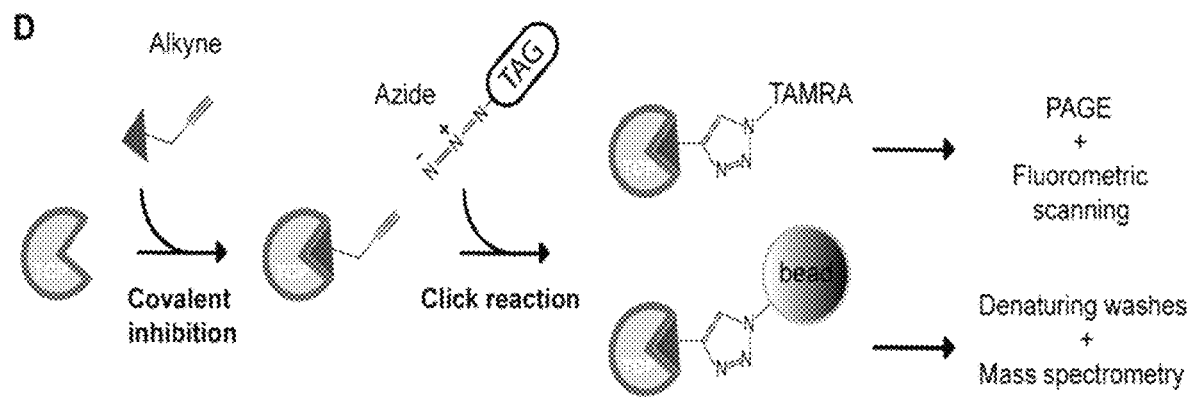
Figure 1 C and D

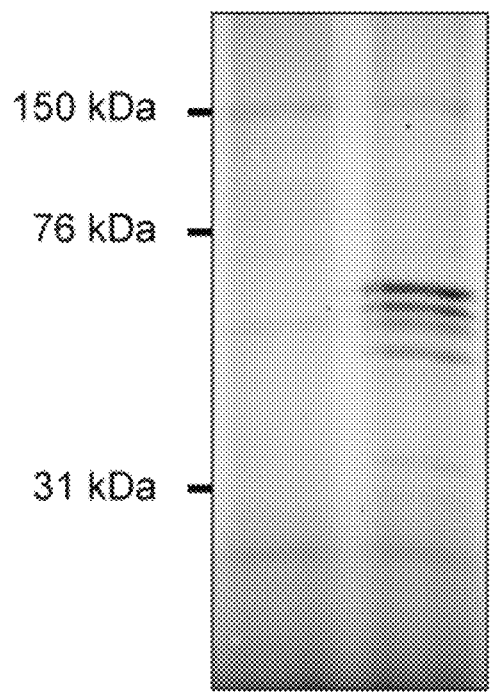
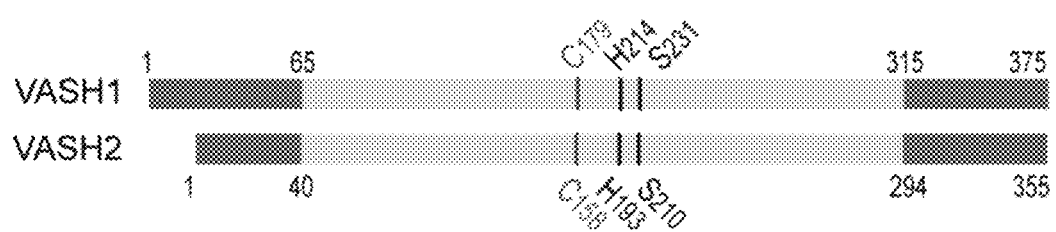
Figure 1 E and F

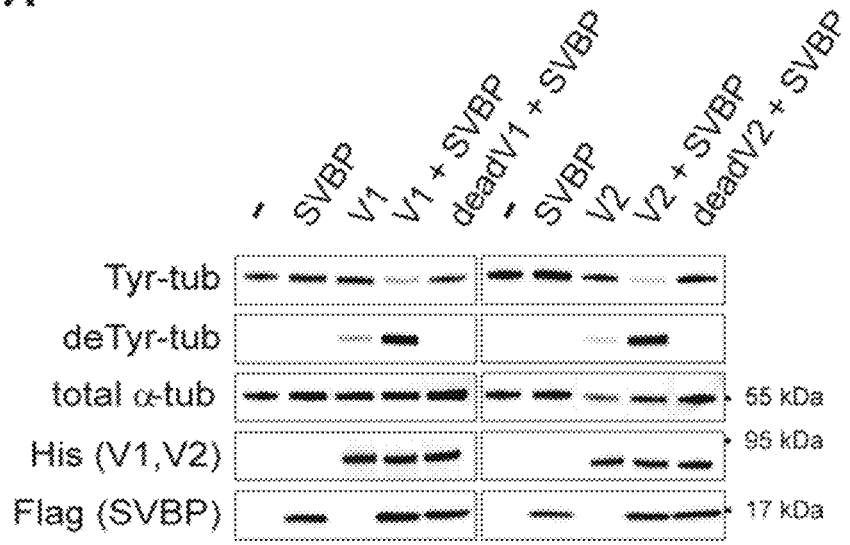
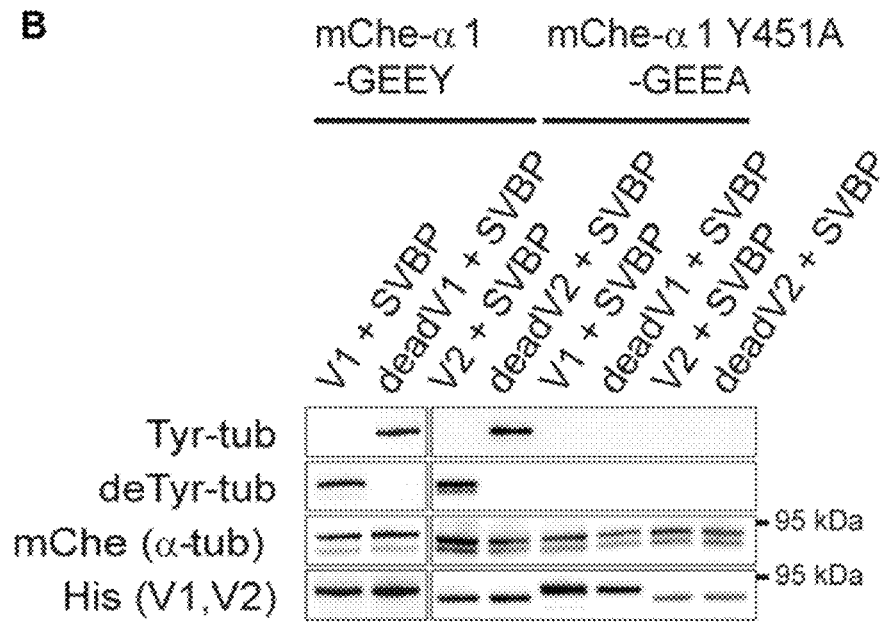
Figure 2A and B

Figure 2:
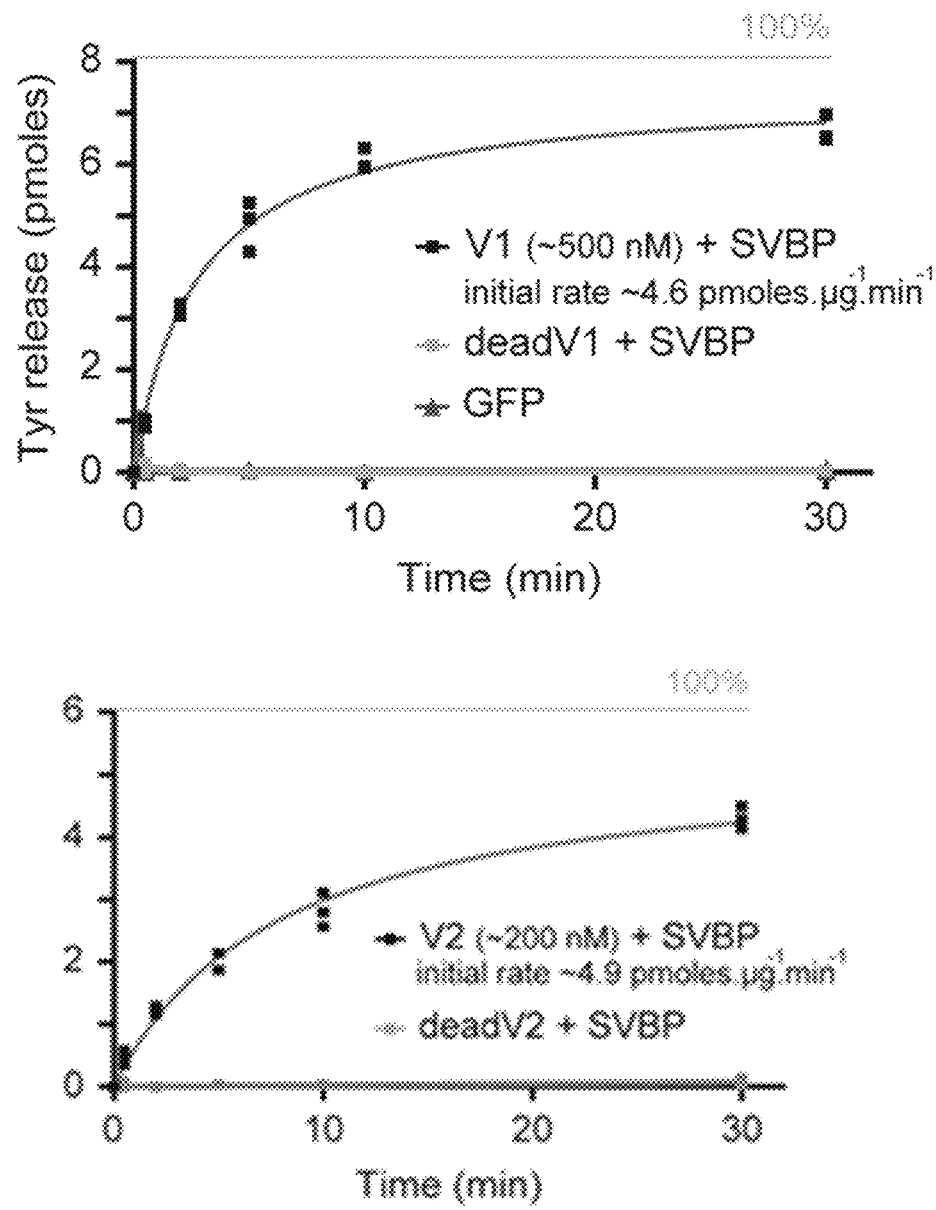

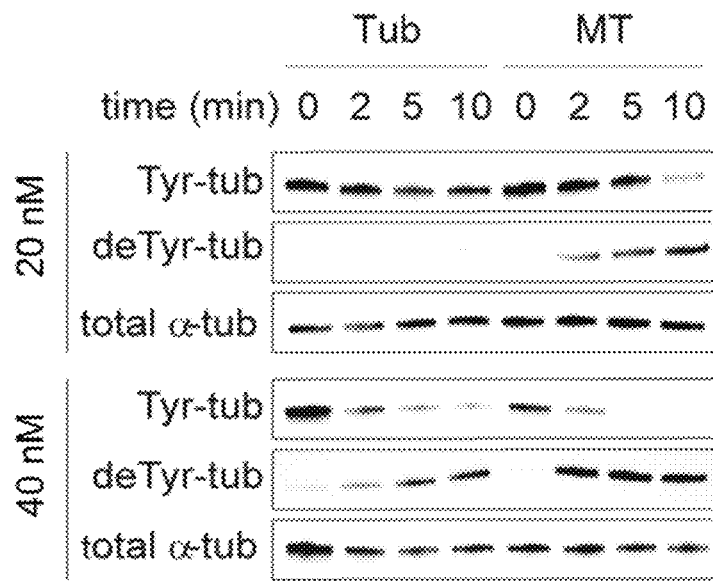
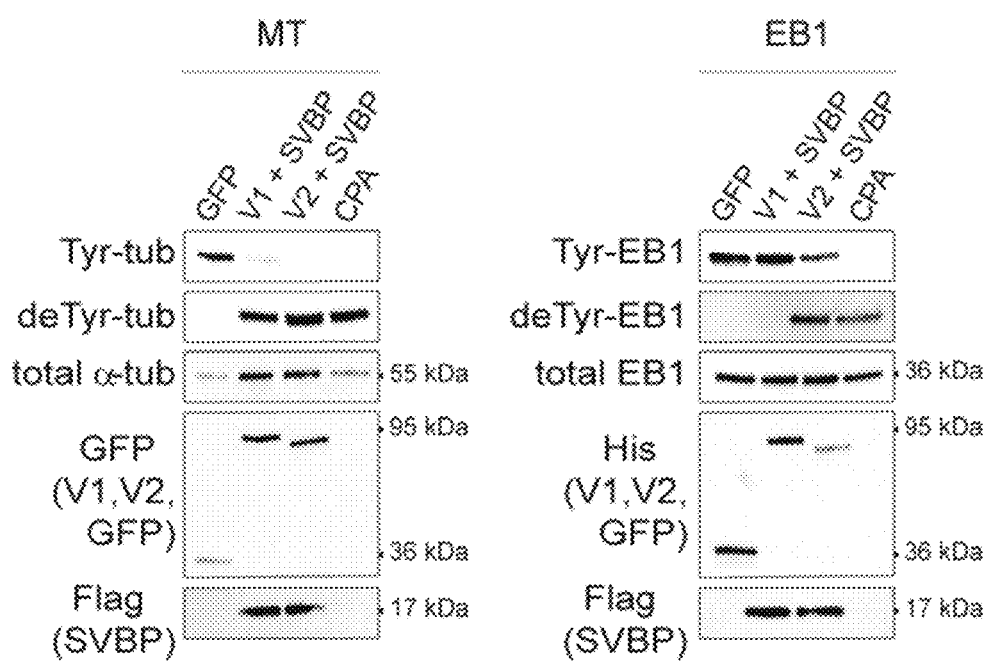
Figure 2 D and E

Figure 3:
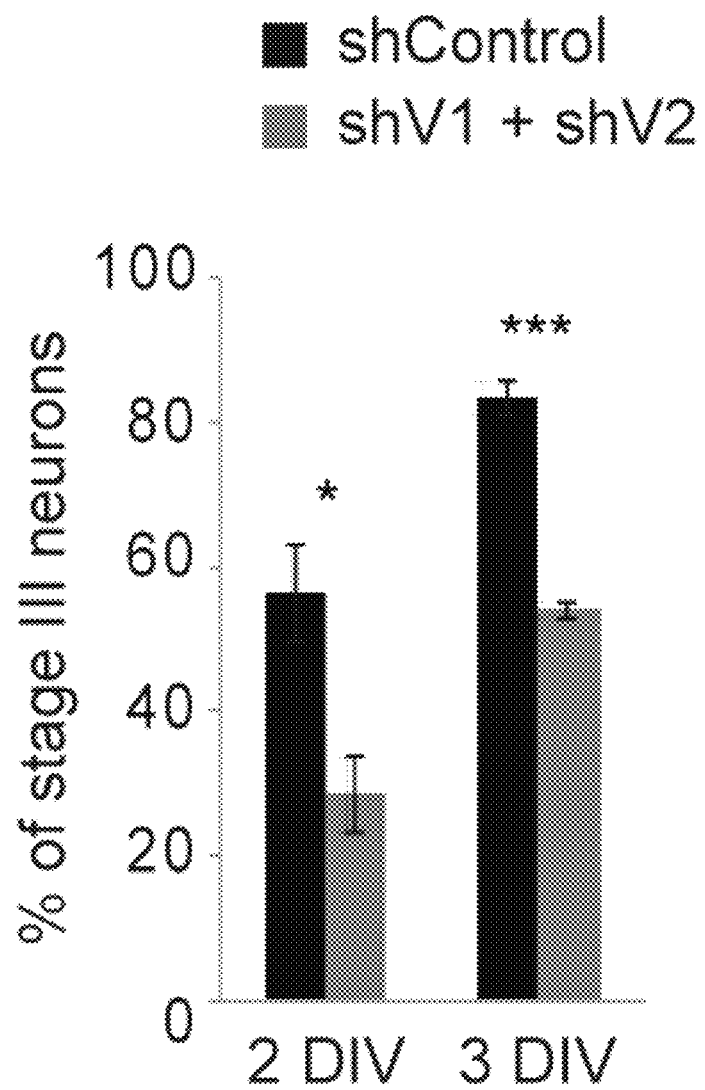

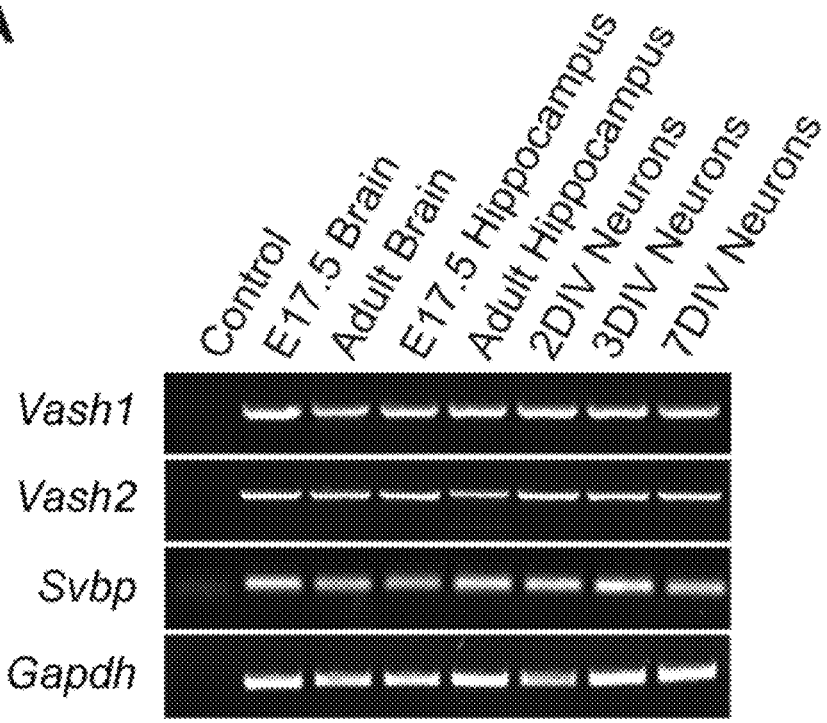
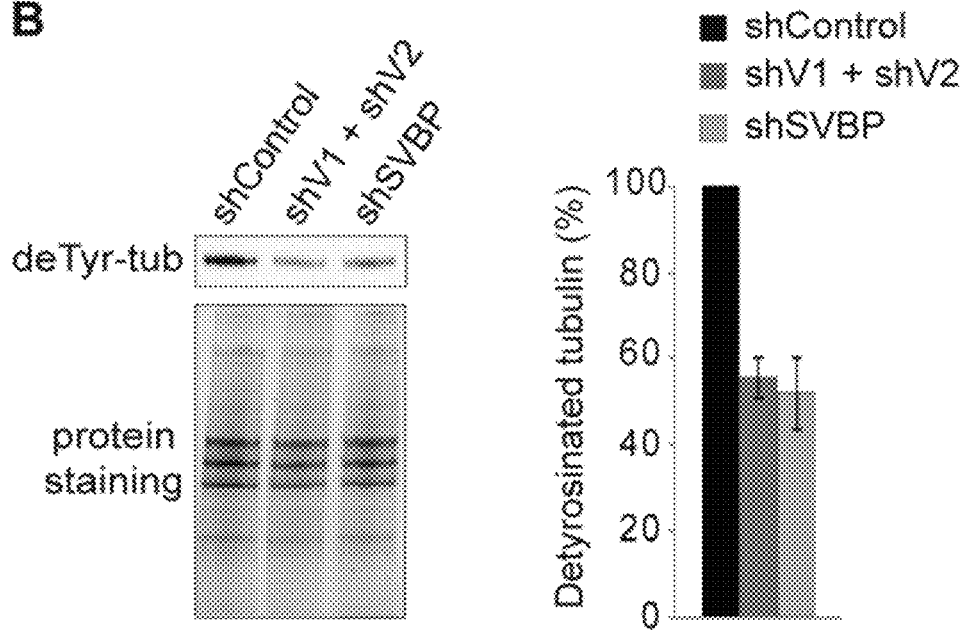
Figure 3 A and B

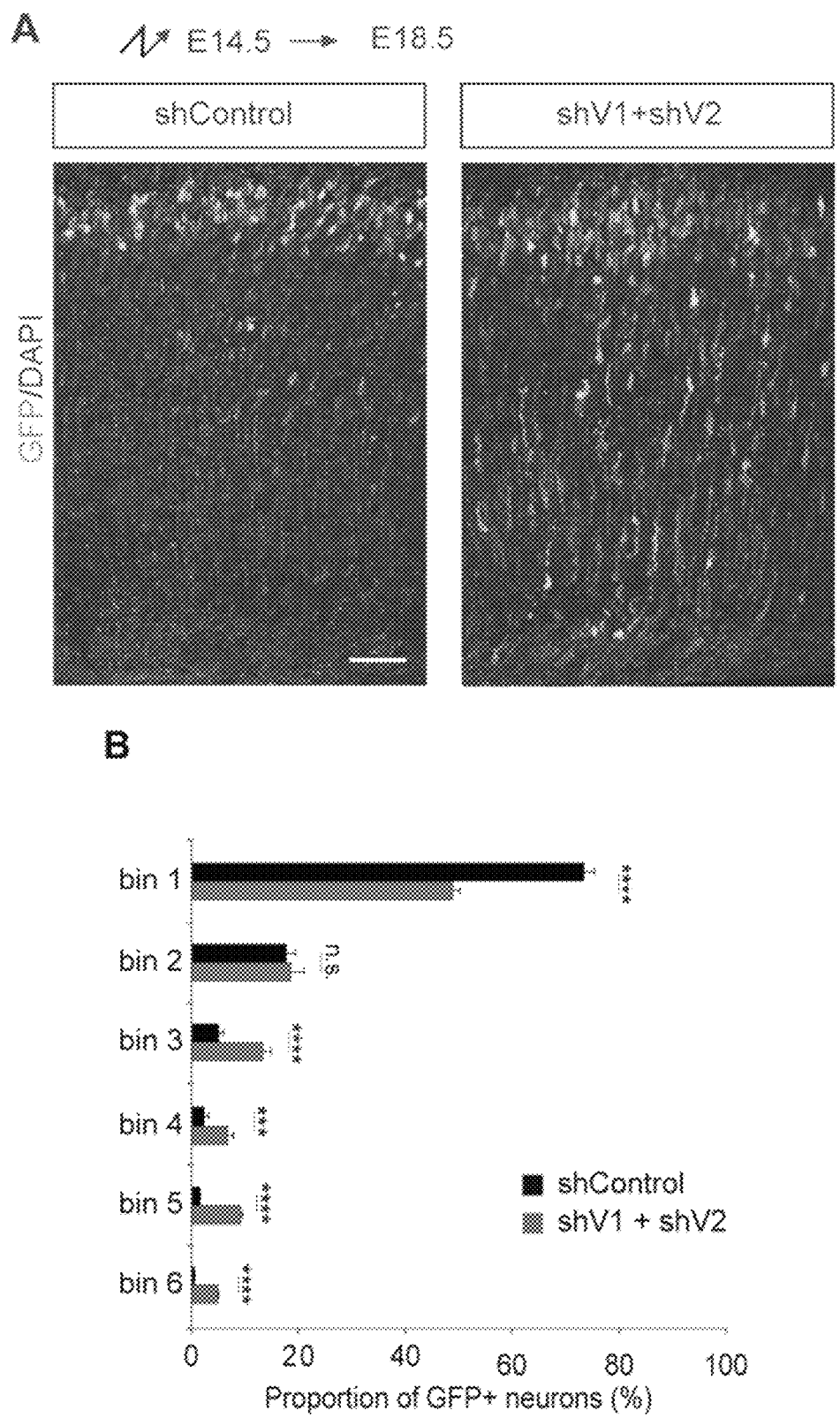
Figure 4 A and B

B

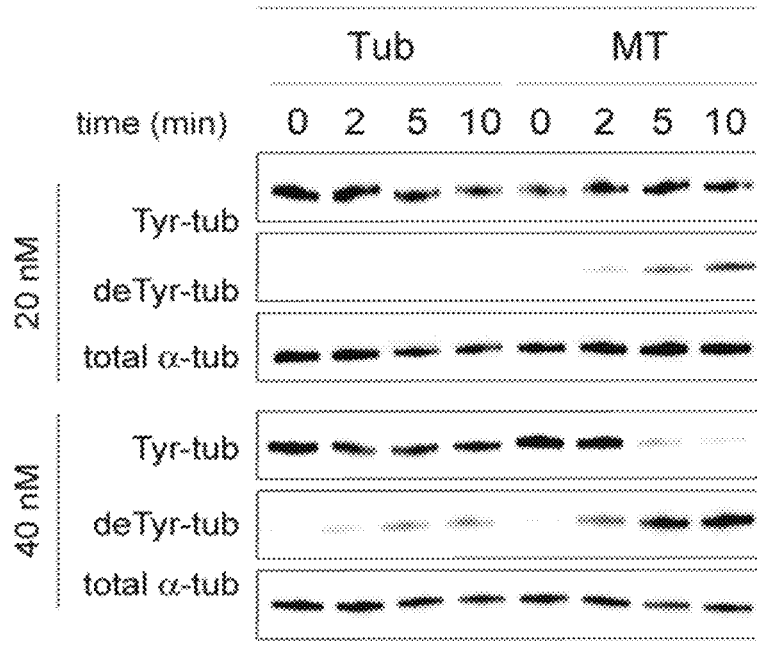
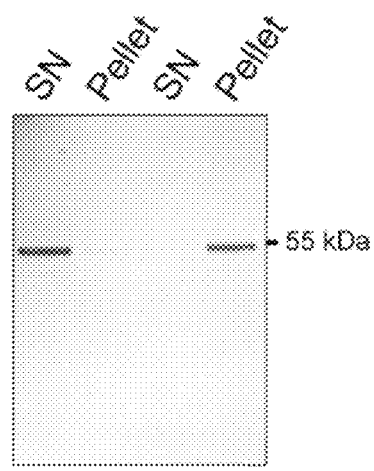
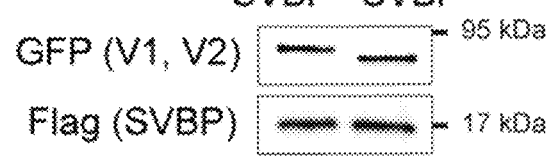
Figure 6 B, C and D

SEQUENCE LISTING

<160> NUMBER OF SEQ ID NOS: 16

<210> SEQ ID NO 1
<211> LENGTH: 29
<212> TYPE: DNA
<213> ORGANISM: Artificial Sequence
<220> FEATURE:
<223> OTHER INFORMATION: shRNA mouse Vasohibin-1

<400> SEQUENCE: 1
ccgagacatg cggctcaaga ttggcaagg                                29

<210> SEQ ID NO 2
<211> LENGTH: 29
<212> TYPE: DNA
<213> ORGANISM: Artificial Sequence
<220> FEATURE:
<223> OTHER INFORMATION: shRNA mouse Vasohibin-2

<400> SEQUENCE: 2
agacaaatcg cctgctctga ccgagaaga                                29

<210> SEQ ID NO 3
<211> LENGTH: 29
<212> TYPE: DNA
<213> ORGANISM: Artificial Sequence
<220> FEATURE:
<223> OTHER INFORMATION: shRNA mouse SVBP

<400> SEQUENCE: 3
agagtggaga aggctaagca gaaatctgc                                29

<210> SEQ ID NO 4
<211> LENGTH: 19
<212> TYPE: DNA
<213> ORGANISM: Artificial Sequence
<220> FEATURE:
<223> OTHER INFORMATION: RT-PCR primer for Vasohibin-1 - forward
      sequence

<400> SEQUENCE: 4
tacaaaccgc ccgccttcc                                           19

<210> SEQ ID NO 5
<211> LENGTH: 23
<212> TYPE: DNA
<213> ORGANISM: Artificial Sequence
<220> FEATURE:
<223> OTHER INFORMATION: RT-PCR primer for Vasohibin-1 - reverse
      sequence

<400> SEQUENCE: 5
acagaccctg acagctacca aca                                      23

<210> SEQ ID NO 6
<211> LENGTH: 20
<212> TYPE: DNA
<213> ORGANISM: Artificial Sequence
<220> FEATURE:
<223> OTHER INFORMATION: RT-PCR primer for Vasohibin-2 - forward
      sequence

<400> SEQUENCE: 6
gcagccttcc attgagcggt                                          20

```
<210> SEQ ID NO 7
<211> LENGTH: 21
<212> TYPE: DNA
<213> ORGANISM: Artificial Sequence
<220> FEATURE:
<223> OTHER INFORMATION: RT-PCR primer for Vasohibin-2 - reverse
      sequence

<400> SEQUENCE: 7
cagtcaaccc agggctttgc c                                              21

<210> SEQ ID NO 8
<211> LENGTH: 22
<212> TYPE: DNA
<213> ORGANISM: Artificial Sequence
<220> FEATURE:
<223> OTHER INFORMATION: RT-PCR primer for SVBP - forward sequence

<400> SEQUENCE: 8
ccagcaggag ctgaagcaaa ga                                             22

<210> SEQ ID NO 9
<211> LENGTH: 20
<212> TYPE: DNA
<213> ORGANISM: Artificial Sequence
<220> FEATURE:
<223> OTHER INFORMATION: RT-PCR primer for SVBP - reverse sequence

<400> SEQUENCE: 9
gcaccagttc ctctgccggg                                                20

<210> SEQ ID NO 10
<211> LENGTH: 21
<212> TYPE: DNA
<213> ORGANISM: Artificial Sequence
<220> FEATURE:
<223> OTHER INFORMATION: RT-PCR primer for GAPDH - forward sequence

<400> SEQUENCE: 10
tcaacgggaa gcccatcacc a                                              21

<210> SEQ ID NO 11
<211> LENGTH: 20
<212> TYPE: DNA
<213> ORGANISM: Artificial Sequence
<220> FEATURE:
<223> OTHER INFORMATION: RT-PCR primer for GAPDH - reverse sequence

<400> SEQUENCE: 11
gtttctccag gcggcacgtc                                                20

<210> SEQ ID NO 12
<211> LENGTH: 14
<212> TYPE: PRT
<213> ORGANISM: Artificial Sequence
<220> FEATURE:
<223> OTHER INFORMATION: substrate of TTL enzyme or the product of
      reaction of TCP
<220> FEATURE:
<221> NAME/KEY: MISC_FEATURE
<222> LOCATION: (1)..(1)
<223> OTHER INFORMATION: Biotin attached

<400> SEQUENCE: 12

Val Asp Ser Val Glu Gly Glu Gly Glu Glu Glu Asp Glu Glu
1               5                   10
```

```
<210> SEQ ID NO 13
<211> LENGTH: 15
<212> TYPE: PRT
<213> ORGANISM: Artificial Sequence
<220> FEATURE:
<223> OTHER INFORMATION: product of reaction with TTL or the substrate
      of TCP
<220> FEATURE:
<221> NAME/KEY: MISC_FEATURE
<222> LOCATION: (1)..(1)
<223> OTHER INFORMATION: Biotin attached

<400> SEQUENCE: 13

Val Asp Ser Val Glu Gly Glu Gly Glu Glu Glu Asp Glu Glu Tyr
1               5                   10                  15

<210> SEQ ID NO 14
<211> LENGTH: 15
<212> TYPE: PRT
<213> ORGANISM: Homo sapiens
<220> FEATURE:
<223> OTHER INFORMATION: C-terminal peptide of alpha tubulin

<400> SEQUENCE: 14

Val Asp Ser Val Glu Gly Glu Gly Glu Glu Glu Gly Glu Glu Tyr
1               5                   10                  15

<210> SEQ ID NO 15
<211> LENGTH: 4
<212> TYPE: PRT
<213> ORGANISM: Artificial Sequence
<220> FEATURE:
<223> OTHER INFORMATION: peptide sequence

<400> SEQUENCE: 15

Gln Glu Glu Tyr
1

<210> SEQ ID NO 16
<211> LENGTH: 4
<212> TYPE: PRT
<213> ORGANISM: Artificial Sequence
<220> FEATURE:
<223> OTHER INFORMATION: peptide sequence

<400> SEQUENCE: 16

Gly Glu Glu Tyr
1
```

METHODS AND PHARMACEUTICAL COMPOSITIONS FOR TREATING TUBULIN CARBOXYPEPTIDASES ASSOCIATED DISEASES

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3.414 Bytes ASCII (Text) file named "SEQUENCE_LISTING.TXT," created on 28 Jul. 2020.

FIELD OF THE INVENTION

The present invention relates to methods and pharmaceutical compositions for treating tubulin carboxypeptidases (TCP) associated diseases such as neurological disorders and cardiovascular diseases with an inhibitor of activity or expression of Vasohibin or of Vasohibin/SVBP (Small Vasohibin Binding Protein) complex.

BACKGROUND OF THE INVENTION

Microtubules are cytoskeletal polymers of $\alpha/\beta$ tubulin dimers centrally involved in cell division, motility and morphogenesis. In the detyrosination/tyrosination cycle of tubulin, the C-terminal tyrosine of $\alpha$-tubulin is removed by an elusive peptidase (TCP) and re-added by the tubulin tyrosine ligase (TTL, for review see (Barra et al. (1988), Mol Neurobiol, 2:133). This cycle, which is unique to tubulin and mostly conserved among evolution from chordate to mammals, has a vital role in vivo (Erck et al. (2005), Proc Natl Acad Sci USA, 102:7853). Tubulin de/tyrosination of $\alpha$-tubulin is an important regulatory signal for mitosis (Badin-Larcon et al. (2004), Proc Natl Acad Sci USA, 101:5577; Barisic and Maiato (2016). Trends Cell Biol; Barisic et al. (2015), Science, 348:799; Barisic and Maiato, 2016; Barisic et al., 2015; Gobrecht et al. (2016), Journal of Neuroscience 36.14: 3890-3902; Konishi and Setou (2009), Nat Neurosci, 12:559; Marcos et al. (2009), PloS one, 4:e5405; Peris et al. (2006), J Cell Biol, 174:839-849), for neuronal physiology (P. Gobrecht et al., (2016) J Neurosci 36, 3890: Y. Konishi, N. Setou, (2009) Nat Neurosci 12, 559; S. Marcos et al., (2009) PloS one 4, e5405), and for muscle mechanotransduction (Kerr et al. (2015) Nature communications, 6:8526; Robison et al. (2016), Science, 352:aaf0659). Consequently, abnormal tyrosination levels are associated with cell transformation and tumor aggressiveness (Lafanecher et al. (1998), J Cell Sci, 111 (Pt 2):171; Whipple et al. (2007), Exp Cell Res, 313:1326), neuronal disorganization (Erck et al. (2005), Proc Natl Acad Sci USA, 102; 7853; Peris et al. (2006). J Cell Biol. 174:839; Peris et at (2009), J Cell Biol. 185:1159), and heart failure and cardiomyopathies (Robison et al. (2016), Science, 352:aaf0659 and S. Belmadani, C. Pous, R. Ventura-Clapier, R. Fischmeister, P. F. Mery, (2002) Molecular and cellular biochemistry 237, 39). Although the detyrosination reaction was first described 40 years ago (M. E. Hallak, J. A. Rodriguez, H. S. Barra, R. Caputto, (1977) FEBS Lett 73, 147), the identity of TCP remained unknown, and a complete understanding of the cycle is therefore still lacking.

Accordingly, there is a need to identify the nature of the TCP enzymes in order to modulate its activity in pathological condition.

SUMMARY OF THE INVENTION

Here, inventors successfully identified Vasohibin/SVBP complexes as TCP enzymes and studied the impact of their down-regulation on neuron physiology.

Accordingly the present invention relates to an inhibitor of Vasohibin or of Vasohibin/SVBP complex activity or expression for use in a method for treating tubulin carboxypeptidases (TCP) associated diseases such as cardiovascular and neurological disorders in a subject in need thereof.

The present invention also relates to a method for screening a plurality of candidate compounds useful for treating tubulin carboxypeptidases (TCP) associated diseases comprising the steps consisting of (a) testing each of the candidate compounds for its ability to inhibit vasohibin or vasohibin/SVBP complex activity or expression and (b) and positively selecting the candidate compounds capable of inhibiting said vasohibin/SVBP complex activity or expression.

DETAILED DESCRIPTION OF THE INVENTION

Reversible detyrosination of $\alpha$-tubulin is crucial to microtubule dynamics and functions and its defect has been implicated in cancer, brain disorganization and cardiomyopathies. The identification of the tubulin tyrosine carboxypeptidase (TCP) in charge of detyrosination remained however unsuccessful. Here, using chemical proteomics with a potent unique irreversible inhibitor, inventors found that major brain TCP is a complex of vasohibin-1 (VASH1) with the Small Vasohibin Binding Protein (SVBP). VASH1 and its homologue vasohibin-2 (VASH2), when complexed with SVBP, exhibit robust and specific Tyr/Phe carboxypeptidase activity on microtubules. Accordingly inventors are the first to demonstrate the enzymatic activity of vasohibin and vasohibin/SVBP complex. Knock down of vasohibins or SVBP in cultured neurons results in a marked reduction of tyrosinated $\alpha$-tubulin levels and onset of severe differentiation defects. Furthermore, knock down of vasohibins disrupts neuronal migration in developing mouse neocortex. These results establish vasohibin/SVBP complexes as TCP enzymes.

Accordingly, the present invention relates to an inhibitor of Vasohibin/SVBP complex activity or expression for use in a method for treating tubulin carboxypeptidases (TCP) associated diseases in a subject in need thereof.

As used herein, the term "tubulin carboxypeptidases (TCP) associated diseases" refers to a group of diseases associated with a disorganization of detyrosination/tyrosination cycle of tubulin. Examples of pathologies involving the tubulin carboxypeptidases (TCP) include neurological disorders and cardiovascular diseases.

TTL enzyme and controlled amount of tyrosinated tubulin are vital for neuronal organization (Erck et al. (2005), Proc Natl Acad Sci USA, 102:7853). TTL expression is reduced in human aged brains (Loerch et al. (2008), PloS one, 3:e3329) as well as in Alzheimer's disease patients brains (unpublished data). These deficiencies in an animal model of Alzheimer have been shown to be simultaneous to impaired synaptic plasticity and cognitive abilities (unpublished results from Andrieux lab). Accordingly use of TCP inhibitors should re-establish physiological amount of tyrosinated/detyrosinated tubulin in brain and either restore or prevent further decline in cognitive abilities associated to diseases (cognitive abilities refers as skills needed to carry out any task from the simplest to the most complex: learning, memory, problem-solving, decision making, etc. . . . ).

Moreover, recent studies show that reducing microtubule detyrosination promotes nerve regeneration (Gobrecht et al. (2016), The Journal of neuroscience: the official journal of the Society for Neuroscience, 36:3890), and that increase in tyrosinated alpha-tubulin in injured axons is required for retrograde injury signaling and axon regeneration (Song et al. 2015). Targeting microtubule dynamics modifies the composition of the inhibitory environment formed by scar tissue and renders it more permissive for regenerating axons. Microtubules have a dual function in axon regeneration. Besides their role in supporting axon growth they provide the transport roads for retrograde signals back to the nucleus (Blanquie and Bradke, 2018).

Accordingly in a specific embodiment, TCP associated-diseases include neurological disorders such as neurodegenerative diseases.

The term "neurological disorder" as used herein is defined as disease, disorder or condition which directly or indirectly affects the normal functioning or anatomy of a subject's nervous system.

In the context of the invention the term "neurodegenerative disorder" is defined as disease in which cells of the central or peripheral nervous system are affected or lost.

A particularly preferred neurodegenerative disorder is Alzheimer's disease (AD). It is well documented that microtubules are key players in the pathology of Alzheimer's disease (Matsuyama and Jarvik, 1989; Dent, 2016; Brandt and Bakota, 2017). Recent results show that TTL expression is decreased in Alzheimer's disease patient brains (unpublished data), whereas detyrosinated tubulin is increased (as demonstrated in the Examples below). Moreover, the beta-amyloid-induced neurotoxicity is prevented in primary neuronal cultures from transgenic mice deleted for Vasohibin1 or SVBP protein (results also presented below). Microtubules are one of the three cytoskeletal components and are crucial to maintain axonal integrity and form the tracks for axonal transport (Eira et al, 2016). Axonal transport defects are a direct cause of neurodegenerative disease. Reversible detyrosination of α-tubulin is crucial to microtubule dynamics and functions, such as axonal transport, and in dendritic spines; the postsynaptic compartment of excitatory neurons in the CNS (Dent, 2016). Modifications of microtubule dynamics have been observed in several neurodegenerative diseases such as Alzheimer's disease, Parkinson's disease. Amyotrophic Lateral Sclerosis, and tauopathies like Progressive Supranuclear Palsy (Baird and Benneth, 2013; Dubey et al, 2015; Cartelli and Cappelletti, 2017). Recent studies also suggest that MT dynamics in the adult brain function in the essential process of learning and memory and may be compromised in degenerative diseases (Dent et al., 2016).

There is also evidence of synaptic and axonal dysfunction and neurite dystrophy preceding neuronal loss in Huntington's disease patients (Li and Conforti, 2013).

Microtubules and/or tubulin have also been reported to be disorganized in models of ischemia (stroke) either in vitro or in vivo (Ma et al, 2010; Psilodimitrakopoulos et al, 2013). In multiple sclerosis (MS) and associated models such as experimental autoimmune encephalomyelitis alterations in axonal transport have been shown to exist before neurodegeneration occurs (Van den Berg et al, 2017). The chemical environment associated with neuroinflammation is in itself already capable of disrupting microtubule-associated axonal transport (Van den Berg et al, 2017).

Preferably, the neurological or neurodegenerative disorder is selected form the group consisting of multiple sclerosis, stroke, amyotrophic lateral sclerosis, Parkinson disease. Huntington disease Alzheimer's disease.

Other examples for neurological disorders are also traumatic brain injury, spinal cord injury, intracranial lesions or intravertebral lesions including, but not limited to, contusion, penetration, shear, compression or laceration lesions of the spinal cord or whiplash shaken infant syndrome.

In a preferred embodiment, the neurodegenerative disorder is Alzheimer disease.

in another preferred embodiment, the neurological disorder is stroke.

The present invention also relates to an inhibitor of Vasohibin/SVBP complex activity or expression for use as neuroprotective or neurotropic agent.

Control of tyrosinated detyrosinated tubulin in microtubules is also involved in viscoelastic resistance to sarcomere shortening and stretch in cardiomyocytes and thus, in cardiac contractility (Kerr et al. (2015) Nature Comm., 6:8526; Robison et al. (2016) Science, 352:aaf0659; Chen et al. (2018) Nature Med., 24:1225). Clinical data showed that level of cardiac detyrosinated tubulin is negatively correlated with left ventricular ejection fraction in control subjects and hypertrophic cardiomyopathy patients (Robison et al. (2016) Science, 352:aaf0659). Thus, a TCP inhibitor could be also used in the treatment of hypertrophic cardiomyopathy, post ischemic cardiomyopathy, dilated cardiomyopathy (Robison et al. (2016) Science, 352:aaf0659; Chen et al. (2018) Nature Med., 24:1225), dystrophinopathy (Belanto et al. (2016)).

In a specific embodiment the TCP inhibitor is used in the treatment of Heart failure, particularly of Heart failure with reduced Ejection Fraction (ischemic, non-ischemic) and Heart Failure with preserved Ejection Fraction (hypertrophic cardiomyopathies, diabetic cardiomyopathies).

In a specific embodiment TCP associated diseases is cardiovascular disease selected from the list consisting myocardial infarction, myocardial infarction induced cardiovascular dysfunction, heart failure, cardiomyopathy and dystrophinopathy.

In a preferred embodiment cardiovascular disease is Heart Failure with reduced Ejection Fraction (ischemic, non-ischemic).

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a subject, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

The terms "subject," and "patient," used interchangeably herein, refer to a mammal, particularly a human who has been previously diagnosed with tubulin carboxypeptidases (TCP) associated diseases such as cardiovascular and neurological disorders or who is at risk for having or developing tubulin carboxypeptidases (TCP) associated diseases such as cardiovascular and neurological disorders. Typically, a diagnosis of neurological disorders such as neurodegenerative disease may be made after brain biopsy or by using neuro-imagery proceeding (IRM, PetScan, . . . ) or with biological markers associated with the disease.

As used herein the term 'or "Vasohibin" has its general meaning in the art and is composed of Vasohibin-1 or Vasohibin-2 proteins.

As used herein the term 'or "Vasohibin/SVBP complex" has its general meaning in the art. Vasohibin/SVBP complex is composed of Vasohibin-1 or Vasohibin-2, and SVBP (Small Vasohibin Binding Protein).

Vasohibin 1 is selectively induced in endothelial cells by pro-angiogenic stimulatory growth factors such as VEGF: it appears to operate as an intrinsic and highly specific feedback inhibitor of activated endothelial cells engaged in the process of angiogenesis. Whereas vasohibin 1 mRNA and protein are induced by VEGF in a time and concentration dependent manner, the secreted protein antagonizes the angiogenic effects of VEGF (Watanabe, K. et al. (2004) J. Clin. Invest. 114:898). Vasohibin-2, encoded by a distinct gene producing thirteen splice variants finally encoding nine isoforms (Shibuya, T. et al. (2006) Arterioscler. Thromb. Vasc. Biol. 26:1051, and NCBI RefSeq), is a homologue of vasohibin-1. Both Vasohibin and vasohibin-2 are >95% conserved between human and mouse. (For a review on Vasohibin proteins and angiogenesis regulation see Sato Y J Biochem. 2013 January: 153(1):5-11).

As previously mentioned, inventors of the present invention are the first to identify the enzymatic activity of vasohibin. More particularly, they demonstrate that Vasohibin-1 and its homologue vasohibin-2 (VASH2) possess a non-canonical Cys-His-Ser catalytic triad and are undetected members of the transglutaminase-like cysteine proteases family.

SVBP means small vasohibin-binding protein and is a protein composed of 66 amino acids. SVBP was initially isolated from a Tohoku University team in 2010 and is described to act as a secretory chaperone for Vasohibin 1 and contributes to the anti-angiogenic activity of VASH1 (Suzuki Y, et al J Cell Sci 2010 123: 3094-3101). Another studies describes also SVBP as a secretory chaperone of the VASH2 protein (Xue X. et al Oncogene. 2013 Mar. 28; 32(13):1724-34).

Accordingly the Vasohibin/SVBP complex is composed of Vasohibin-1 or Vasohibin-2, and SVBP (Small Vasohibin-Binding Protein).

Inhibitor of Vasohibin Activity

An "inhibitor of Vasohibin activity" or "inhibitor of Vasohibin/SVBP complex activity" has its same general meaning in the art, and refers to a compound (natural or not) which has the capability of reducing or suppressing the biological activity of Vasohibin (or its complex) or of one of its member. Typically, said compound inhibits or reduces detyrosination of tubulin by the Vasohibin (or its complex). For example the compound may enter in the catalytic site in place of the substrate, or block the interaction of Vasohibin (or its complex) with tubulin/microtubules/microtubule associated proteins such as +Tips (Plus-end tracking proteins), or may bind to Vasohibin (or its complex) in manner that Vasohibin is not able to bind to tubulin/microtubules/microtubule-associated proteins such as +Tips or may inhibit the formation of Vasohibin/SVBP complex. Typically, said inhibitor is a small organic molecule or a biological molecule (e.g. peptides, lipid, antibody, aptamer).

As used herein the term 'or "+Tips" means "Plus-end tracking proteins". Plus end tracking proteins are MAP (Microtubule Associated Protein) proteins which bind to the tips of growing microtubules and play an important role in regulating microtubule dynamics. For example, +TIPs have been observed to participate in the interactions of microtubules with chromosomes during mitosis. The first MAP to be identified as a +TIP was CLIP170 (cytoplasmic linker protein), which has been shown to play a role in microtubule depolymerization rescue events. Additional examples of +TIPs include EB1, EB2, EB3, p150Glued, Dynamitin, Lis1, CLIP115, CLASP1, and CLASP2 . . . ).

By "biological activity" of Vasohibin or of Vasohibin/SVBP complex (which is same) is meant detyrosination of alpha tubulin (monomer, dimers or polymerised in microtubules) associated with the detyrosination/tyrosination cycle of tubulin.

Tests for determining the capacity of a compound to be inhibitor of Vasohibin (or its complex) activity are well known to the person skilled in the art. The present application further provides a test which advantageously allows screening and selecting candidate inhibitors of Vasohibin and/or of the Vasohibin/SVBP complex, i.e. TCP (see below). In a preferred embodiment, the inhibitor specifically binds to Vasohibin (or its complex) in a sufficient manner to inhibit the biological activity of Vasohibin. Binding to Vasohibin (or its complex) and inhibition of the biological activity of Vasohibin may be determined by any competing assays well known in the art. For example the assay may consist in determining the ability of the agent to be tested as Vasohibin activity inhibitor to bind to Vasohibin (or its complex). The binding ability is reflected by the KD measurement. The term "KD", as used herein, is intended to refer to the dissociation constant, which is obtained from the ratio of Kd to Ka (i.e. Kd/Ka) and is expressed as a molar concentration (M). KD values for binding biomolecules can be determined using methods well established in the art. In specific embodiments, an inhibitor that "specifically binds to Vasohibin (or its complex)" is intended to refer to an inhibitor that binds to human Vasohibin (or its complex) polypeptide(s) with a KD of 1 µM or less, 100 nM or less, 10 nM or less, or 3 nM or less. Then a competitive assay may be settled to determine the ability of the agent to inhibit biological activity of Vasohibin. The functional assays may be envisaged such evaluating the ability to induce or inhibit the detyrosination of alpha tubulin in cells or in vivo (see example and FIG. 1).

The skilled in the art can easily determine whether a Vasohibin (or its complex) activity inhibitor neutralizes, blocks, inhibits, abrogates, reduces or interferes with a biological activity of Vasohibin. To check whether the Vasohibin activity inhibitor binds to Vasohibin (or its complex) and/or inhibit the detyrosination of alpha tubulin in cells in the same way than the initially characterized alkyne-epoY compound may be performed with each inhibitor. For instance detyrosination of alpha tubulin assay can be measured by radioactivity tests using [$^{14}$C]-tyrosinated taxol-stabilized microtubule or [$^{14}$C]-tyrosinated tubulin, as described in the Examples section (and in Arce et al (1978) J Neurochemistry (31) 205-210. Argarana et al (1980) Journal of Neurochemistry, 34(1) 114-118).

In a particular embodiment, the activity inhibitor according to the invention is an antibody or portions thereof.

In this embodiment, the activity inhibitor of Vasohibin (or its complex) is an antibody (the term including antibody fragment or portion) that can bind to Vasohibin (or its complex) in the cells and block its biological activity.

In preferred embodiment, the activity inhibitor of Vasohibin may consist in an antibody directed against the Vasohibin/SVBP complex or Vasohibin, in such a way that said antibody impairs Vasohibin/activity ("neutralizing antibody").

Then, for this invention, neutralizing antibody of Vasohibin/SVBP complex or Vasohibin are selected as above described for their capacity to (i) bind to Vasohibin (or its complex) and/or (ii) inhibiting the detyrosination of alpha tubulin by the Vasohibin (or its complex).

In one embodiment of the antibodies or portions thereof described herein, the antibody is a monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

Antibodies are prepared according to conventional methodology. Monoclonal antibodies may be generated using the method of Kohler and Milstein (Nature. (1975) 256:495). To prepare monoclonal antibodies useful in the invention, a mouse or other appropriate host animal is immunized at suitable intervals (e.g., twice-weekly, weekly, twice-monthly or monthly) with antigenic form of vasohibins (I or 2) or of SVBP. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the recombinant Vasohibin/SVBP complex (or one of its members) may be provided by expression with recombinant cell lines (or with various other expression systems including bacteria, yeast or insect cells). Recombinant form of Vasohibin and/or SVBP may be provided using any previously described method. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology. Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark. W. R. (1986) The Experimental Foundations of Modern Immunology Wiley & Sons, Inc., New York; Roitt, I. (1991) Essential Immunology, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are tour framework regions (FR1 through FR4) separated respectively by three complementarity determining regions (CDR1 through CDRS). The CDRs, and in particular the CDRS regions, and more particularly the heavy chain CDRS, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

As the Vasohibin (or its complex) is an intracellular target, the antibody of the invention acting as an activity inhibitor could be an antibody fragment without Fc fragment.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab)2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4, in an embodiment, the antibody according to the invention is a single domain antibody.

The term "single domain antibody" (sdAb) or "VHH" refers to the single heavy chain variable domain of antibodies of the type that can be found in Camelid mammals which are naturally devoid of light chains. Such VIII are also called "Nanobody®". According to the invention, sdAb can particularly be llama sdAb.

Example of neutralizing human Vasohibin (or its complex or one of its member) antibody is disclosed or available for VASH 1 in: Saito M et al. The Journal of Biochemistry, 160(4), October 2016, p. 227-232); (Watanabe, K., et al. (2004). J. Clin. Invest. 114, 898907) and Anti-Vasohibin 1/VASH1 Antibody (C-Terminus) IHC-Plus™ LS-B9515 (Lifespan Bioscience)

VASH2 in: Koyanagi T. et al Cancer Sci. 2017 March; 108(3):512-519); U.S. Pat. No. 9,701,744, and Anti-VASH2 Therapeutic Antibody (1760) TAB-248CQ (creative biolab). Anti-VASH2 (H100079805-H01) Novus bio.

SVBP in Anti-SVBP antibody (HPA008507 SIGMA)

Inhibitor of Vasohibin (or its Complex) Expression

An "inhibitor of Vasohibin expression" or "inhibitor of Vasohibin/SVBP complex expression" refers to a natural or synthetic compound that has a biological effect to inhibit or significantly reduce the expression of at least one gene encoding for at least one different member of Vasohibin (or its Complex).

In a particular embodiment inhibitor of Vasohibin expression is selected from the group consisting of inhibitor of expression of vasohibin 1 or vasohibin 2.

In a particular embodiment inhibitor of Vasohibin/SVBP complex expression is selected from the group consisting of inhibitor of expression of vasohibin 1, vasohibin 2 or SVBP.

TABLE 1

Vasohibin/SVBP complex member

| Vasohibin/SVBP complex member | Gene ID (human gene) | NCBI accession Number (human protein) |
|---|---|---|
| Vasohibin 1 (Also known as KIAA1036) | 22846 | isoform 1 NM_014909 → NP_055724 |
| | | isoform 2 XM_017021088 → XP_016876577 |
| | | isoform 2 XM_017021087 → XP_016876576 |
| | | isoform 2 XM_017021089 → XP_016876578 |
| | | isoform 2 XM_017021090 → XP_016876579 |
| | | isoform 3 XM_017021091 → XP_016876580 |
| Vasohibin 2 | 79805 | isoform 1 NM_001301056. → NP_001287985 |
| | | isoform 1 XM_011509988 → XP_011508290 |
| | | isoform 1 XM_011509987 → XP_011508289 |
| | | isoform 2 NM_024749 → NP_079025 |
| | | isoform 3 NM_001136474 → NP_001129946 |
| | | isoform 4 NM_001136475 → NP_001129947 |
| | | isoform 4 XM_017002351 → XP_016857840 |
| | | isoform 5 XM_011509989 → XP_011508291 |
| | | isoform 6 XM_011509991 → XP_011508293 |
| | | isoform 7 XM_011509994 → XP_011508296 |
| | | isoform 8 XM_017002352 → XP_016857841 |
| | | isoform 8 XM_011509995 → XP_011508297 |
| | | isoform 9 XM_011509997 → XP_011508299 |
| SVBP (Also known as CCDC23) | 374969 | NM_199342 → NP_955374 |

As shows in the Example section (FIG. 3 et 5), the use of inhibition of expression of Vasohibin1, or Vasohibin 2 or SVBP in vitro/in vivo studies clearly increase the number of neurite and branches of neurons (FIG. 3) and modify the delay of axon differentiation (FIG. 5).

In preferred embodiment the inhibitor of Vasohibin/SVBP complex expression is an inhibitor of vasohibin 1 and/or vasohibin 2 expression.

Inhibitors of expression for use in the present invention may be based on anti-sense oligonucleotide constructs. Anti-sense oligonucleotides, including anti-sense RNA molecules and anti-sense DNA molecules, would act to directly block the translation of Vasohibin/SVBP complex (or at least on one of its member) mRNA by binding thereto and thus preventing protein translation or increasing mRNA degradation, thus decreasing the level of Vasohibin/SVBP complex (or at least one of its member), and thus activity, in a cell. For example, antisense oligonucleotides of at least about 15 bases and complementary to unique regions of the mRNA transcript sequence encoding Vasohibin/SVBP complex (or one of its member) can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365, 354; 6,410,323: 6,107,091; 6,046,321: and 5,981,732).

Small inhibitory RNAs (siRNAs) can also function as inhibitors of expression for use in the present invention. Vasohibin (or its complex) gene expression can be reduced by contacting a subject or cell with a small double stranded RNA (dsRNA), or a vector or construct causing the production of a small double stranded RNA, such that Vasohibin/SVBP complex gene expression is specifically inhibited (i.e. RNA interference or RNAi). Methods for selecting an appropriate dsRNA or dsRNA-encoding vector are well known in the art for genes whose sequence is known (e.g. see Tuschl. T. et al. (1999); Elbashir, S. M. et al. (2001); Hannon, G J. (2002); McManus, M T. et al. (2002); Brummelkamp, T R. et al. (2002); U.S. Pat. Nos. 6,573.099 and 6,506,559; and International Patent Publication Nos. WO 01/36646, WO 99/32619, and WO 01/68836). All or part of the phosphodiester bonds of the siRNAs of the invention are advantageously protected. This protection is generally implemented via the chemical route using methods that are known by art. The phosphodiester bonds can be protected, for example, by a thiol or amine functional group or by a phenyl group. The 5'- and/or 3'-ends of the siRNAs of the invention are also advantageously protected, for example, using the technique described above for protecting the phosphodiester bonds. The siRNAs sequences advantageously comprises at least twelve contiguous dinucleotides or their derivatives.

As used herein, the term "siRNA derivatives" with respect to the present nucleic acid sequences refers to a nucleic acid having a percentage of identity of at least 90% with Vasohibin/SVBP complex (or at least one of its member) or fragment thereof, preferably of at least 95%, as an example of at least 98%, and more preferably of at least 98%.

As used herein, "percentage of identity" between two nucleic acid sequences, means the percentage of identical nucleic acid, between the two sequences to be compared, obtained with the best alignment of said sequences, this percentage being purely statistical and the differences between these two sequences being randomly spread over the nucleic acid acids sequences. As used herein, "best alignment" or "optimal alignment", means the alignment for which the determined percentage of identity (see below) is the highest. Sequences comparison between two nucleic acids sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (Ad. App. Math., vol. 2, p: 482, 1981), by using the local homology algorithm developed by NEDDLEMAN and WUNSCH (J. Mol. Biol., vol. 48, p: 443, 1970), by using the method of similarities developed by PEARSON and LIPMAN (Proc. Natl. Acd. Sci. USA, vol. 85, p: 2444, 1988), by using computer software using such algorithms (GAP, BESTFIT. BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., Nucleic Acids Research, vol. 32, p: 1792, 2004). To get the best local alignment, one can preferably used BLAST software. The identity percentage between two sequences of nucleic acids is determined by comparing these two sequences optimally aligned, the nucleic acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

shRNAs (short hairpin RNA) can also function as inhibitors of expression for use in the present invention.

Ribozymes can also function as inhibitors of expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of Vasohibin/SVBP complex (or at least one of its member) mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing vasohibin/SVBP complex. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses: herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV2 (Choi, VW J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV. SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter may be specific for the monocyte or macrophage.

Example of inhibitor of expression (siRNA) of human and mouse Vasohibin/SVBP complex (or one of its members) is disclosed or available for:

Vasohibin 1 in Kitajima T., et al Anticancer Research October 2014 vol. 34(10) p. 5321-5329; Miyashita H, et al (2012). PLoS ONE 7(10): e46459; Watatani H et al, Physiol Rep. 2014 June; 2(6): e12054. Vasohibin-1 Gene Silencers siRNA (h), sc-61776, (SantaCruz Biotechnology); SMARTpool: Accell VASH1 siRNA (Darmacon); invitrogen Stealth mouse siRNA MSS280250, MSS280251, and MSS280252.

Vasohibin 2 in: Tu, M., et al (2016). (Cancer Letters; 383(2), 28 December; p. 272-281); Koyanagi T. et al (Cancer Science 104(12) December 2013 p. 1705-1710); Suenaga K. et al (PLoS One. 2014; 9(9): e104728); Invitrogen Stealth mouse siRNA MSS213191. MSS280251, and MSS280252.

SVBP in Suzuki Y, et al (J Cell Sci 2010 123: 3094-3101).

Example of inhibitor of expression (shRNA) of mouse Vasohibin/SVBP complex (or one of its members) use in the example section are

```
Vasohibin-1:
                                     (SEQ ID No 1)
CCGAGACATGCGGCTCAAGATTGGCAAGG Vasohibin-2:
                                     (SEQ ID No 2)
AGACAAATCGCCTGCTCTGACCGAGAAGA SVBP:
                                     (SEQ ID No 3)
AGAGTGGAGAAGGCTAAGCAGAAATCTGC
```

Pharmaceutical Composition

The inhibitor of Vasohibin/SVBP complex activity or expression may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The Inhibitor of Vasohibin/SVBP complex activity or expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The inhibitor of Vasohibin/SVBP complex activity or expression of the invention may be formulated within a therapeutic mixture to comprise about 0.0001 to 1.0 milligrams, or about 0.00 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules: and any other form currently used.

Method of Screening

The present invention further relates to a method for screening candidate Vasohibin/SVBP complex inhibitors (also referred to as "TCP-inhibitors"). The method according to the present invention comprises the steps of:
(i) incubating a candidate compound with the Vasohibin/SVBP (TCP) and the biotinylated peptide of sequence Biotinyl-V-D-S-V-E-G-E-G-E-E-E-D-E-E-Y (SEQ ID NO: 13);
(ii) quantifying, by Mass Spectrometry, the biotinylated peptide Biotinyl-V-D-S-V-E-G-E-G-E-E-E-D-E-E-Y (SEQ ID NO: 13) and/or the biotinylated peptide Biotinyl-V-D-S-V-E-G-E-G-E-E-E-D-E-E (SEQ ID NO: 12) present in the mixture obtained at the end of step (i); and
(iii) determining whether the candidate compound is a TCP inhibitor in view of the results obtained in step (ii).

The peptide of SEQ ID NO: 13 is a substrate of TCP and a product of reaction with TTL. Accordingly, when the candidate compound is a TCP inhibitor, the quantity of this peptide quantified in step (ii) is substantially the same as the quantity of peptide originally incubated in step (i).

The peptide of SEQ ID NO: 12 is a substrate of TTL and a product of reaction with TCP. Accordingly, when the candidate compound is not a TCP inhibitor, the quantity of this peptide increases during step (i).

The present method allows for the rapid and accurate detection of TCP-inhibitors (see the results presented in Example 7 below). The claimed method allows determining inhibitory characteristics of the test compound; typically the present method allows determining the half maximal inhibitory concentration (Co) of the inhibitor.

The above screening method can further comprise a pre-incubation step, in which TCP and the test compound are pre-incubated prior to be placed in contact with the peptide of SEQ ID NO: 13.

The incubation step is carried out under conditions allowing TCP activity. Typically, the incubation step is performed at a temperature between 15° C. and 25° C. Typically, the incubation step is performed at room temperature.

The incubation step is performed over a time-period sufficient for allowing TCP activity. Typically, said time-period is from 5 to 60 minutes, more particularly from 10 to 30 minutes.

The quantification step is performed by using Mass Spectrometry (MS). Typically, the mass spectrometer is a RapidFire® mass spectrometer. In a further embodiment, the mass spectrometer is operated in electrospray negative ion-mode.

In a further embodiment, the screening method comprises, between steps (i) and (ii), a purifying step in which the biotinylated peptides of SEQ ID NO: 12 or 13 are isolated so as to be quantified in step (iii).

This purification can be performed by any method know by the skilled person for isolating biotinylated peptides. The purifying step can particularly be performed by using any means allowing for the specific binding of biotin. For instance, any device comprising streptavidin or avidin can be used. Typically, said purifying step can be performed by using a type-C cartridge with a mass spectrometer operated in electrospray negative ion-mode.

The present invention also relates to a method for screening a plurality of candidate compounds useful for treating tubulin carboxypeptidases (TCP) associated diseases comprising the steps consisting of (a) testing each of the candidate compounds for its ability to inhibit Vasohibin/SVBP complex or Vasohibin activity or expression and (b) and positively selecting the candidate compounds capable of inhibiting said Vasohibin/SVBP complex or Vasohibin activity or expression.

Typically, the candidate compound is selected from the group consisting of small organic molecules, peptides, polypeptides or oligonucleotides. Other potential candidate compounds include antisense molecules, siRNAs, shRNA, sgRNAs or ribozymes.

Testing whether a candidate compound can inhibit Vasohibin/SVBP complexes activity or expression can be determined using or routinely modifying reporter assays known in the art.

For example, the method may involve contacting cells expressing Vasohibin (or its complex) with the candidate compound, and measuring the Vasohibin (or its complex) mediated transcription (e.g., activation of promoters containing Vasohibin/SVBP complex (or at least one of its member) binding sites), and comparing the cellular response to a standard cellular response. Typically, the standard cellular response is measured in absence of the candidate compound. A decrease cellular response over the standard indicates that the candidate compound is an inhibitor of Vasohibin/SVBP complex expression (or at least one of its member).

In another embodiment the invention provides a method for identifying a ligand which binds specifically to Vasohibin/SVBP complexes (or one of its member). For example, a cellular compartment, such as a membrane or a preparation thereof, may be prepared from a cell that expresses a molecule that binds Vasohibin (or its complex). The preparation is incubated with labelled Vasohibin/SVBP complex or labelled Vasohibin and complexes of ligand bound to Vasohibin (or its complex) are isolated and characterized according to routine methods known in the art. Alternatively, the Vasohibin (or its complex) interacting polypeptide may be bound to a solid support so that binding molecules solubilized from cells are bound to the column and then eluted and characterized according to routine methods. In another embodiment, a cellular compartment, such as a membrane or a preparation thereof, may be prepared from a cell that expresses a molecule that binds Vasohibin (or its complex) such as a molecule of a signalling or regulatory pathway modulated by Vasohibin (or its complex) such as detyrosination of tubulin. The preparation is incubated with labelled Vasohibin (or its complex) in the absence or the presence of a candidate compound. The ability of the candidate compound to bind the binding molecule is reflected in decreased binding of the labelled ligand. Molecules which bind gratuitously. i.e., without inducing the effects of Vasohibin/SVBP complex or Vasohibin on binding the Vasohibin/SVBP complex or Vasohibin binding molecule, are most likely to be good inhibitor of Vasohibin/SVBP complex or Vasohibin activity.

Another method involves screening for compounds which inhibit Vasohibin activity by determining, for example, the amount of transcription from promoters containing Vasohibin; (or its complex) binding sites in a cell that expresses Vasohibin (or its complex. Such a method may involve transfecting a eukaryotic cell with DNA encoding Vasohibin (or its complex) such that the cell expresses Vasohibin (or its complex), contacting the cell with a candidate compound, and determining the amount of transcription from promoters containing Vasohibin (or its complex) binding sites. A reporter gene (e.g., GFP) linked to a promoter containing an Vasohibin (or its complex) binding site may be used in such a method, in which case, the amount of transcription from the reporter gene may be measured by assaying the level of reporter gene product, or the level of activity of the reporter gene product in the case where the reporter gene is an enzyme. A decrease in the amount of transcription from promoters containing Vasohibin (or its complex) binding sites in a cell expressing Vasohibin (or its complex, compared to a cell that is not expressing Vasohibin (or its complex), would indicate that the candidate compound is an inhibitor of Vasohibin activity.

Another method involves screening for compounds which inhibit Vasohibin biological activity by determining, the level of detyrosination of alpha tubulin, with for instance the radioactivity tests using [$^{14}$C]-tyrosinated taxol-stabilized microtubule, enzyme activity as described above and in example sections (ICP activity assay).

Accordingly the candidate compounds that have been positively selected for the binding test may be subjected to further selection steps in view of further assaying its properties on the inhibition of detyrosination of alpha tubulin with a TCP activity assay.

The candidate compounds that have been positively selected may also be subjected to further selection steps in view of further assaying its properties on neurons isolated from subjects suffering from neurodegenerative disease, such Alzheimer disease or neurons cell lines exposed to the neurotoxins beta-amyloid peptide. For example, the candidate compounds that have been positively selected with the screening method as above described may be further selected for their ability to inhibit the diminution of the dendritic spines from patient's neurons with Alzheimer disease or neurone cell lines exposed to the neurotoxins beta-amyloid peptide. Typically, the screening method may further comprise the steps of i) bringing into contact neurone from patients with Alzheimer disease or neuron cell lines exposed to the neurotoxins beta-amyloid peptide with a positively selected candidate compound ii) determining the density of dendritic spines of said neurons and iii) comparing the density determined at step ii) with the density determined when step i) is performed in the absence of the positively selected candidate compound. Step i) as above described may be performed by adding an amount of the candidate compound to be tested to the culture medium of the neuron. Usually, a plurality of culture samples are prepared, so as to add increasing amounts of the candidate compound to be tested in distinct culture samples. Generally, at least one culture sample without candidate compound is also prepared as a negative control for further comparison.

Finally, the candidate compounds that have been positively selected may be subjected to further selection steps in view of further assaying its properties on animal models for Alzheimer disease (for review on Alzheimer's animal model see Sasaguri H. et al (2017) EMBO J.; 36(17):2473-2487; or Götz J et al (2008) Nature Reviews Neuroscience 9, 532-544; ort Laurijssens B. et al (2013) Drug Discovery Today: Technologies Volume 10, Issue 3., Pages e319-e327). Typically, the positively selected candidate compound may be administered to the animal model and the progression of Alzheimer disease is determined and compared with the progression of Alzheimer disease in an animal model that was not administered with the candidate compound.

The invention will be further illustrated by the following figures and examples. However, these examples and figures should not be interpreted in any way as limiting the scope of the present invention.

FIGURES

FIG. 1. Purification and Identification of mouse brain TCP. (A) SDS-PAGE (silver staining) of the indicated fractions of TCP enrichment (Fraction I to IV) from mouse brain (1 µg of proteins). An ammonium sulfate precipitation step followed by two successive ion exchange columns stages was performed. (B) Fraction IV sensitivity to inhibitors. TPCK (Tosyl phenylalanyl chloromethyl ketone). TLCK (Tosyl-L-lysyl Chloromethyl ketone): commercial serine/cysteine inhibitors containing either a Phe or a Lys residue. Fraction IV activity showed a 100-fold higher sensitivity to TPCK than to TLCK, consistent with a high affinity for an aromatic residue. Parthenolide is a cellular detyrosination inhibitor containing an epoxide electrophile. E-64 is a natural product inhibitor of clan CA cysteine protease containing an epoxide electrophile. EpoY, epoEY and epoEEY are designed inhibitors containing the epoxide from E-64 coupled with Y, EY or EEY amino-acids respectively. Alkyne-epoY is a clickable version of epoY. Results are expressed as percentage of enzyme activity (radioactivity assay) in the control with DMSO (mean+/−SD, n=3-6). (C) Structure of alkyne-epoY. (D) Schematic representation of the last steps of TCP identification using Cu-catalyzed azide-alkyne cycloaddition (click reaction). (E) Labeling of putative TCP from fraction IV by TAMRA probe using alkyne-epoY (non-clickable epoY is used as control). (F) Schematic representation of mouse vasohibin-1 and vasohibin-2 (69% overall sequence homology; 77% for core domains (clear blue boxes)). These putative transglutaminase-like cysteine peptidases contain an unconventional triad of catalytic residues (Cys. His, Ser).

Figure 6A:
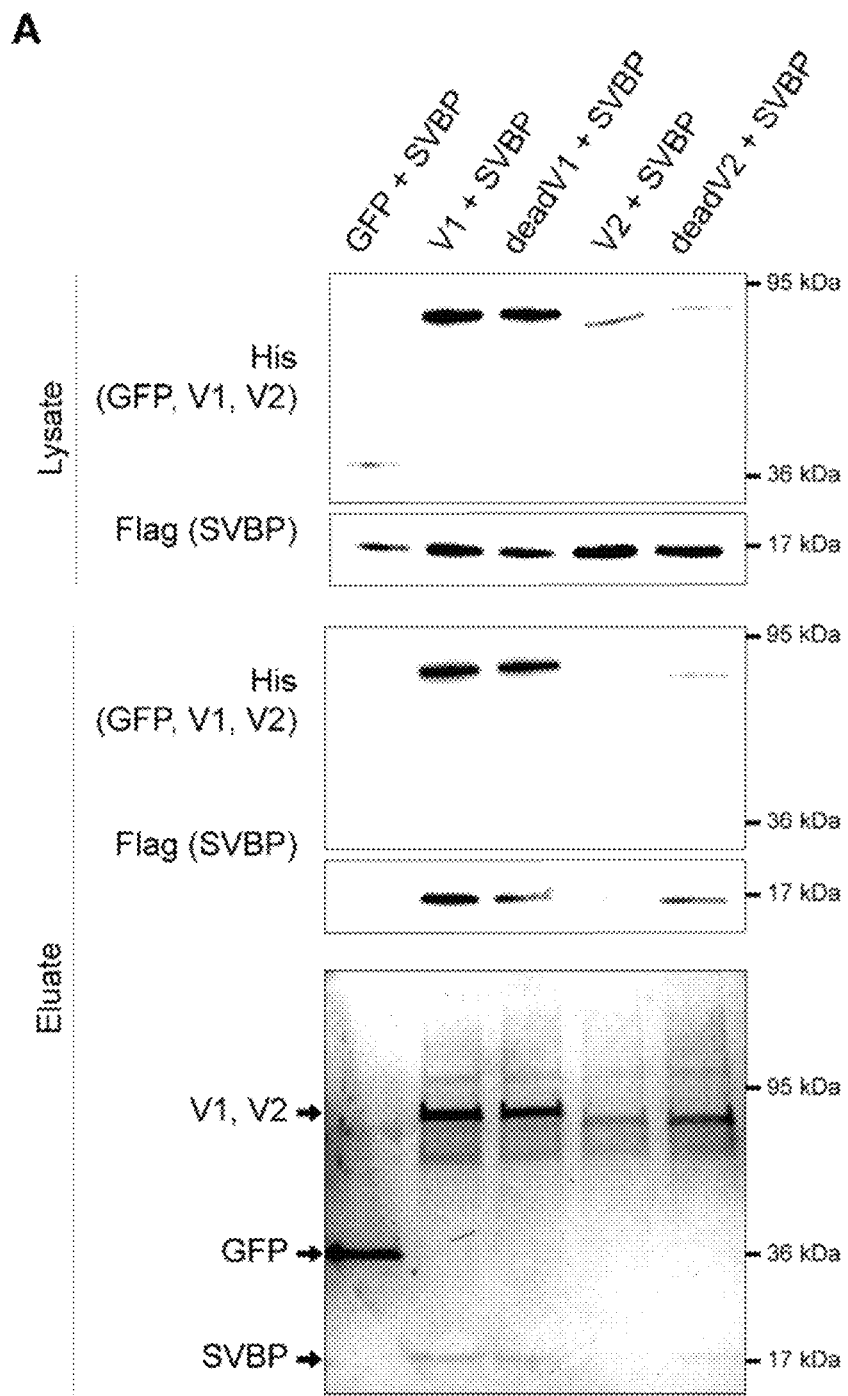

FIG. 2. Vasohibins associated to SVBP are potent tubulin tyrosine carboxypeptidases. (A) Immunoblot of endogenous tubulin from HEK293T cells expressing each VASH (V1, V2) or their dead versions in the absence or presence of exogenous SVBP co-expression. Antibodies specific to tyrosinated and detyrosinated tubulin were used to assess detyrosination. Antibodies to α-tubulin, His and Flag respectively reveal amounts of tubulin, vasohibin and SVBP. Non-transfected cells (−) show endogenous levels of tubulin modifications. ((B) Immunoblot of protein extracts from HEK293T cells expressing mCherry-α1B-tubulin, each VASH and SVBP. Native or mutated versions of α1B-tubulin, respectively ending with EEY or EEA, were used. Levels of de/tyrosinated tubulin were measured as in (A). Antibody to mCherry demonstrates same amounts of exogenous α-tubulin. (C) Detyrosination activity of purified VASH/SVBP complexes assessed using radiolabeled microtubules (6-8 µM), n=3. Active and catalytic dead versions of the vasohibins were coexpressed with SVBP in HEK293T cells and purified on cobalt resin (FIG. 6A). A purified GFP-His construct was used as a control. The theoretical maximal tyrosine release is indicated by a 100% line. (D) Detyrosination activity of purified VASH1/SVBP complexes (20 or 40 nM) on brain microtubules or tubulin dimers (5 µM) assessed by immunoblot. Similar experiments with VASH2/SVBP complexes (FIG. 63). We controlled that tubulin was in dimeric or in assembled form (FIG. 6C) and that the same amounts of enzymatic complexes were present (FIG. 6D). (E) Detyrosination activity of purified VASH/SVBP complexes (600 nM) on brain microtubules or recombinant GFP-EB1 (5 µM). Carboxypeptidase A (CPA) was used as positive control. Antibodies against tyrosinated and detyrosinated EB1 were characterized in (A. Bosson et al., (2012) PloS one 7, e33490).

FIG. 3. Down-regulation of VASH1 and VASH2 affects neuronal differentiation. (A) Vash1, Vash2 and Svbp transcripts are found in brain tissues and hippocampal neurons. RT-PCR reactions of 45 cycles were performed for all indicated tissues and cells using 50 ng of purified mRNA, except for GAPDH for which only 25 cycles were performed. (B) Western-blot analysis of the effect of VASH1 and VASH2 (shV1+shV2) or SVBP (shSVBP) down-regulation on levels of detyrosinated tubulin in neurons. Neurons were transfected by electroporation with shRNAs associated to turboGFP (tGFP) cDNA just before plating and analyzed at 2DIV (results from triplicate immunoblots of three independent neuronal cultures). (C-E) Effect of vasohibins down-regulation on neurite outgrowth and axonal differentiation. Neurons were transfected as in B and analyzed by immunostaining at 2DIV and 3DIV. (C) Stage III neurons (bearing an axon) were counted manually on immunofluorescence images from 3 to 4 different cultures at 2DIV and 3DIV. (D) Morphometric analyses of at least 85 neurons (at 2DIV) using AutoNeuriteJ macro (see Methods for details) on immunofluorescence images generated as in C. *. $P<0.05$; *. $P<0.0005$, **, $P<0.0001$ (t or Mann Whitney tests).

FIG. 4. Down-regulation of vasohibins affects radial migration of newborn cortical neurons. (A) Quantitative analysis showing the distribution of GFP positive neurons across the cortex divided into six equal bins. Data from 5 brains per condition, mean±SEM. ns, not significant, *p<0.001. **<0.0001 (Mann Whitney test). (B)

FIG. 5. Down-regulation of SVBP alters neuronal differentiation. (A) Validation of VASH1, VASH2 and SVBP shRNAs. HEK293T cells were co-transfected with plasmids allowing expression of the protein and of the corresponding shRNA or of a control shRNA. Crude protein extracts were analyzed by Western-blot with anti-GFP and anti-Flag to test the presence of VASH1/2 or SVBP, respectively, and with anti-turboGFP to assay the presence of shRNA; (B-C) Effect of SVBP down-regulation on neurite outgrowth and axonal differentiation. Neurons were transfected as in FIG. 3B and analyzed by immunostaining at 2DIV and 3DIV. (B) Stage III neurons (bearing an axon) were counted manually on immunofluorescence images from 3 to 4 different cultures at 2DIV and 3DIV. (C) Morphometric analyses of at least 27 neurons (at 2DIV) using AutoNeuriteJ macro (see Methods for details) on immunofluorescence images generated as in B. *, P<0.05; , P<0.005; *, P<0.0005 (t or Mann and Whitney tests).

FIG. 6. Purification and properties of VASH/SVBP complexes. (A) Western-blot analysis (upper panels) and SDS-PAGE (lower panel) of the purification of vasohibin/SVBP complexes. Vasohibins and their catalytic dead versions were co-expressed with SVBP in HEK293T cells as in FIG. 2A and then purified on cobalt resin. A GFP only construct (bearing an His-tag) was used as a control. GFP and vasohibins were probed with anti-His antibody, and SVBP with anti-Flag antibody. Western-blot analyses of unpurified (lysate) and purified (eluate) protein extracts and SDS-PAGE of purified protein extract are presented. Note that SVBP was co-purified with all vasohibins but not with GFP. (B) Detyrosination activity of purified VASH2/SVBP complexes on purified brain microtubules or tubulin dimers assessed as in FIG. (2D). (C) Control by SDS-PAGE of non-assembled microtubule (tubulin dimers. Tub) or assembled microtubules (MT) used in FIG. (2D). MT and Tub extract (500 ng) were centrifuged 15 min at 25° C. and 200,000 g. SN, supernatant. (D) Control by Western-blot of VASH1. VASH2 and SVBP amounts used in FIG. 2D.

Figure 7:
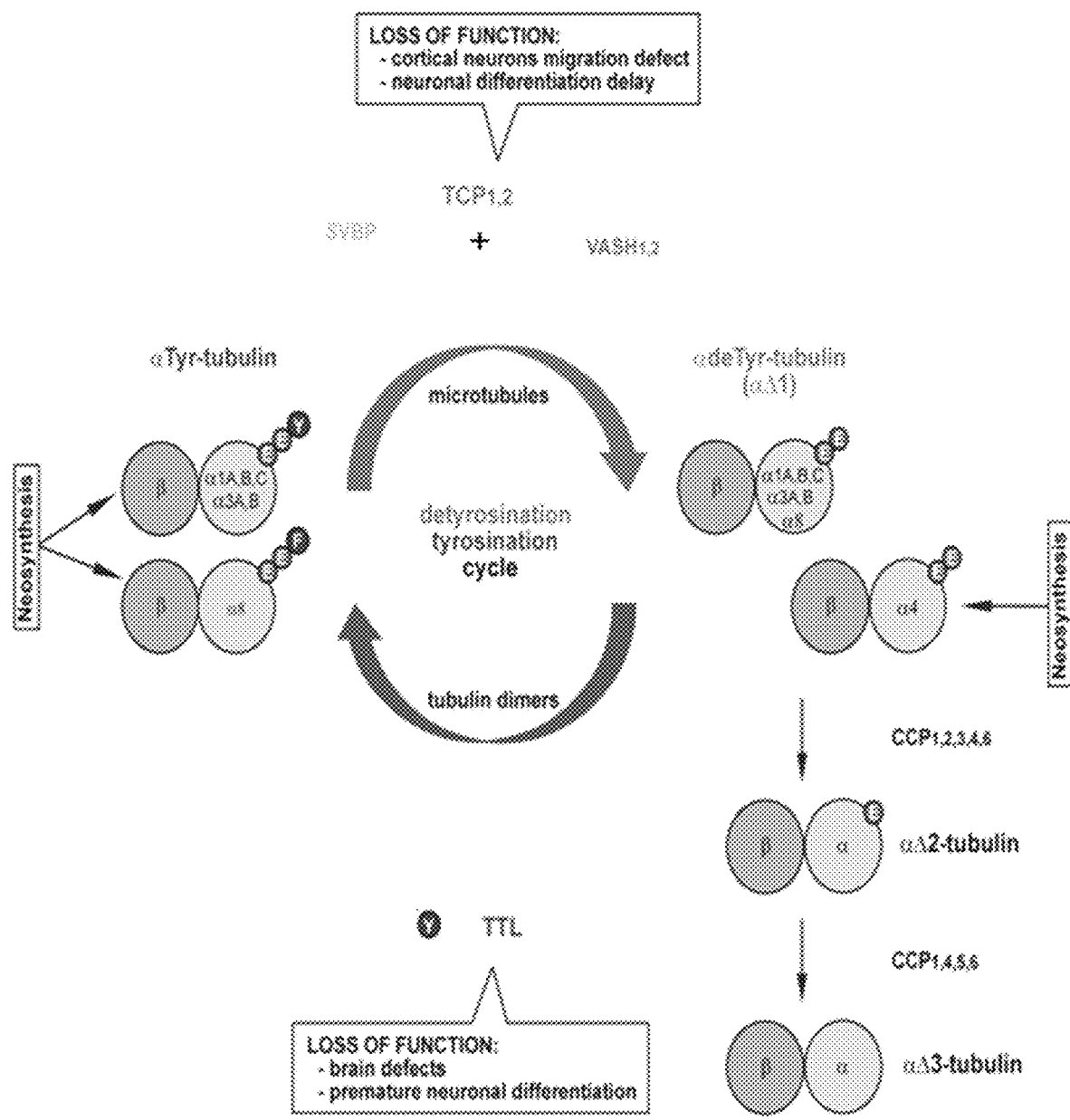

FIG. 7. Detyrosination/tyrosination cycle and implicated enzymes: a central position of tubulin carboxypeptidase (TCP). α-tubulin is usually neosynthesized with a C-terminal aromatic residue, tyrosine for most genes or phenylalanine for α8 gene (V. K. Khodiyar et al., (2007) Genomics 90, 285). α-tubulin can enter into the de/tyrosination cycle when the αβ-tubulin dimer incorporates a microtubule and becomes a TCP substrate. TCP removes the last aromatic residue generating microtubule bearing detyrosinated α tubulin (or αΔ1-tubulin). Detyrosinated α tubulin pool can also be fed by the direct neosynthesis from α4 gene coding for an α-tubulin without last aromatic residue. To complete the cycle, the microtubule depolymerizes and liberates detyrosinated dimers which can be re-tyrosinated by tubuline tyrosine ligase (TTL). Whereas TTL enzyme consists of a single protein, TCP enzymes discovered in the present study comprise a catalytic unit (vasohibin) and an accessory protein (SVBP, small vasohibin-binding protein). Due to a duplication event of an ancestral vasohibin gene, vertebrates possess two TCP catalytic subunits, vasohibin-1 (VASH1) and vasohibin-2 (VASH2). Detyrosinated α-tubulin is the source of other modifications. Penultimate and ante-penultimate glutamate residues can be sequentially processed by the CCP family enzymes to generate αΔ2- and αΔ3 tubulin, respectively (L. Paturle-Lafanechere et al., (1994) Journal of cell science 107 (Pt 6), 1529; C. Aillaud et al., (2016) Molecular biology of the cell 27, 640; K. Rogowski et al., (2010) Cell 143, 564).

Figure 8:
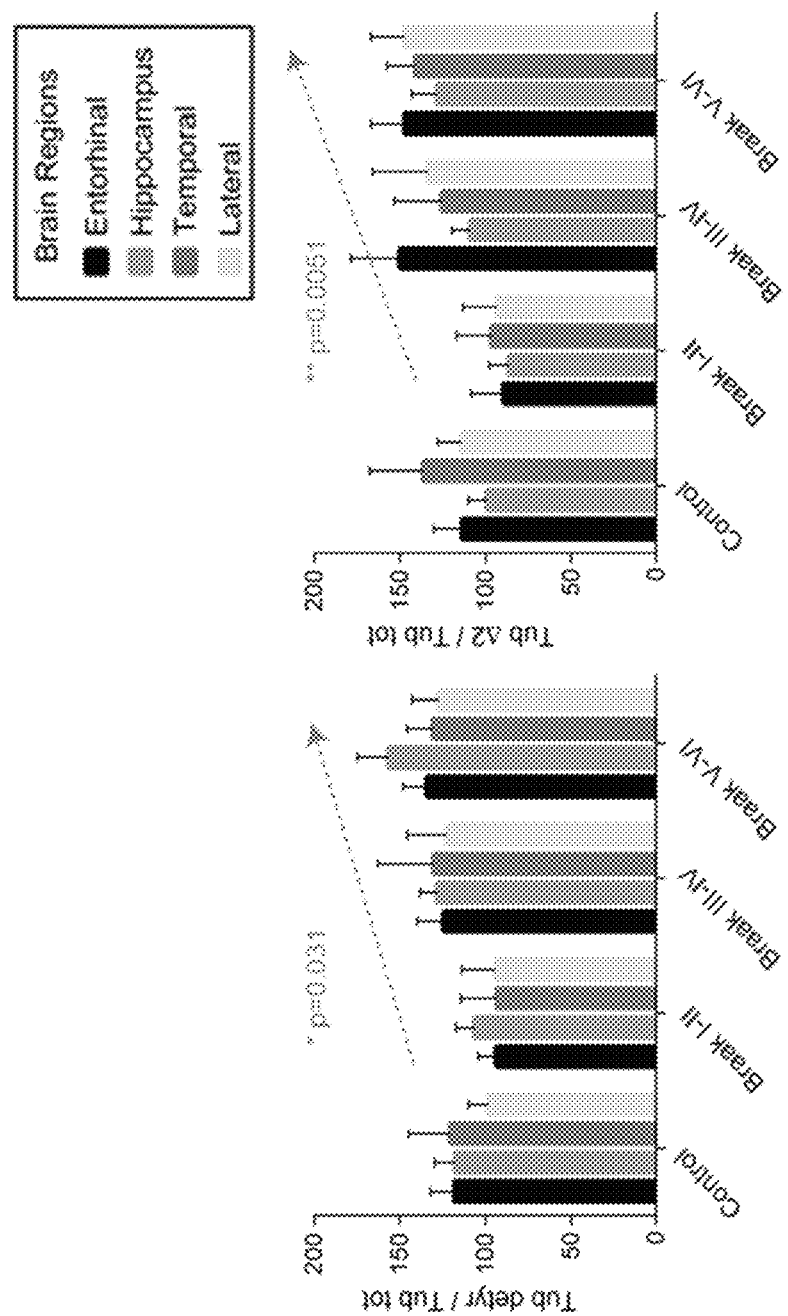

FIG. 8. Comparison of tubulin detyrosination status in brain of AD and control patients. Immunoblot analysis was performed with protein extracts from entorhinal, hippocampus, temporal and lateral brains tissues from healthy aged matched (control) and AD patients with Braak of I to VI, classified in I-II, (AD early), III-IV (AD middle) and V-VI (AD late). Quantifications were performed from 3 independent experiments and a "control" brain sample was used in the entire set of the experiments allowing internal standardization. The analyzed samples were: control n=11, Braak stadium 1-11 n=5, Braak stadium II-IV n=6 and Braak stadium IV-V n=7. Detyrosinated and Δ2 tubulin were standardized to total tubulin. All data presented as mean±SEM. Two ways ANOVA using Mix Models. The sources of variations are Braak and brain region. The region effect is not significant and the effect Braak is significant for Tub detyr/Tub tot (* p=0.031) and for Tub Δ2/tub tot (** p=0.0051).

Figure 9:
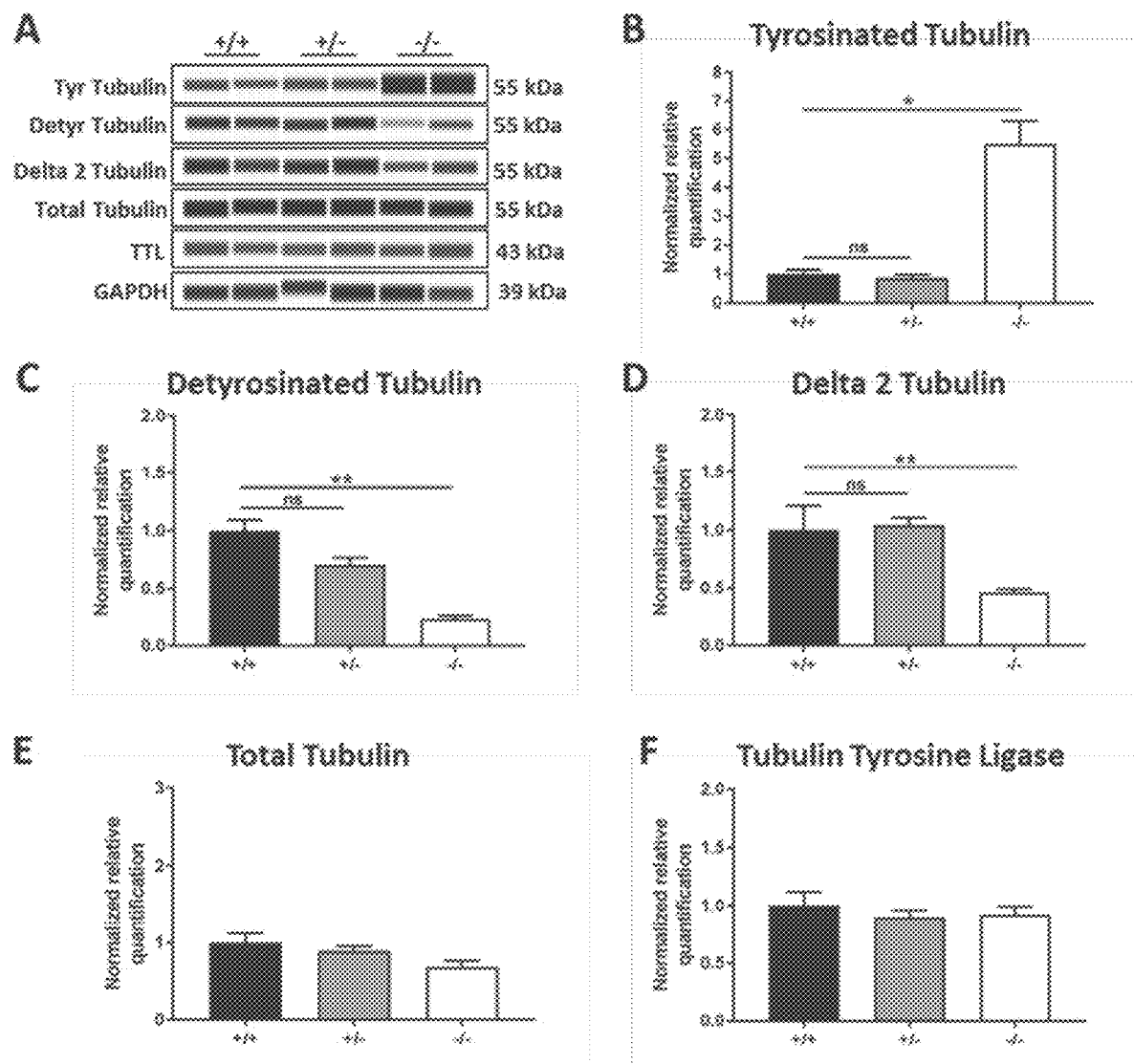

FIG. 9: Down expression of VASH1 affects the tubulin tyrouination in brain. Capillary Western blot of tyrosinated-tubulin, detyrosinated-tubulin, delta2-tubulin, α-tubulin and TTL (A). Relative quantification of the tyrosinated (B), detyrosinated (C), delta 2 (D) and total α-tubulin (E) and the tubulin tyrosine ligase (F) levels in hippocampus from VASH1 KO heterozygous (+/−), homozygous (−/−) and wild type mice (+/+) mice (mean±SEM). Statistical comparisons were performed using non-parametric Kruskal-Wallis test followed by Dunn's multiple comparison tests. p<0.01, **p<0.0001 compared to WT mice.

Figure 10:
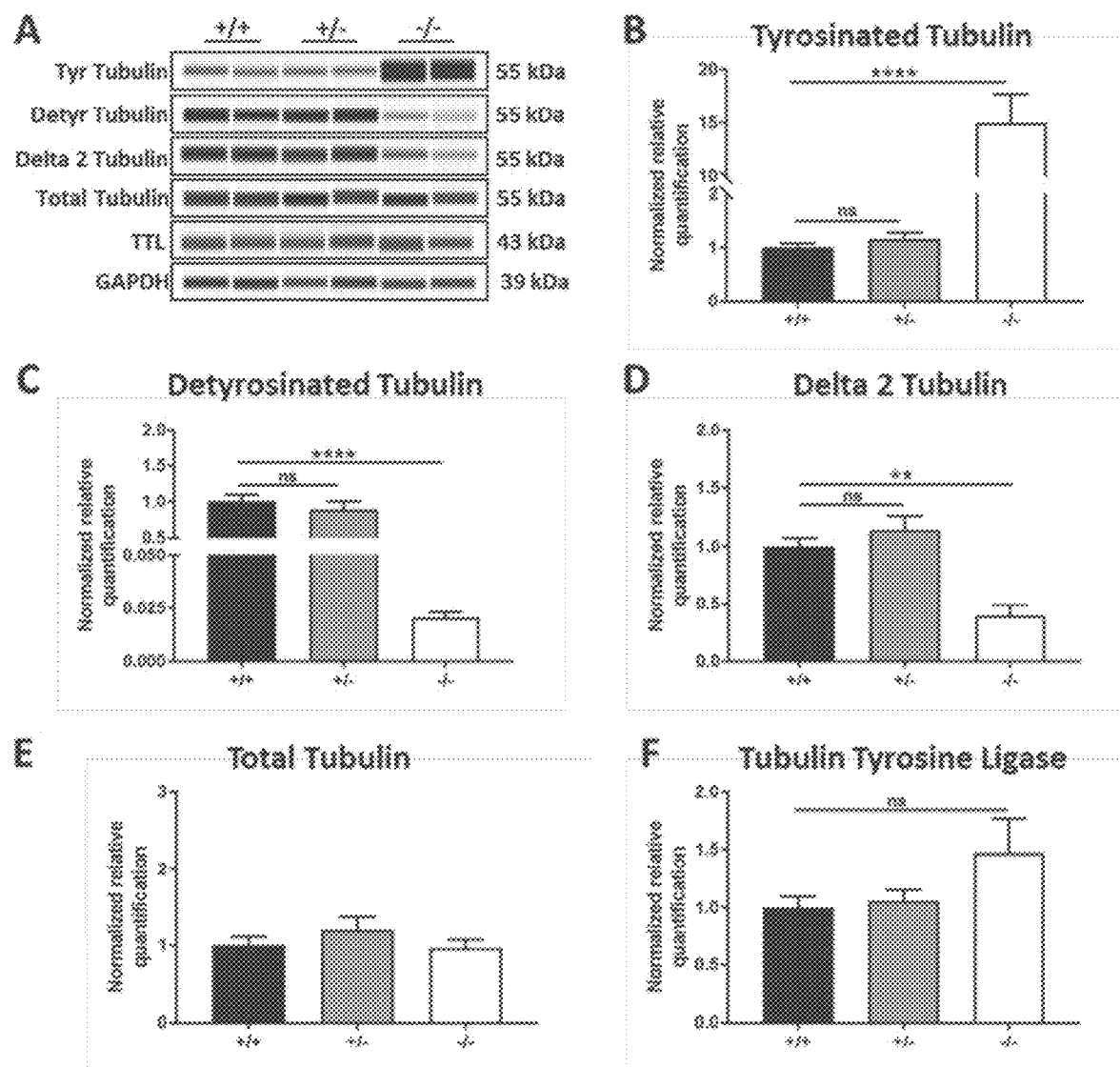

FIG. 10: Down expression of SVBP affects the tubulin tyrosination in brain. Capillary Western blot of tyrosinated-tubulin, detyrosinated-tubulin, delta2-tubulin, α-tubulin and TTL (A). Relative quantification of the tyrosinated (B), detyrosinated (C), delta 2 (D) and total α-tubulin (E) and the tubulin tyrosine ligase (F) levels in hippocampus from SVBP KO heterozygous (+/−), homozygous (−/−) and wild type mice (+/+) mice (mean±SEM). Statistical comparisons were performed using non-parametric Kruskal-Wallis test followed by Dunn's multiple comparison tests. p<0.01, **p<0.0001 compared to WT mice.

Figure 11:
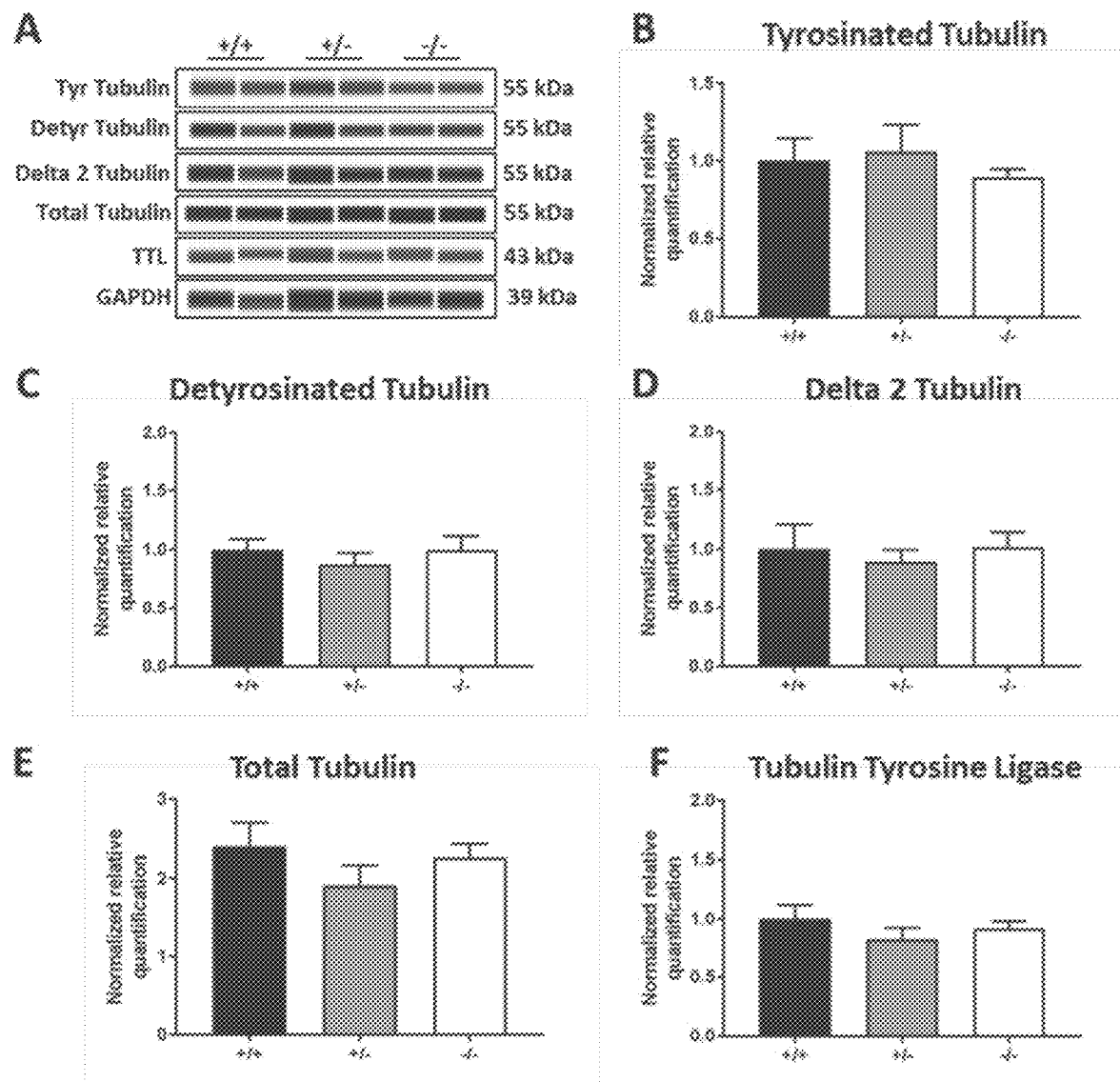

FIG. 11: Down expression of VASH2 doesn't affect the tubulin tyrosination in brain. Capillary Western blot of tyrosinated-tubulin, detyrosinated-tubulin, delta2-tubulin, α-tubulin and TTL (A). Relative quantification of the tyrosinated (B), detyrosinated (C), delta 2 (D) and total α-tubulin (E) and the tubulin tyrosine ligase (F) levels in hippocampus from VASH2 KO heterozygous (+/−), homozygous (−/−) and wild type mice (+/+) mice (mean±SEM). Statistical comparisons were performed using non-parametric Kruskal-Wallis test followed by Dunn's multiple comparison tests.

Figure 12:
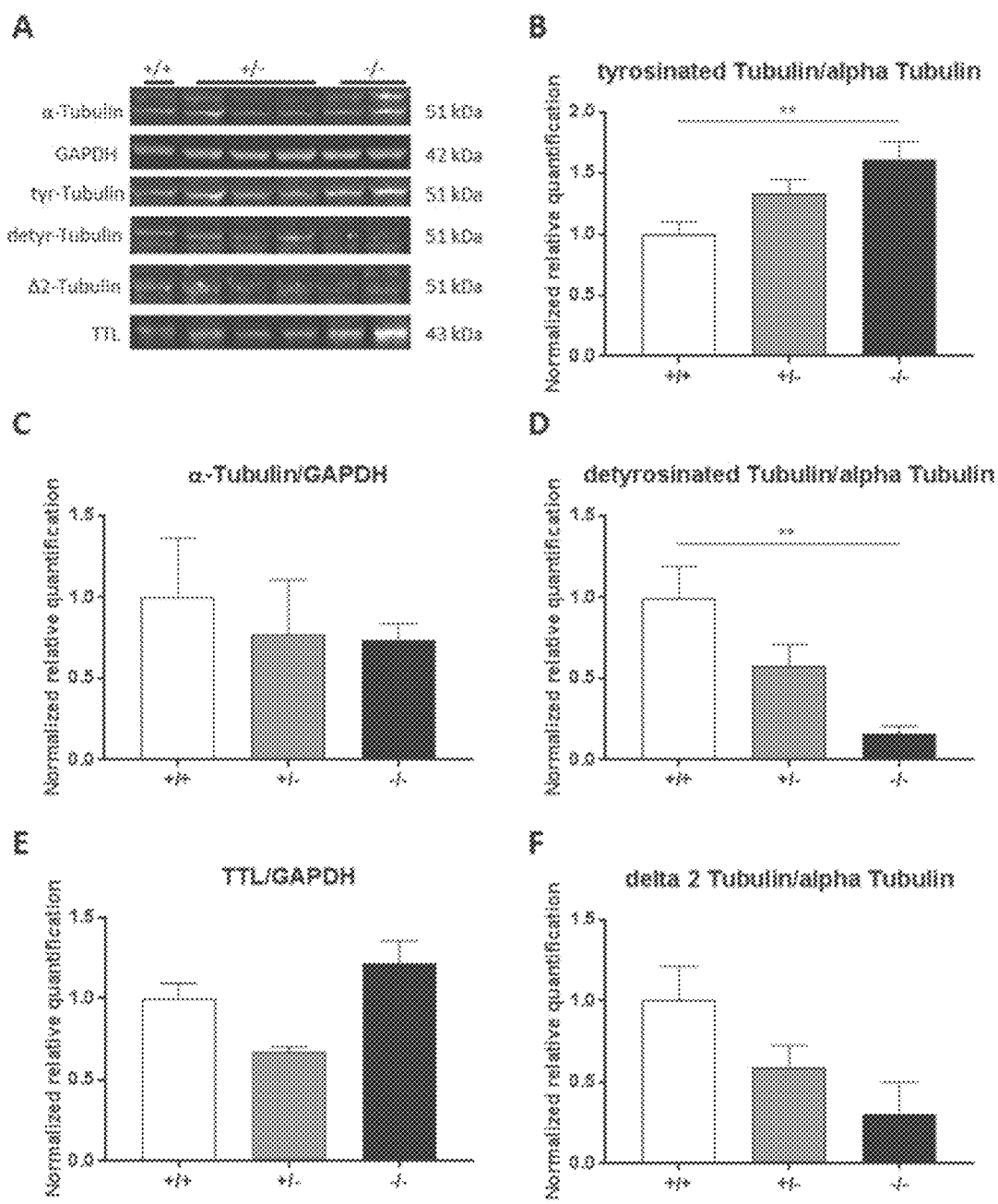

FIG. 12: Down expression of VASH1 affects the tubulin tyrosination in cardiac ventricles. Western-blot analysis of α-tubulin, tyrosinated-tubulin, detyrosinated-tubulin, delta2-tubulin and TTL (A). Relative quantification of the tyrosinated (B), detyrosinated (D), delta 2 (F) and total (C) α-tubulin and the tubulin tyrosine ligase (E) levels in heart ventricles from VASH1 KO homozygous (−/−), heterozygous (+/−) and wild type mice (+/+) mice (mean±SEM). Statistical comparisons were performed using non-parametric one-way ANOVA * p<0.05, p<0.01, **p<0.0001 compared to WT mice.

Figure 13:
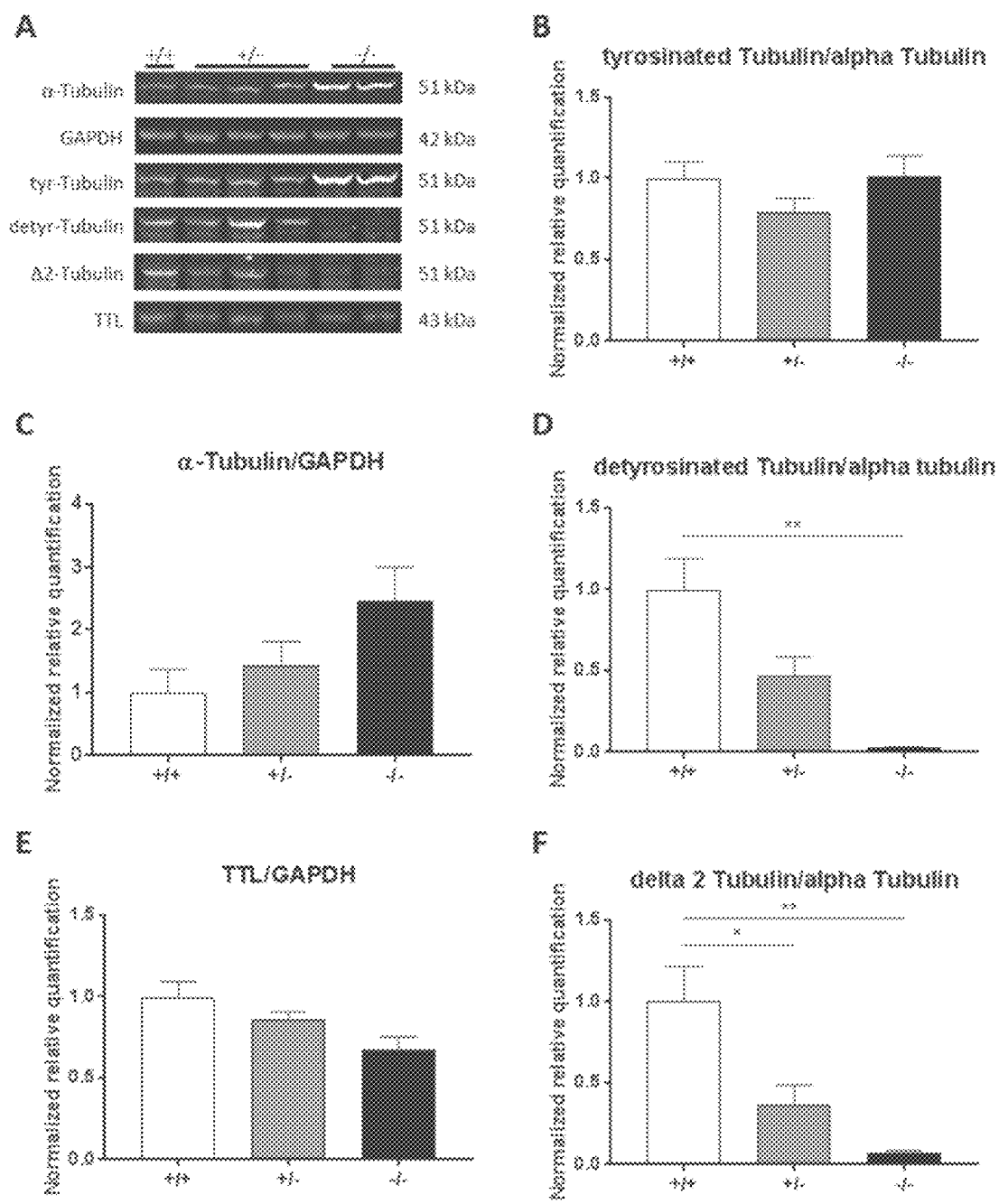

FIG. 13: Down expression of SVBP affects the tubulin tyrosination in cardiac ventricles. Western-blot analysis of α-tubulin, tyrosinated-tubulin, detyrosinated-tubulin, delta2-tubulin and TTL (A). Relative quantification of the tyrosinated (B), detyrosinated (D), delta 2 (F) and total (C) α-tubulin and the tubulin tyrosine ligase (E) levels in heart ventricles from SVBP KO homozygous (−/−), heterozygous (+/−) and wild type mice (+/+) mice (mean±SEM). Statistical comparisons were performed using non-parametric one-way ANOVA * p<0.05, p<0.01. **p<0.0001 compared to WT mice.

Figure 14:
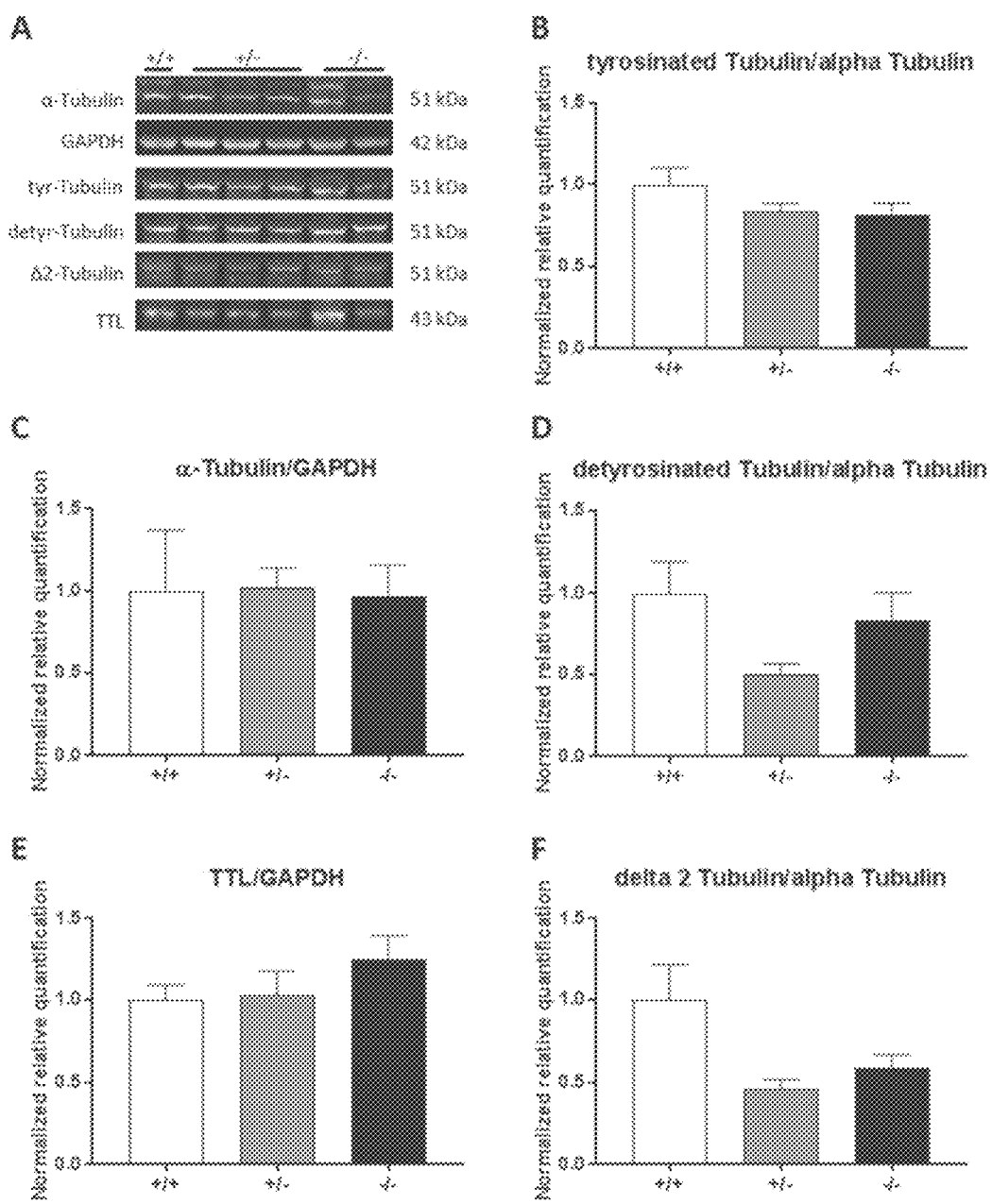

FIG. 14: Down expression of VASH2 doesn't affect the tubulin tyrosination in cardiac ventricles. Western-blot analysis of α-tubulin, tyrosinated-tubulin, detyrosinated-tubulin, delta2-tubulin and TTL (A). Relative quantification of the tyrosinated (B), detyrosinated (D), delta 2 (F) and total (C) α-tubulin and the tubulin tyrosine ligase (E) levels in heart ventricles from VASH2 KO homozygous (−/−), heterozygous (+/−) and wild type mice (+/+) mice (mean±SEM). Statistical comparisons were performed using non-parametric one-way ANOVA.

Figure 15:
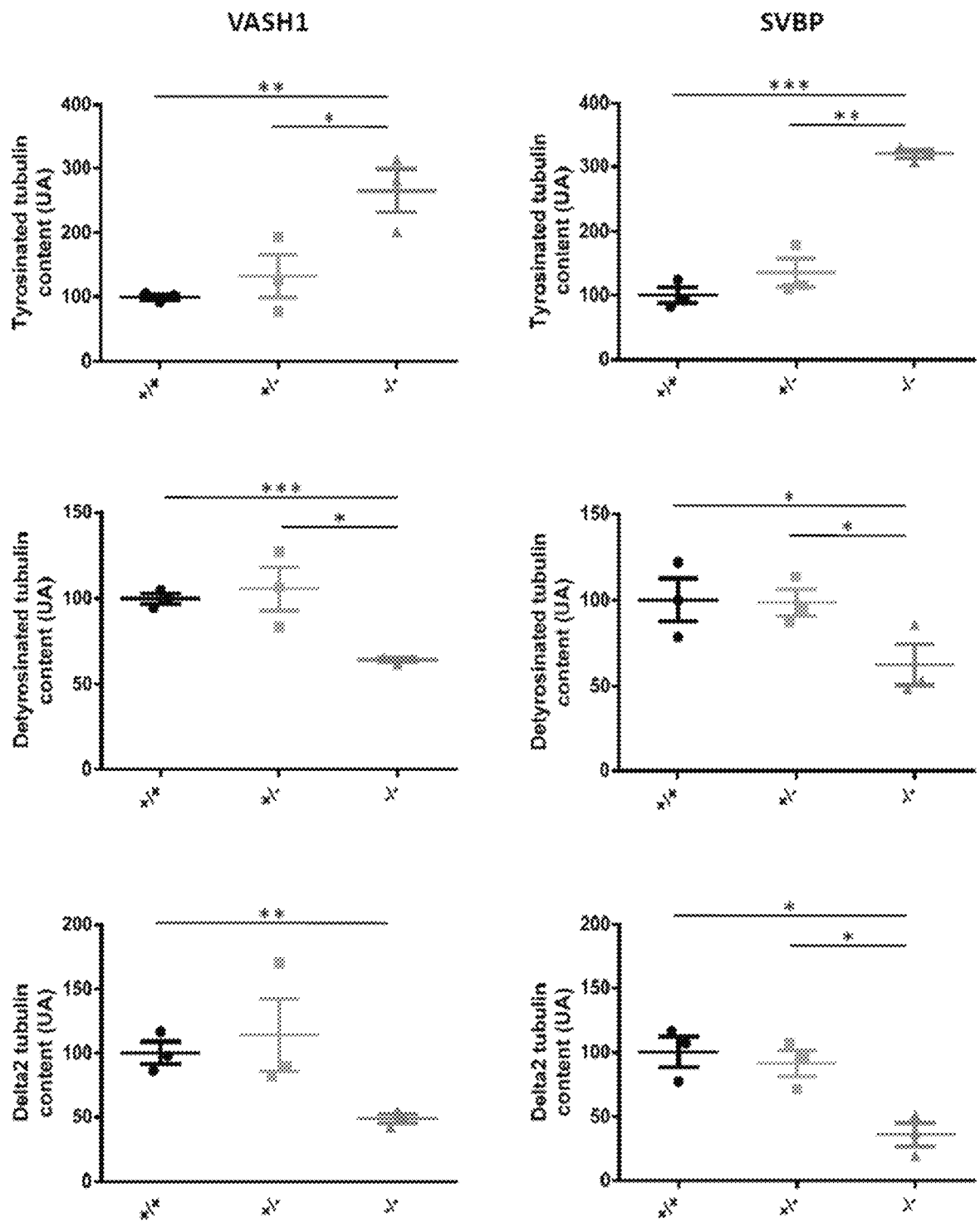

FIG. 15. Down regulation of VASH1 or SVBP affect tubulin tyrosination status in mature neurons Analysis was performed on protein extracts from 17DIV cortical neurons. Quantifications were performed from 3 independent immunoblots with extracts from 3 different embryos. (mean i SEM, t-tests). *P<0.05. P<0.01, *P<0.001.

Figure 16:
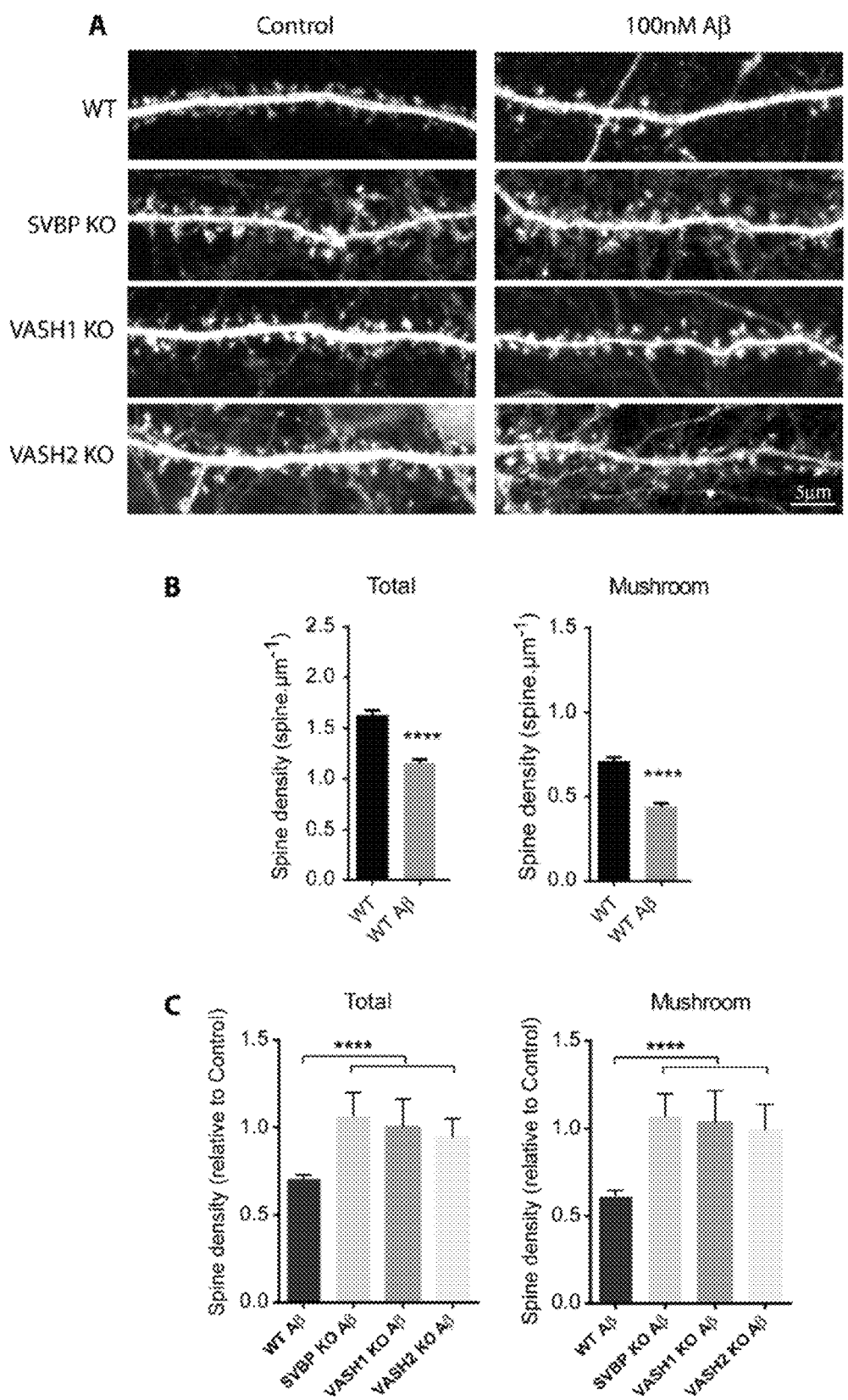

FIG. 16. Vasohibin or SVBP deletion protects mice cultured neurons from dendritic spine loss Induced by AP toxicity.

(A) Confocal images of representative examples of dendrite segments of WT, and SVBP-, VASH1- and VASH2-KO cultured neurons (17DIV) expressing GFP and treated or not with 100 nM AP oligomers for 48 h. Scale bar=5 μm. (B) Graphs of total dendritic spine density (left) or mature mushroom form of dendritic spine (right) of WT 17 DIV neurons treated or not with 100 nM Aβ. All data presented as mean±SEM. Student's t test. ** p<0.0001. (C) Graphs of total dendritic spine density (left) or mature mushroom form of dendritic spine (right) of Aβ-treated neurons from WT, and SVBP-, VASH1- and VASH2-KO 17DIV cultured neurons. Results are presented relative to non-treated (control) neurons from WT, and SVBP-, VASH1- and VASH2-KO, respectively, and as mean±SEM. One Way ANOVA with Sidak's multiple comparison test. ** p<0.0001.

Figure 17:
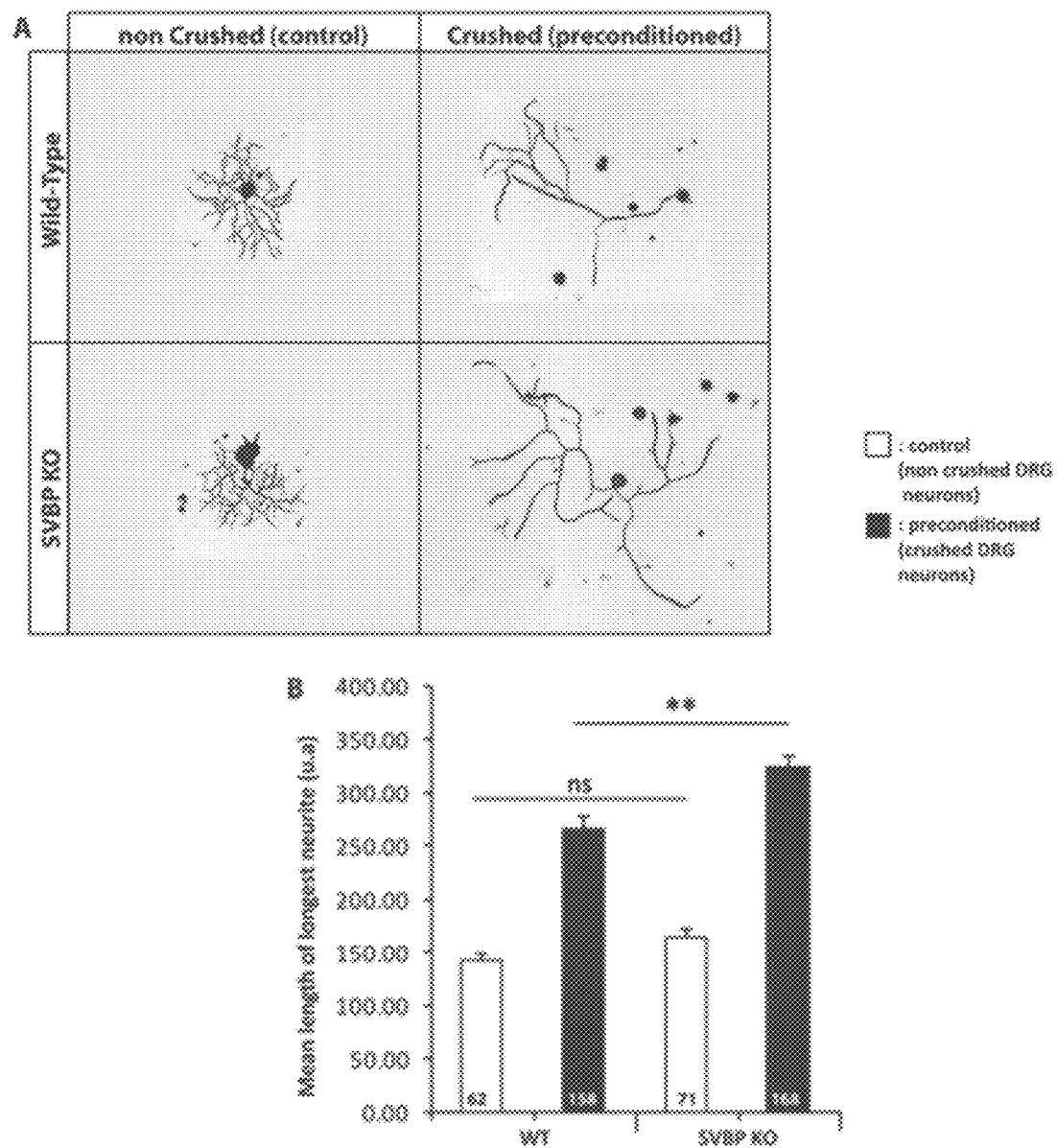

FIG. 17. In vitro analysis of conditioned axonal regrowth of wild type and SVBP KO dorsal root ganglion (DRG) neurons.

S (A) Representative adult DRG neurons dissociated and cultured either without any previous conditioning (non-crushed) or three days after a sciatic nerve crush (crushed). (B) Quantification of the longest neurite length for each neuron. n=2 independent experiments; Values on bars correspond to number of neurons quantified. Error bars represent s.e.m.; Statistical analysis: Kruskal-Wallis test with Dunn's Multiple Comparison Test; ns, statistically insignificant difference; **P<0.01. As compared to WT, SVBP KO DRG neurons significantly grow faster after the preconditioning protocol.

Figure 18:
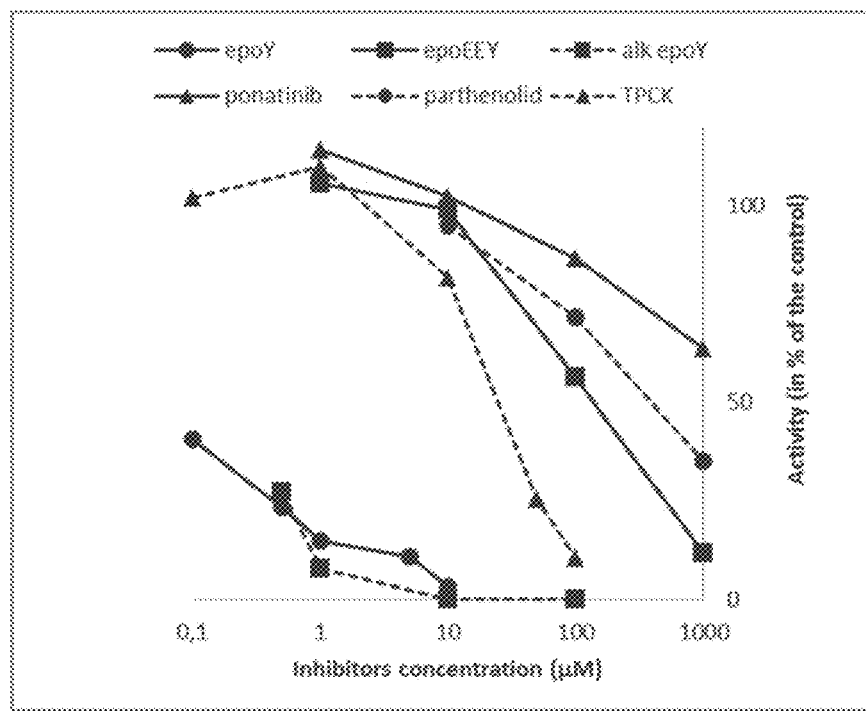

FIG. 18. VASH1/SVBP sensitivity to inhibitors.

Assays were performed using an Elisa-based method with peptide biotinyl-V-15-Y. Several inhibitors were tested: TPCK (Tosyl phenylalanyl chloromethyl ketone), commercial serine/cysteine inhibitors containing a Phe residue: ponatinib, commercial potent inhibitor of Ab tyrosine kinases; EpoY and epoEEY, designed inhibitors containing an epoxide group coupled with Y or EEY amino-acids respectively (Aillaud et al., 2017); Alkyne-epoY, clickable version of epoY. Results are expressed as percentage of enzyme activity in the control with DMSO (mean of at least duplicates).

Figure 19:
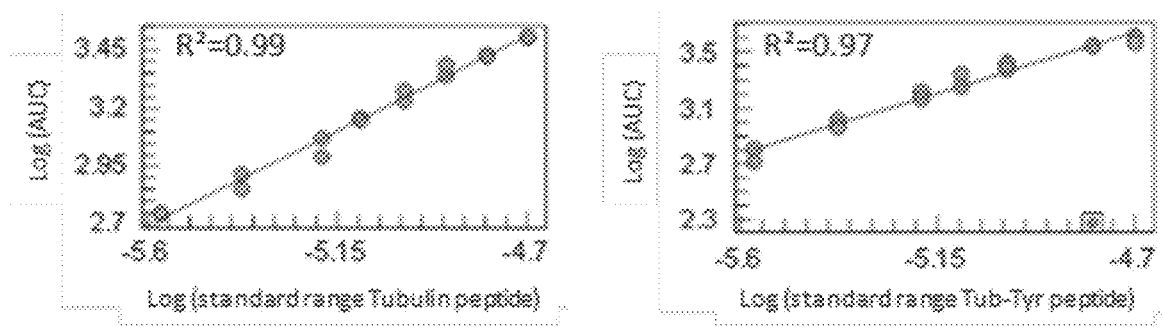

FIG. 19: Calibration curve: the calibration curve was obtained in the range of 2.7 μM and 20 μM of the two peptides (Biotinyl-V-D-S-V-E-G-E-G-E-E-E-D-E-E (SEQ ID NO: 12) and Biotinyl-V-D-S-V-E-G-E-G-E-E-E-D-E-E-Y) (SEQ ID NO: 13). Concentrations were calculated based on a 8-point calibration curve using a I/x linear curve fit.

EXAMPLE

Example 1: Identification of Vasohibins/SVBP Complexes as Potent Tubulin Tyrosine Carboxypeptidases Material & Methods:

Animals. Male or females mice were used between 2-4 months old. In accordance with the policy of the Institut des Neurosciences of Grenoble (GIN) and the French legislation, experiments were done in compliance with the European Community Council Directive of 24 Nov. 1986 (86/609/EEC). The research involving animals was authorized by the Direction Départementale de la protection des populations—Préfecture de l'Isère-France and by the ethics committee of GIN number 004 accredited by the French Ministry for of Research.

Preparation of tyrosinated tubulin and microtubule, and EB1. Bovine brain tubulin (12 mg/mL, prepared as in (S. Ramirez-Rios et al., (2016) Molecular biology of the cell 27, 2924) was tyrosinated by incubation for 45 min at 30° C. with purified chicken TTL (1 mg/mL, gift from Steinmetz group) and 0.1 mM L-tyrosine or [14C]-L-tyrosine (0.125 μCi/mole) in 40 mM Pipes at pH 6.7, 60 mM KCl, 2.5 mM ATP, 1 mM DTT, 12.5 mM MgCl2. Microtubules polymerization was allowed by one-third dilution in 100 mM PIPES at pH 6.7. 1 mM EGTA, 1 mM MgCl2, 30% glycerol, 1 mM GTP and incubation at 32° C. for 45 min, followed by another 45 min incubation with 50 μM Paclitaxel (Calbiochem). Microtubules were sedimented by 25 min centrifugation at 100,000 g and 30° C. on 60% glycerol cushions. TTL-containing supernatant was discarded and tyrosinated-microtubules were resuspended in 100 mM PIPES at pH 6.7, 1 mM EGTA, 1 mM MgCl2, 10% glycerol, 80 μM paclitaxel and stored at −20° C. To obtain unpolymerized tyrosinated-tubulin, paclitaxel was omitted during the whole procedure. EB1 was prepared as in S. Ramirez-Rios et al., (2016) Molecular biology of the cell 27, 2924.

TCP activity assays. In radioactivity tests using [14C]-tyrosinated taxol-stabilized microtubule, enzyme activity was measured in 100 mM MES at pH 6.7. 1 mM EGTA and 1 mM MgCl2 using 2 μM radiolabeled tubulin, except in FIGS. 2D and S2D (as indicated in legend). Reactions were performed for 45 min at 37° C. (without or with previous incubation with inhibitors, see legends) and were stopped on ice by addition of 20 μg/ml bovine serum albumin and 10% perchloric acid and centrifugation. Tyrosine cleaved from microtubules was estimated by measuring radioactivity in the supernatant (a zero time control was subtracted). To compose the table of Fig. S1A, detyrosination activity from equal volumes of the various fractions was measured. In tests with inhibitors, detyrosination activity was tested after a 20 min preincubation with inhibitor (except in Figs. S2C and S2) where varying time of incubation were used as indicated in legend), and results with inhibitors were expressed as percentage of the activity in the control with corresponding solvent. In tests using Western-blots, enzyme activity was assayed with 5 μM substrates (taxol-stabilized microtubule, tubulin or EB1) in 100 mM MES at pH 6.7. 1 mM EGTA and 1 mM MgCl2 for times indicated in figures. Positive controls were done with carboxypeptidase A (2 ng/mL). Reactions were stopped by addition of Laemmli buffer. A reaction with carboxypeptidase A (CPA), which efficiently cleaves aromatic and aliphatic C-terminal residues, was used as positive control. In tests using VASH/SVBP complexes purified on cobalt resin from HEK293T cells, enzymes concentration were approximated from in-gel Coomassie-blue staining of purified VASH1 and VASH2 together with standards of bovine serum albumin.

Enzyme enrichment. We designed a three-step purification procedure from brain lysate inspired from previous efforts (N. Kumar, M. Flavin, (1981) The Journal of biological chemistry 256, 7678; C. E. Argarana, H. S. Barra, R. Caputto, (1980) Journal of neurochemistry 34, 114). All steps were carried out at 4° C. Adult mice brains were homogenized in 50 mM phosphate buffer at pH 6.7, 1 mM EGTA, 1 mM MgCl2, 1 μg/ml DNAse with a protease inhibitor cocktail (cOmplete EDTA-free, Roche) and centrifuged 1 h at 100.000 g. The supernatant was collected (Fraction 1). In step 1 (ammonium sulfate fractionation), Fraction 1 was slowly brought to 45% ammonium sulfate, incubated for 15 min and centrifuged 20 min at 15,000 g. Resulting supernatant underwent the same procedure at 65% ammonium sulfate. The pellet was re-suspended in one-eighth of initial volume with 50 mM MES pH 6.7, 1 mM EGTA, 1 mM MgCl2 and desalted using Bio-Gel P30 (Bio-Rad) equilibrated with the same buffer (Fraction 11). In step 2 (strong anion column), Fraction 11 was loaded onto a 5 mL Hitrap Q XL column (GE Healthcare) connected on a BioLogic DuoFlow chromatography systems (Biorad) and unbound proteins were collected (Fraction III). In step 3 (strong cation column): Fraction III adjusted to pH 6.2 and 0.12 M NaCl, was loaded on a 5 mL Hitrap SP XL column (GE Healthcare). Proteins were eluted with a 0.12 M to 1M NaCl gradient. Protein fractions were equilibrated in 50 mM MES at pH 6.7, 1 mM EGTA, 1 mM MgCl2 (by desalting with BioGel P-30). TCP activity assay was performed on these fractions and activity containing fractions were pooled (Fraction IV). Purification data of a typical experiment are shown in FIG. 1A. For the quick enzyme enrichment, brain homogenate was directly proceeded to step 3, and then desalted.

Click chemistry (Cu-catalyzed azide-alkyne cycloaddition, CuCAAC reaction). Fraction IV was equilibrated in phosphate buffered solution at pH 7.4 and concentrated to 2 mg/ml. Following 1 h incubation at 37° C. with 10 μM of alkyne-epoY or 10 μM of epoY (respectively clickable and control irreversible inhibitors, see structures in FIG. 1C, S2B), two equivalent volumes of azide-agarose beads (Jena Biosciences) were then added and click reaction was started by addition of 1 mM CuSO4, 100 μM TBTA and 1 mM TCEP. Reaction was completed in 3 h at room temperature. For fluorescence labeling, 100 μM 5/6-TAMRA-PEG3-azide (Jena Bioscience) was used instead of azide-agarose beads.

Mass Spectrometry sample preparation. Removal of non-specifically bound proteins, and peptides preparation to be analyzed were achieved according to the Click Chemistry Capture Kit protocol (Jena Bioscience). Quickly, agarose-bound proteins were reduced and alkylated. Beads were washed with 1% SDS and 8M urea. On-beads tryptic proteolysis (using Sequencing Grade Modified Trypsin, Promega) was performed and released peptides were purified on C18 cartridges (Ultra-Micro spin columns, Harvard Apparatus).

Mass spectrometry-based proteomic analyses. Peptides were analyzed by nanoliquid chromatography coupled to tandem mass spectrometry (Ultimate 3000 coupled to LTQ-Orbitrap Velos Pro, Thermo Scientific) using a 120-min gradient as described in (U. Milbradt et al., (2014) Mol Cell Proteomics 13, 2132). Peptides and proteins were identified through concomitant searches against Uniprot (March 2017 version, *Mus musculus* taxonomy), classical contaminants (homemade) and the corresponding reversed databases using Mascot (version 2.5.1). The Proline software (proline.profiproteomics.fr) was used to filter the results (conservation of rank i peptides, peptide identification FDR <1% as calculated on peptide scores by employing the reverse database strategy, and minimum of 1 specific peptide per identified protein group) before performing a compilation, grouping and comparison of the protein groups from the control and positive samples. Proteins from the contaminants database and additional keratins were discarded from the final list of identified proteins. Only proteins identified with a minimum of 3 specific spectral counts in the 3 replicates of positive samples and absent from the control samples were further considered.

Expression constructs. Mouse vasohibin-1 (VASH1) and vasohibin-2 (VASH2) cDNAs (accession numbers NM_177354 and NM_144879, respectively) were PCR-amplified and inserted into a home-made CAG promoter-containing vector, that generates proteins with a Flag tag at the N-terminus and with superfolder-GFP (sfGFP (J. D. Pedelacq, S. Cabantous, T. Tran, T. C. Terwilliger, G. S. Waldo, (2006) Nat Biotechnol 24, 79)) and a 6 His tag at the C-terminus (Flag-vasohibin-sfGFP-His). The corresponding control plasmid encodes Flag-sfGFP-His protein. Bicistronic plasmids allowing coupled expression of both vasohibins and SVBP were obtained by introducing, downstream of the Flag-vasohibin-sfGFP-His cDNA, a cassette containing the encephalomyocarditis virus IRES sequence followed by the cDNA encoding mouse SVBP (accession number NM_024462) with a C-terminal Myc-tag (Flag-vasohibin-sfGFP-His/SVBP-Myc). Point mutations were introduced by PCR to generate enzymatically dead versions of vasohibins: C179A for VASH1 and C158A for VASH2, according to the numbering of accession numbers NP_796328 and NP 659128, respectively. The plasmid encoding mouse SVBP with C-terminal Myc and Flag tags (SVBP-Myc-Flag) was obtained from OriGene. Mouse Eb1 cDNA (accession number NM_007896) was inserted into an EGFP-tagged vector in order to generate EB1-EGFP. Plasmid encoding His-EB1 for protein production in *E. coli* was described in (A. Bosson et al., (2012) PloS one 7, e33490), cDNAs coding for human tubulin α1B and mouse tubulin α8 (accession numbers NM_006082 and NM_017379, respectively) were PCR-amplified and inserted into a vector with N-terminal mCherry tag. Point mutations in α-tubulin cDNAs were introduced by PCR to replace the last aromatic residue by an alanine: Y451A for α1B-tubulin and F449A for α8-tubulin, according to the numbering of accession numbers NP 006073 and NP . . . 059075, respectively. Plasmid expressing mouse-specific shRNAs were from OriGene: TL511800B for Vash1. TL506751C for Vash2, TL517601B for Svbp and TR30021 for control. All constructs were verified by DNA sequencing.

Purification of His-tagged vasohibins from HEK293T cells. HEK293T cells cotransfected with plasmids allowing expression of GFP or active/inactive forms of vasohibins and SVBP (Flag-sfGFP-His or Flag-(dead) VASH1/2-sfGFP-His and SVBP-Myc-Flag) were lysed in Tris buffer at pH 8.0, 0.5% TritonX100, 1 mM MgCl2, 200 mM NaCl, 5 mM imidazole in the presence of protease inhibitor cocktail (cOmplete EDTA-free, Roche). After centrifugation (10 min at 16.000 g and 4° C.), supernatants were collected and added onto 20 µl, of cobalt resin (Sigma) and incubated for 3 h at 4° C.:. After 3 washes with lysis buffer, proteins were eluted using 200 mM imidazole, Tris buffer at pH 8.0, 1 mM MgCl2, 200 mM NaCl. Purified proteins were equilibrated by dialysis at 4° C. in 100 mM Pipes, 1 mM EGTA and 1 mM MgCl2 and directly used in radioactivity assays.

Cell culture and transfection. Hippocampal neurons and MEFs were prepared as previously described (C. Erck et al., (2005) Proceedings of the National Academy of Sciences of the United States of America 102, 7853). HEK293T cells were maintained under standard conditions. HEK293T cells were transfected with JetPRIME transfection reagent (Polyplus-Transfection). MEFs and neurons were transfected using Amaxa Nucleofector kits (Lonza). A ratio of 1:1 was generally used for cDNA co-transfections (for VASH1/2 with SVBP, or for mCherry-tubulin with bicistronic plasmids allowing coupled expression of VASH1/2 and SVBP.

Western-blotting and immunofluorescence. Detyrosination activity was detected using antibodies specific for tyrosinated tubulin (YL1/2, Tyr-tub) or native EB1 (Tyr EB1), and C-terminally detyrosinated tubulin (deTyr-tub) or EB1 (deTyr-EB1). Control of total tubulin or EB1 was estimated with antibodies that recognizes both species (total α-tub or α3A1, total EB1 from BD Transduction lab.). All these antibodies were described and characterized in (A. Bosson et al., (2012) PloS one 7, e33490). The other primary antibodies, anti-His, anti-Flag, anti-GFP, anti-turboGFP, anti-mCherry, anti-Tau and anti-ankyrin were from Qiagen, Molecular Probes, Chromotek, invitrogen, Sigma, Millipore and Santa-Cruz, respectively. For Western-blotting, cells were collected after 24 h of transfection. After washing with phosphate-buffered saline (PBS) me¬dium at 37° C., cells were directly lysed in Laemmli buffer. Protein extracts were loaded on 10% acrylamide gels (Mini-PROTEAN® TGX Stain-Free™, Invitrogen) and transferred with Trans-Blot® Turbo (BioRad). Membranes were incubated with primary and secondary antibodies conjugated with HRP and finally revealed with Chemidoc camera (Biorad). For analysis and graphical representations of immunoblots (FIG. 4A), protein bands were quantified from triplicate blots of 3 different experiments using ImageJ software (National institutes of Health, Bethesda, Md.). Detyrosinated α-tubulin signal was normalized to the total protein content of the sample estimated from a stain-free image. For immunofluorescence, cells were generally fixed at 37° C. in 4% paraformaldehyde, 4.2% sucrose, phosphate buffered saline medium (PBS) (except for ankyrin staining for which methanol fixation at 20° C. was used) and permeabilized using 0.1% Triton X-100, PBS. Cells were then incubated with primary antibodies, followed by incubation with secondary antibodies (see below) conjugated with either alexa-488, cyanine-3 or cyanine-5 fluorophores (1:1000). Nuclei were stained using Hoescht 33258 (1 µg/mi).

RT-PCR amplification. Messenger RNAs from cells and tissues were prepared with the Dynabeads purification kit (Invitrogen). RT-PCR were performed with the Superscript One step RT-PCR System (invitrogen) in 12.5 µL with 50 ng RNA. Products of respectively 697, 748 and 154 bp from mouse Vash1, Vash2 and Svbp were amplified at 58° C. by 45 cycles using the following primers: 5'-TACAAACCGCCCGCCTTCC (forward) (SEQ ID No4) and 5'-ACAGACCCTGACAGCTACCAACA (reverse) for Vash1 (SEQ ID No5), 5'-GCAGCCTTCCATTGAGCGGT (forward) (SEQ ID No6) and 5'-CAGT-CAACCCAGGGCTTTGCC (reverse) for Vash2 (SEQ ID No7), 5'-CCAGCAGGAGCTGAAGCAAAGA (forward) (SEQ ID No8) and 5'-GCACCAGTrCCTCTGCCGGG (reverse) for Svbp (SEQ ID No9). GAPDH was amplified at 64° C. by 25 cycles with 5'-TCAACGGGAAGCCCAT-CACCA (forward) (SEQ ID No10) and 5'-GTTTCTCCAGGCGGCACGTC (reverse) primers (SEQ ID No11).

Morphometric neuron analysis. Mosaic images of 2DIV neuron fixed and stained with anti-tubulin antibody were acquired with a 20× N.A 0.5 objective on a DM16000 Leica microscope with a motorized stand. Images were segmented after enhancement with a DoG filter. The cell bodies of single neurons were manually selected and used to process neurons individually with an homemade AutoNeuriteJ macro. Briefly the neuron images were skeletonized and neuritic loops were resolved using the "Analyze Skeleton 2D/3D ImageJ plugin" (I. Arganda-Carreras, R. Fernandez-Gonzalez, A. Munoz-Barrutia, C. Ortiz-De-Solorzano, (2010) Microsc Res Tech 73, 1019). The ends of neurites were marked using the "BinaryConnectivity" image) plugin (developed by G. Landini, www.mecourse.com/landinig/software/software.html). Images of each neurite from their ends to the cell body were produced. Among the neurites with a path overlap, the longest was defined as primary neurite. The images of primary neurites were subtracted to images of overlapping neurites, thus defining secondary neurites and number of branching. Neurite lengths were measured. Neurites with a length inferior to 12 µm were not considered in order to avoid skeletonization artifacts. An axon was defined among primary neurites of a single neuron if its length was at least 48 µm and 1.3-times longer than any other primary neurite. Using this macro we selected a minimum of 27 neurons for each condition and compared the mean axonal length, mean primary neurite number and branching frequency.

In utero electroporation, tissue processing, immunohistochemistry and analyses. A full description is available in (M. Barnat, J. Le Friec, C. Benstaali, S. Humbert, (2017) Neuron 93, 99). Briefly, embryos from anesthetized timed-pregnant mice were electropored at E14.5 with plasmids allowing expression of shRNAs (see above). Four days later (E18.5), embryonic brains were dissected, fixed, cryosectioned and placed onto slides for analyses. Anti-tGFP primary antibodies (1:300) was incubated overnight at 4° C. Nuclei were counterstained with DAPI (Roche). Images were acquired with a 20× N.A 0.5 objective on a DM16000 Leica microscope with a motorized stand and analyzed with Image J. The cortical region where transfected cells were detected was divided into 6 bins of equal surface in which GFP positive (GFP+) neurons were counted (5 embryos per condition, 3 slides per embryo). At least 260 GFP+neurons were counted per embryo.

Results:

To enrich for TCP, a three step purification procedure using taxol-stabilized radiolabelled tyrosinated microtubules as a substrate to follow activity was designed. A typical procedure gave a final purification factor of nearly 400-fold (FIG. 1A). The last fraction (IV) was able to cleave the C-terminal tyrosine from tubulin incorporated in microtubules but not from EB1. EB1 is a protein that shares a similar C-terminal sequence with α-tubulin (QEEY (SEQ ID NO:15) instead of -GEEY (SEQ ID NO:16)) and is generally not a substrate for TCP in physiological contexts (A. Bosson et al., (2012) PloS one 7, e33490).

To isolate the protein(s) responsible for TCP activity from fraction 1V, it was reasoned that an irreversible inhibitor could be used as in other chemical proteomic studies (M. A. Child et al., (2013) Nat Chem Biol 9, 651). First the sensitivity of brain TCP to various commercial protease inhibitors was tested. The activity was inhibited by several serine/cysteine protease inhibitors (AEBSF, TLCK, TPCK, E-64, parthenolide) and by the thiol-reactive compound N-Ethylmaleimide (FIG. 1B). These results, in agreement with prior studies (X. Fonrose et al., (2007) Cancer Res 67, 3371), strongly suggested that the catalytic activity of the putative TCP depends on a catalytic cysteine.

Although E-64 only showed modest inhibitory activity (IC50 around 300 PM, FIG. 1B), this natural product is an ideal starting point for inhibitor design because its reactive epoxide electrophile can display a peptide or amino acid mimicking native protein C-terminus. Furthermore, parthenolide, a compound widely used to down-regulate detyrosination levels in cells (4, 6, 9, 10) contains an epoxide function which was shown essential to its cellular effect (X. Fonrose et al., (2007) Cancer Res 67, 3371). Three inhibitors, epoY, epoEY and epoEEY, which contain the epoxide coupled to one, two or three amino-acids from the α-tubulin C-terminus were thus synthesized. EpoY was found to be the most potent inhibitor of the TCP activity (IC50 around 500 nM, FIG. 1B). An analog of epoY (alkyne-epoY) that could be used for purification of labeled targets using click chemistry to an affinity tag was therefore synthesized. Alkyne-epoY retained a strong inhibitory potency (FIG. 1B) and irreversibly inhibited the enriched enzyme activity. Probe labeling of fraction IV with alkyne-epoY (or the control epoY) followed by a click reaction to attach an azide TAMRA red-fluorescent dye was performed (FIG. 11D). Labeling showed specific modification of a small number of proteins around 50 kDa (FIG. 1E). To identify these inhibitor targets, fraction IV was pre-treated with either alkyne-epoY or epoY as control, the labeled proteins were isolated and the proteins covalently attached to the beads analyzed by mass spectrometry (FIG. 1D). The results from three independent experiments identified the protein vasohibin-1 (VASH1) as the most likely TCP candidate (Table 2). Peptides covering the almost full VASH1 sequence were detected only in the alkyne-epoY treated samples. Recent bioinformatics data show that Vasohibin-1 and its homologue vasohibin-2 (VASH2) possess a non-canonical Cys-His-Ser catalytic triad and are previously undetected members of the transglutaminase-like cysteine proteases family (L. Sanchez-Pulido, C. P. Ponting, (2016) Bioinformatics 32, 1441). (FIG. 1F).

has a chaperone-like function (Y. Suzuki et al., (2010) Journal of cell science 123, 3094). Consequently, the ability of VASH proteins to detyrosinate α-tubulin in cells in the absence or presence of SVBP was examined. Expression of vasohibins alone in HEK293T cells resulted in a slight increase of detyrosinated tubulin, whereas expression of either protein with SVBP resulted in a substantial increase in detyrosinated tubulin corresponding to a nearly complete loss of endogenous tyrosinated tubulin. Importantly, mutation of the putative catalytic cysteine on vasohibins (C179A for VASH1, and C158A for VASH2 (L. Sanchez-Pulido, C. P. Ponting, (2016) Bioinformatics 32, 1441)) abolished their capacity to produce detyrosinated tubulin. Similarly, in murine embryonic fibroblasts (MEF), expression of the vasohibins with SVBP resulted in complete detyrosination of endogenous α-tubulin (FIG. 2A).

Alpha-tubulins are generally encoded with a C-terminal tyrosine preceded by two glutamates. Alpha4-tubulin lacks however the C-terminal tyrosine and α8-tubulin contains a C-terminal phenylalanine residue. Moreover, phenylalanine can be incorporated in place of tyrosine in tubulin and be a possible cause of neuronal dysfunction (Y. Ditamo, Y. M. Dentesano, S. A. Purro, C. A. Arce, C. G. Bisig, (2016) Scientific reports 6, 38140). The substrate specificity of the vasohibins by overexpressing α1B- and α8-tubulin together with VASH1 or VASH2 and SVBP in HEK293T cells was therefore tested. Both tubulin isotypes were cleaved by active vasohibins when expressed with SVBP (FIGS. 2B, 2B). Vasohibins were however unable to cleave the C-terminal residue when tyrosine was mutated to alanine (FIGS. 2B, 2B), confirming the specificity of VASH proteins for C-terminal tyrosine and phenylalanine residues.

To further confirm the catalytic function of vasohibins and the nature of their interactions with SVBP, they were overexpressed in HEK293T cells in the absence or presence of SVBP and the resulting complexes were purified using a cobalt resin. SVBP co-purified with both vasohibins as expected from previous affinity measurements, (KD 30-90 nM (Y. Suzuki et al., (2010) Journal of cell science 123, 3094)), and complex formation was not dependent on catalytic activity (FIG. 6A). Importantly, the two protein complexes efficiently catalyzed tubulin detyrosination while complexes containing the catalytic dead versions of the vasohibins were unable to detyrosinate tubulin (FIG. 2C). Both complexes more rapidly cleaved microtubules compared to tubulin dimers (FIG. 2D, 6), consistent with the reported specificity of brain TCP (H. S. Barra, C. A. Arce, C. E. Argarana, (1988) Molecular neurobiology 2, 133; G. G. Deanin, S. F. Preston. R. K. Hanson, M. W. Gordon, (1980) Eur J Biochem 109, 207); N. Kumar, M. Flavin. (1981) The Journal of biological chemistry 256, 7678). Purified VASH1/

TABLE 2

| Fraction | Purification step | Volume (ml) | Protein amount (mg) | Total activity (µmole) | Specific activity (µmole/mg) | Purification (fold) | Yield (%) |
|---|---|---|---|---|---|---|---|
| I | Brain homogenate | 70 | 336.56 | 1.41 | 0.004 | — | 100 |
| II | Ammonium Sulfate | 7 | 39.35 | 3.77 | 0.096 | 23 | 267 |
| III | Q sepharose | 20 | 15.03 | 3.17 | 0.211 | 51 | 225 |
| IV | SP sepharose | 6 | 0.09 | 0.14 | 1.533 | 368 | 10 |

Vasohibin proteins (41-42 kDa) have been extensively characterized as angiogenesis regulators but are still poorly understood on a molecular level (Y. Sato, (2013) Journal of biochemistry 153, 5). Recent studies identified SVBP (Ccdc23) as a high affinity binding partner of vasohibins that SVBP complex was not able to cleave the C-terminal tyrosine from EB1 indicating its clear tubulin preference, whereas, intriguingly VASH2/SVBP complex was able to partially detyrosinate EB1 in the same conditions (FIG. 2E). In most cell types, including neuronal-derived, C terminal tyrosine cleavage was shown restricted to tubulin (H. S. Barra, C. A. Arce, C. E. Argarana, (1988) Molecular neurobiology 2, 133; A. Bosson et al., (2012) PloS one 7, e33490). EB1 can however be detyrosinated in specific endothelial and tumor cells (A. Rovini et al., (2013) PloS one 8, e65694) and this may be related to their VASH2 contents or defect in a regulatory mechanism.

Figure 3D:
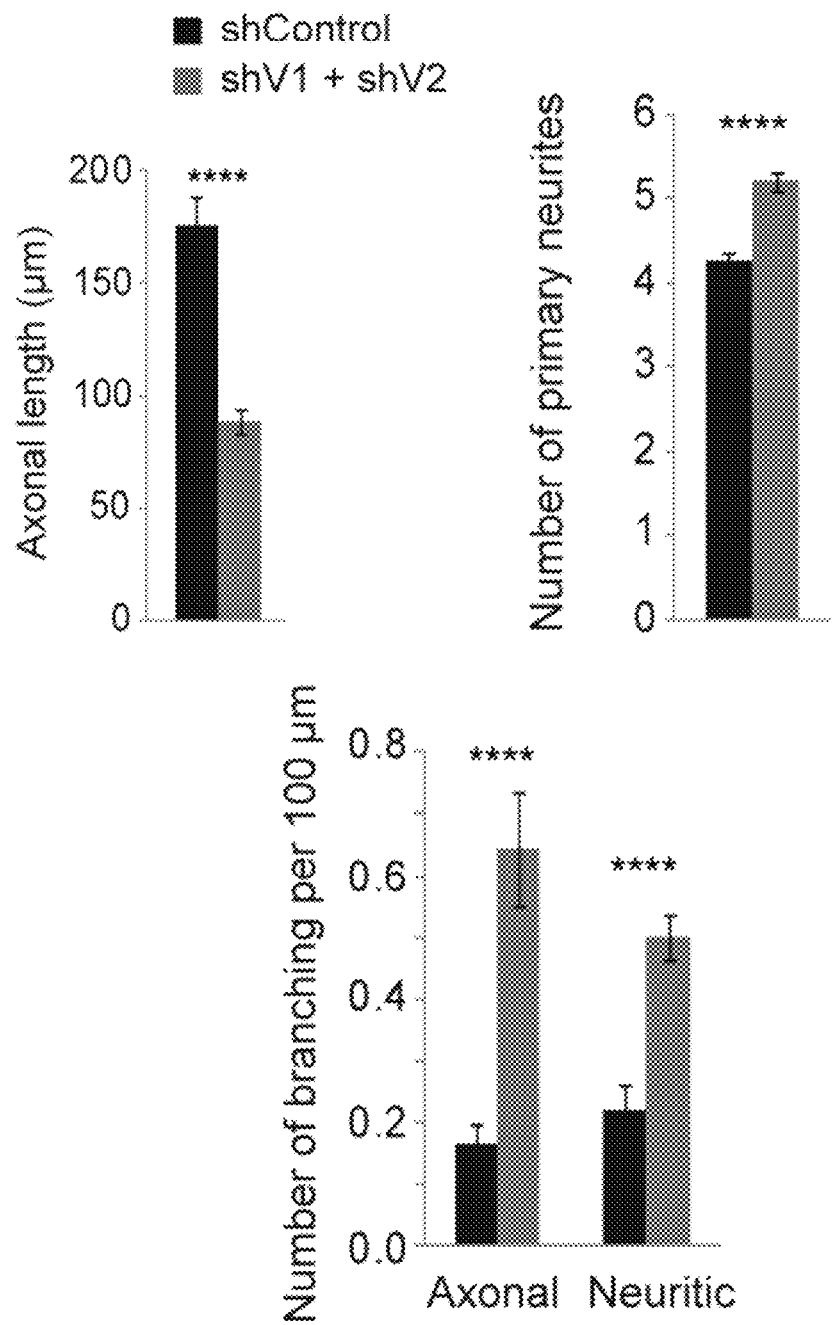
Figure 5A:
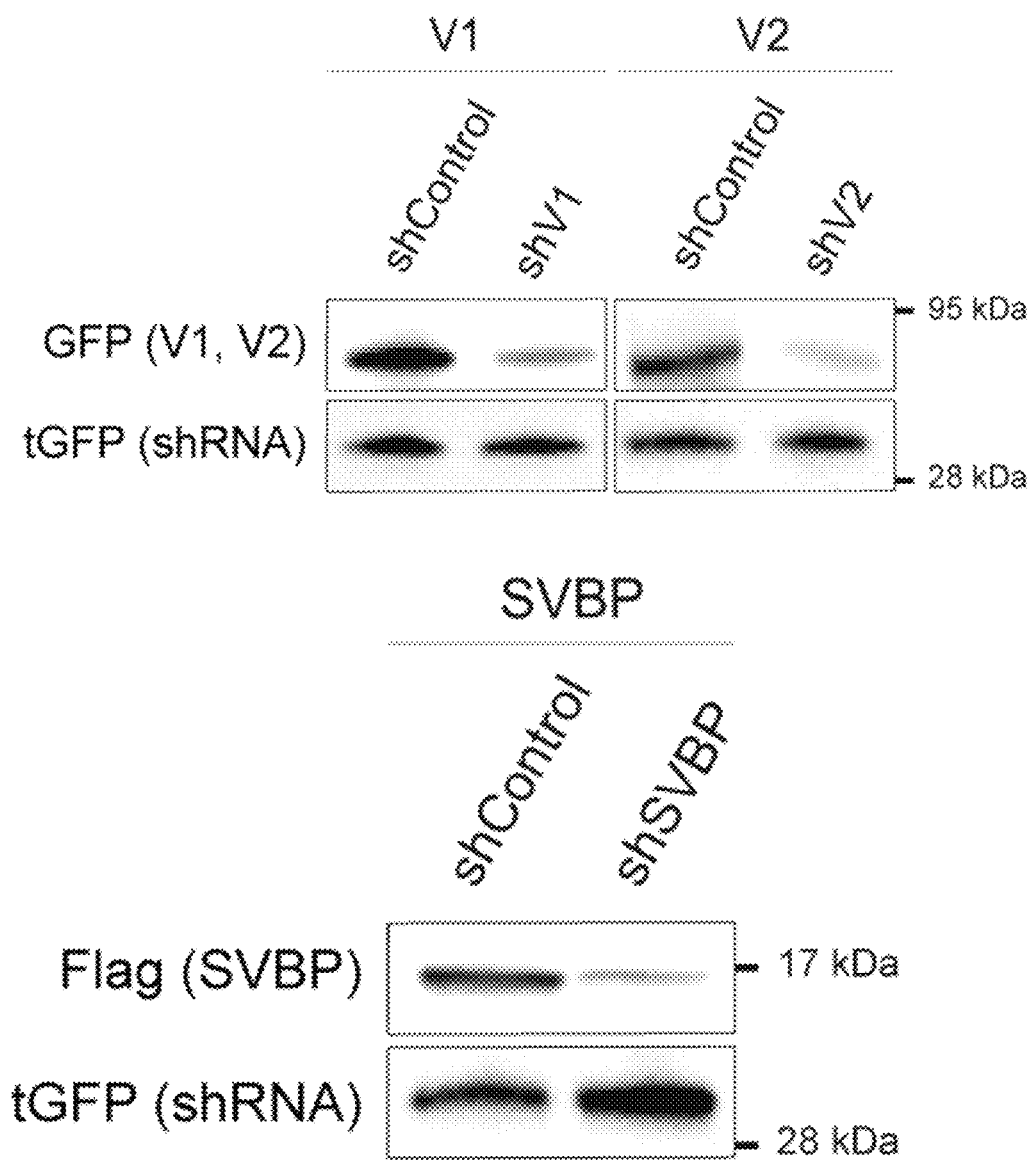
Figure 5B:
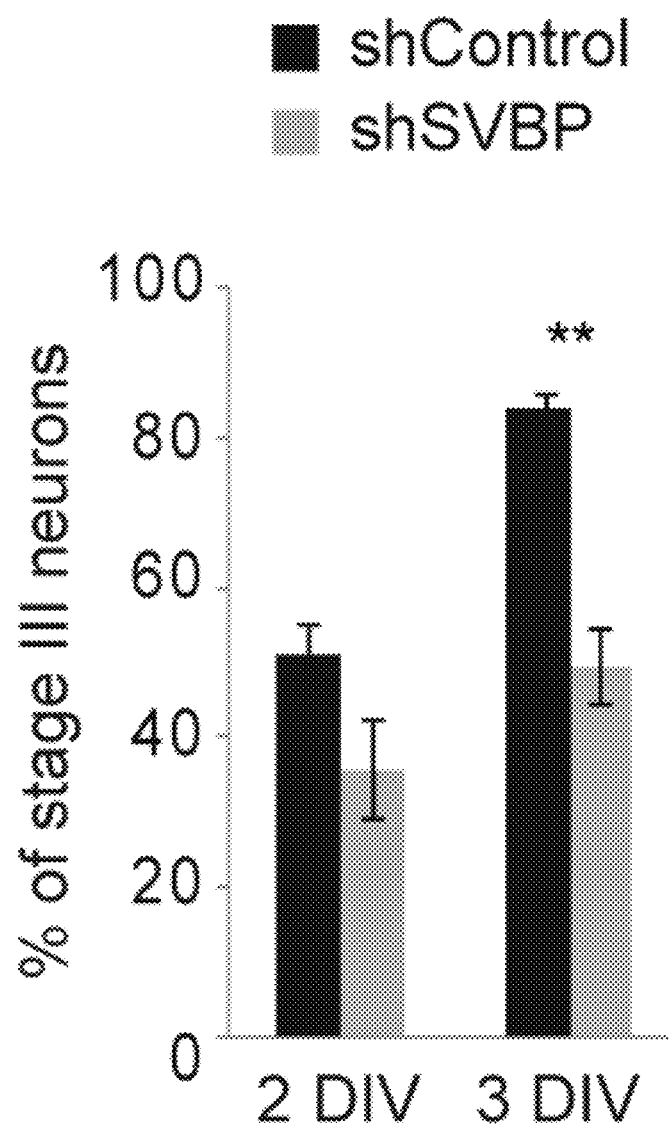
Figure 5C:
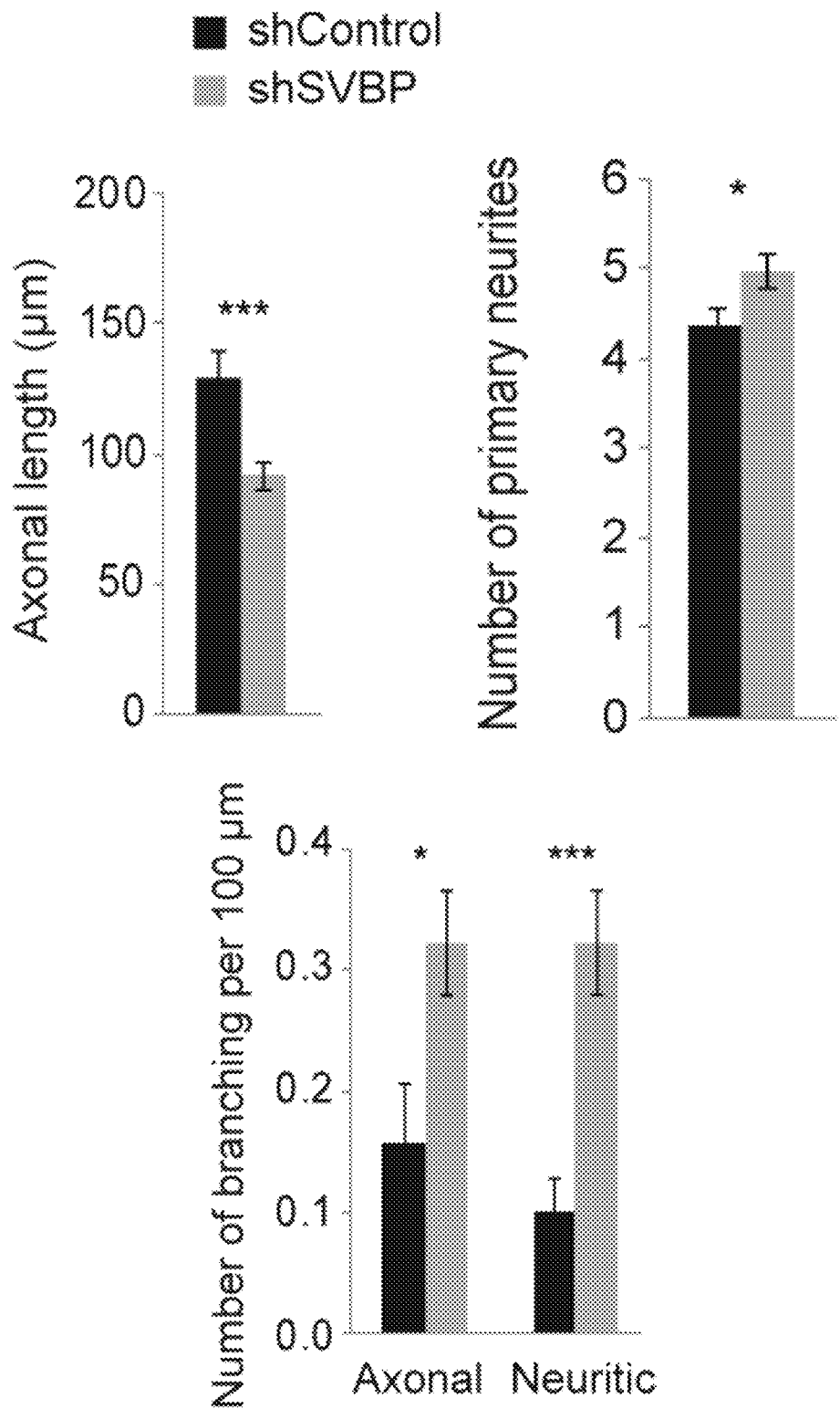

To confirm the functional significance of vasohibins and their role in α tubulin detyrosination, we assessed the phenotypic effects of knocking down expression of these proteins in differentiating neurons where the de/tyrosination cycle is highly important for growth cone pathfinding and axon differentiation, i. e, for neuron polarization (C. Erck et al., (2005) Proceedings of the National Academy of Sciences of the United States of America 102, 7853; Y. Konishi. M. Setou, (2009) Nat Neurosci 12, 559; S. Marcos et al., (2009) PloS one 4, e5405). Although it was not possible to detect vasohibins and SVBP by Western-blot in mouse neurons using commercial antibodies, their transcripts were amplified from RNA preparations of cultured hippocampal neurons as well as of adult and embryonic mouse brain tissues (FIG. 3A). Hippocampal neurons with plasmids expressing short hairpin RNAs (shRNAs) targeting either the vasohibins or SVBP, as well as control shRNA were transfected (FIG. 5A). Western-blot analysis showed that the levels of detyrosinated α-tubulin were almost decreased by 50% when either the two vasohibins or SVPB were downregulated, demonstrating their significant role in detyrosination of neuronal microtubules (FIG. 3B). The remaining pool of detyrosinated α-tubulin in the knock downs is likely due to the presence of α4-tubulin, which genetically lacks the C-terminal tyrosine and remains in detyrosinated form in the brain (V. Redeker, (2010) Methods Cell Biol 95, 77). Confocal images of neurons cultured 2 days in vitro (2DIV) confirmed a decrease in the levels of the native detyrosinated α-tubulin upon reduction of vasohibins expression. The remaining detyrosinated pools are specifically concentrated in the axon, while α-tubulin in neurites appears highly tyrosinated. A morphometric analysis indicated that vasohibins down-regulation led to a clear delay in axonal differentiation, as shown by a reduced proportion of stage Ill cells (having an axon) both at 2DIV and 3DIV (FIG. 3C). Tau and ankyrin staining of neurons bearing an axon confirmed normal distribution, with Tau highly expressed in axon shaft at 3DIV and ankyrin in the axon initial segment at 10DIV. Interestingly, 2DIV neurons knocked down for vasohibins develop an increased number of neurites and branches with overall reduced axon length (FIG. 3D). A delay of axon differentiation and similar morphological anomalies were observed when down-regulating SVBP (FIG. 5B-C). Thus, contrary to the premature axonal differentiation observed in the absence of the reverse enzyme TTL (C. Erck et al., (2005) Proceedings of the National Academy of Sciences of the United States of America 102, 7853), here a clear delay of axon differentiation when down-regulating vasohibins or SVBP was observed.

The functional significance of vasohibins in vivo in mouse brain was next tested by focusing on the cerebral cortex where the de/tyrosination cycle is critical for the neocortex layer organization (C. Erck et al., (2005) Proceedings of the National Academy of Sciences of the United States of America 102, 7853). During corticogenesis neuronal migration relies in part on neuron polarization which we showed is highly dependent on vasohibins and SVBP (FIG. 3C). E14.5 embryos were electroporated with the plasmids expressing shRNAs targeting the vasohibins as well as control shRNA, and radial neuronal migration analyzed four days later, validated shRNAs that suppressed approximately 50% of detyrosinated α-tubulin pools in cultured neurons were used. At E18.5, most neurons from control brains have reached the upper layer (bin 1), whereas in the absence of vasohibins a significant fraction of neurons failed to do so (FIG. 4A-B). Thus these enzymes have a crucial role in neuronal migration during brain cortex development.

Overall these results indicate a critical role of the vasohibins and of their associated partner SVBP in neuron and brain, and further support that they are tubulin carboxypeptidases.

TCP remained the crucial missing element of the α-tubulin de/tyrosination cycle for 40 years. Vasohibins were identify as enzymatic proteins that perform the TCP function (FIG. 7) and their interacting partner SBVP is essential for their activity. We reveal the critical involvement of vasohibins and SVBP in neuronal differentiation and brain cortex development, and describe a new inhibitor targeting this family of enzymes that could be used for further functional studies of vasohibins. The failure of prior attempts to identify TCPs most probably resulted from the essential association of vasohibins with SVBP for stability and activity which could likely be lost during standard purification assays. In agreement with TCP functions, vasohibins are widely distributed in eukaryotes, have broad tissue expression, and vasohibin-1 (which is generally more expressed than vasohibin-2) is abundant in brain, heart and kidney (L. Sanchez-Pulido, C. P. Ponting, (2016) Bioinformatics 32, 1441: S. Nimmagadda et al., (2007) Dev Dyn 236, 1358: T. Shibuya et al., (2006) Arteriosclerosis, thrombosis, and vascular biology 26, 1051) (see also GTEx Portal on www.gtexportal.org/home/). Identification of the elusive TCP activity should now provide an understanding, at the molecular level, of the relationship between α-tubulin detyrosination and cellular microtubule stability (L Paturle-Lafanechere et al., (1994) Journal of cell science 107 (Pt 6), 1529; D. R. Webster, G. G. Gundersen, J. C. Bulinski, G. G. Borisy, (1987) Proceedings of the National Academy of Sciences of the United States of America 84.9040).

Interestingly, vasohibins were shown to be critical for cell and tissue integrity and defects in these proteins were associated with cancers (R. Norita et al., (2017) Cancer science 108, 419), as would be expected for enzymes that regulate microtubule stability through detyrosination. Overall, the discovery of TCPs provides valuable information to unravel the function(s) of the cycle of de/tyrosination, and its impact on health and disease.

Example 2: Detyrosination Status in Human Brain from Healthy and AD Patients

1 Rationale.

The amounts of tyrosinated, detyrosinated and Δ2-tubulin (another form of detyrosinated tubulin) were analyzed by immunoblotting in brains of Alzheimer disease and control patients. They were analyzed at different Braak stages of the pathology and compared to corresponding control samples of healthy brains. For each sample 4 brain regions (entorhinal cortex, hippocampus, temporal and frontal cortex) were analyzed.

2 Material and Methods

Tissues. Human tissue samples consist of 4 regions of brain (entorhinal cortex, hippocampus, temporal cortex, lateral prefrontal cortex) coming from a panel of 29 male and female patients aged from 52 to 93 years: 11 controls, 5 Braak stadium 1-11, 6 Braak stadium III-IV and 7 Braak stadium IV-V (see annex 1 for details).

Extracts preparation. Human brain samples were homogenized 2×30 seconds at room temperature in (10 vol/w) 10 mM Tris, 0.32M sucrose, pH=7.4 containing complete inhibitors cocktail (Roche) using ready to use Precellys Lysing Kit (Bertin Technologies) in a Minilys apparatus. After lysis, the homogenates were collected, frozen in liquid nitrogen and then stored at −80° C. until use (referred as homogenate brain stock). When needed, frozen aliquots were diluted v/v with RIPA buffer (50 mM Tris, 150 mM NaCl, 1% NP40, 0.5% deoxycholate, 0.1% SDS, pH1=8) stirred 30 min at 4° C. and then centrifuged 10 min at 12000 rpm, 4° C. Supernatants were frozen in liquid nitrogen and then stored at −80° C. until use.

Antibodies. Polyclonal anti-detyrosinated (anti-deTyr) and anti-Δ2 tubulin antibodies were homemade (Bosson et al., 2012; Paturle-Lafanechere et al., 1994).

Immunoblots.

The samples of 4 regions of 29 patients end up with 116 samples to be analyzed. Each sample has been analyzed in triplicates. RIPA supernatants (10 µl of a 1/4 dilution of frozen samples) were subjected to electrophoresis on stain free 4%-15% gels (Bio Rad) and then quickly transferred to nitrocellulose membrane using Trans-Blot Turbo Transfer System (Bio Rad). Blots were revealed using specific antibodies against detyrosinated and Δ2 tubulin at 1/20000. The polyclonal α3A1 antibody was used at 1/10000 dilution to detect total α-tubulin. The appropriated peroxydase labeled secondary antibodies were used at 1/20000. Blots were revealed using Pierce ECL Western blotting substrate (Thermo scientific) and analyzed with ChemiDoc™ MP Imaging System (Bio Rad) using Image Lab software for quantification.

3 Results

The results are shown in FIG. 8.

These results clearly show a progressive accumulation of detyrosinated and Δ2 tubulin forms in all regions of Alzheimer brains as compared to control brains (no effect of brain region).

Example 3: In Vivo Function of VASH1, VASH2 and SVBP on Detyrosination of Microtubules Material & Methods;

Brain Tissue Preparation for Biochemical Analysis:

Hippocampus were homogenized in a lysis buffer (phosphate buffer saline (PBS) without CaCl2 and MgCl2, 14190-094 Life Technologies) supplemented with protease (P8340, Sigma) and phosphatase inhibitor cocktails (P5726 and P0044, Sigma) at 150 mg/mL, using a Precellys apparatus homogenizer (2×20 s, 5000 rpm). Lysates were then centrifuged at 21,000 g for 20 minutes at 4° C. The resulting supernatants were collected and protein concentrations were determined using bicinchoninic acid assays (Pierce/Thermo Fisher Scientific). Samples were stored at −80° C. until analysis.

Capillary Western Blotting by Wes™ and Peggy Sue™ Simple Western for Brain Samples Tyrosinated, detyrosinated, delta 2 tubulins, total α-tubulin and tubulin tyrosine ligase levels were assessed using an automated Simple Western system (Protein Simple) in lysates of hippocampus from SVBP, VASH1 and VASH2 KO wild type, heterozygous and homozygous mice. All procedures were performed with manufacturer's reagents, except for primary antibodies described in the table 1, according to the user manual. Samples were loaded at a protein concentration of 0.125 µg/µL, incubated with primary antibodies for 60 min and secondary anti-mouse or anti-rabbit IgG for 30 min. Data were analysed with Compass software (Protein Simple). Protein levels were normalized in the GAPDH level.

TABLE 1 antibodies characteristics

| | Dilution | Providers |
|---|---|---|
| Tyrosine tubulin | 1:50 | T9028, Sigma |
| Total α-tubulin | 1:200 | T6199, Sigma |
| GAPDH | 1:50 | 7074S, Cell Signaling |
| Delta 2 tubulin | 1:150 | ab106658, Abcam |
| Detyrosinated tubulin | 1:50 | ab48389, Abcam |
| Tubulin tyrone ligase | 1:25 | 66076-Ig, Proteintech |

Protein Extraction from Heart Ventricles and Western-Blot:

Proteins from cardiac ventricles (around 50 mg) were homogenized in Precellys tube (KT03961-1-007.2) with FastPrep homogenizer for western blots in Protein extraction Buffer (Cellsignaling; 9803S) in the presence of protease (Roche; 04906837001) and phosphatase inhibitors (Roche; 11836153001). Equal amounts of proteins (30 µg) were separated on 12% Bis Tris SDS-polyacrylamide gel electrophoresis (Bio-Rad; 3450119) and transferred to nitrocellulose membranes with TransBlot system (Bio-Rad; 170-4159). Proteins were detected with the primary antibodies against GAPDH (1/10000, Millipore; MAB374), α-tubulin (1/5000, Sigma; T6199-200 µL), tyrosinated-tubulin (1/1000, Abcam; ab6160), detyrosinated-tubulin (1/1000, Abcam; ab48389), delta2-tubulin (1/1000, Abcam; ab106658) followed by infrared dyes-conjugated secondary antibodies (from 1/1000 to 1/10000, Li-Cor). Protein quantification was obtained by densitometry analysis using an Odyssey scanner and normalized to Gapdh levels.

Mice. SVBP, VASH1 and VASH 2knockouts were generated in mice by CRISPR/Cas9 gene editing (see Teixera et al 2018 for VASH1 KO generation). A sequence in exon 2 was targeted for SVBP, a sequence in exon 1 for VASH1 and a sequence in exon 2 for VASH2. F0 mosaic animals born after reimplantation of microinjected embryos were genotyped by PCR/Sanger sequencing and then mated to C57BL/6 mice to provide at least F4/F5 mice.

Results:

In order to confirm in viva the function of vasohibin1, vasohibin2 and SVBP on the detyrosination of microtubules, we measured tyrosinated tubulin, detyrosinated tubulin, delta 2 tubulin, total α-tubulin and tubulin tyrosine ligase levels in knock down transgenic mice (wild type, heterozygous and homozygous) for either vasohibin1, or vasohibin2 or SVBP proteins. This study was performed on brain (hippocampus) and heart (ventricle) from mice generated at Grenoble Institute for Neuroscience.

In brain samples from VASH1 KO homozygous mice, the levels of detyrosinated tubulin and delta 2 tubulin were decreased (FIG. 9C. D) whereas those for tyrosinated tubulin were increased (FIG. 98). The same but more potent effects were observed in SVBP KO homozygous mice (FIG. 10B,C,D). On the contrary no effects were observed in VASH2 KO homozygous mice (FIG. 11B,C,D).

In cardiac ventricles samples the levels of detyrosinated tubulin and delta 2 tubulin were decreased for VASH1 KO homozygous mice (FIGS. 12C,D) and SVBP KO homozygous mice (FIG. 13C,D) whereas those for tyrosinated tubulin were increased for VASH1 KO homozygous mice (FIG. 121). As for brain samples no effects were seen in cardiac ventricles samples from VASH2 KO homozygous mice (FIG. 14B,C,D).

As anticipated de-tyrosinated tubulin levels were decreased in VASH1 and SVBP KO homozygous mice whereas tyrosinated tubulin levels were increased either in brain samples or cardiac ventricles. The decrease of de-tyrosinated tubulin is due to the lack of VASH1 in VASH1 KO homozygous mice whereas in SVBP KO homozygous mice the VASH1 is no more active due to the lack of SVBP which plays the role of chaperone for VASH1 and VASH2 and stabilize these two proteins. There were no statistical differences in VASH2 KO homozygous mice probably due to the fact that VASH2 levels of expression are lower than those of VASH1 in the brain. No statistical difference were observed with KO heterozygous mice whatever the protein probably due to a compensatory effect which was settled down since birth and/or a level of activity of the remaining protein sufficient to do the detyrosination.

The de-tyrosinated tubulin levels decrease confirms the physiological function of VASH1 and SVBP but more importantly the concomitant increase of tyrosinated tubulin which is crucial for microtubule dynamicity and functions is in favor of TCP inhibitors to treat neurodegenerative diseases in which microtubule function are altered.

Example 4: Relationship Between the Level of Tyrosinated Tubulin and Dendritic Spines Density (a Cognitive Marker) in a Cellular Model of AD 1 Rationale.

Our hypothesis is that accumulation of detyrosinated microtubules might lead to a loss of microtubule dynamicity which is deleterious for synaptic plasticity and which may contribute to the dendritic spine and synaptic loss characterizing early stages of AD.

Spine shape (stubby, thin, mushroom) and number are strongly correlated with synaptic efficacy and cognitive abilities. Exposure of hippocampal neurons to Aβ oligomers (chronic exposure) is known to induce a strong reduction of dendritic spines density (Hsieh et al., 2006).

To test our hypothesis we have analyzed dendritic spines density and morphology in WT, VASH1, VASH2 and SVBP knockout mature hippocampal neurons in the presence or absence of AP oligomers.

The amounts of the different forms of tubulin (tyrosinated, detyrosinated, Δ2-tubulin) were analyzed in mature neurons from wild type (WT), VASH1 and SVBP deficient mice (heterozygotes and KO animals).

2 Experimental Strategy.

Mice. SVBP, VASH1 and VASH2 knockouts were generated in mice by CRISPR/Cas9 gene editing (see Teixera et al 2018 for VASH1 KO generation). A sequence in exon 2 was targeted for SVBP, a sequence in exon 1 for Vash1 and a sequence in exon 2 for Vash2. F0 mosaic animals born after reimplantation of microinjected embryos were genotyped by PCR/Sanger sequencing and then mated to C57BL/6 mice to provide at least F4/F5 mice.

Neurons. Hippocampal or cortical neurons were dissected from WT, SVBP-, VASH1- and VASH2-KO E17 embryos and cultured as previously described (Erck et al 2005).

Analysis of dendritic spines. A small proportion of hippocampal neurons (1%) were infected with GFP lentivirus (MOI 100), mixed with non-infected cells and plated onto polyLysine coated dishes at high density (50.000-cells/cm$^2$). Neurons were then maintained in MACs medium containing B27 at 37° C. and 5% CO2. After 15 days in vitro (15DIV), neurons were incubated with 100 nM Aβ oligomers (prepared as described in (Frandemiche et al.) or with DMSO (control). Neurons were fixed at 17DIV and stained with anti-GFP antibodies. Dendritic spines were identified as GFP-labelled dendritic protrusions. Serial images were acquired by confocal microscopy with a Z interval of 200 nm and dendritic spine density and morphology analysis was performed using NeuronStudio.

Neuronal protein extracts. Extracts from cortical neurons were collected at 17DIV. After washing with phosphate-buffered saline (PBS) medium at 37° C., cells were directly lysed in Laemmli buffer. Samples were stored at −20° C. until analysis.

Immunoblots. Each neuronal extract has been analyzed in triplicates. Neurons extracts (n=3 embryos) were analyzed as human samples except that PVDF membrane were employed and antibodies were used as follow: GAPDH antibody (Sigma, 1:5000), YL1/2 (1/10000), anti-deTyr (1/10000), anti-Δ2 (1/10000), and peroxydase labeled secondary antibodies (1/10000).

Results.

The results are shown in FIGS. 15 and 16.

The data clearly show an increase of tyrosinated tubulin and decrease of detyrosinated and Δ2-tubulin in both SVBP and VASH1 knockout cells. Neurons from heterozygotes were not significantly different from wild type neurons. Exposure of wild type neurons to toxic AD induces a strong reduction (30%) of spines density, especially the mature forms (mushroom). When SVBP, or VASH1, or VASH2 are deleted, the spine density and mushroom content of neurons is not sensitive to AP exposure, demonstrating that a reduction of the detyrosination (increased level of tyrosinated tubulin) is protective from Aβ toxicity.

Example 5: Implication of VASH/SVBP Complexes in Regenerative Process

1—Rationale:

Neurons with cell bodies located in the dorsal root ganglia (DRG) are pseudo-unipolar and possess a single axon that bifurcates into two axons, a peripheral axon able to regenerate when injured and a central axon entering the central nervous system, not able to regenerate after injury. It has been shown that injuring the peripheral axons leads to regenerative processes (molecular, cellular) in the central branch as well, meaning that central axons of these DRG neurons are able to regenerate if the corresponding peripheral axons are also injured (Richardson and Verge, 1987). This effect is called conditioning lesion effect or preconditioning. A conditioning lesion induces the enhancement of the intrinsic regenerative capacity in neurons, leading to the enhancement of neuritic growth (Smith and Skene, 1997). We assayed the growth ability of DRG neurons either WT or SVBP KO after a preconditioning protocol.

2—Material and Methods

Adult (2 months) WT and SVBP KO adult mice were surgically conditioned by 30 seconds forceps crushing of their left sciatic nerve (preconditioned condition). 3 day after, neurons of DRG corresponding to those forming the sciatic nerve were then cultured and compared to contralateral DRG neurons (control condition).

Culture procedure consist on 4° C. PBS intracardiac perfusion of mice of each genotypes under Dolethal® overdose in order to remove blood. L4-LS-L6 DRG were dissected, then chemically (Collagenase A and Trypsin) and mechanically dissociated before being plated on poly-L-lysin/laminin coated coverslips with Neurobasal-A culture media (complemented with L-Glutamine. B27 and Penicillin/Streptomycin). Neurons where fixed after 16 h of culture. Immunolabeling of total α-tubulin is performed in order to visualise overall neurons morphologies. Quantification of neuritic sizes were done by homemade automatized ImageJ macro (Aillaud et al., 2017).

3—Results

Results am shown on FIG. 17.

Our Data Indicate that a Reduction of the Detyrosination (and Increased Level of Tyrosinate Tubulin) Via SVBP Deletion Promotes the Regenerative Abilities of DRG Neurons.

Example 6: Analysis of TCP Inhibitors Using an ELISA Method with an α-Tubulin C-Terminal Peptide 1 Rationale.

TCPs or VASH/SVBP complexes are enzymes that cleave the C-terminal tyrosine of a tubulin on microtubule or free dimers of tubulin (Aillaud et al., 2017). We tested their ability to detyrosinate a peptide corresponding to the C-terminal sequence of α tubulin and the effect of several potential inhibitors on this activity. Such assay could be adapted for the screening of large sets of drugs.

2 Material and Methods.

A plate-based assay technique was designed for detecting and quantifying detyrosination activity of VASH/SVBP complex. Briefly, assays were performed on 96 well Immulon 4HBX plates coated with neutravidine at 50 μg/ml in phosphate buffered saline medium (PBS). After rinsing with 0.05% Tween in PBS, the biotinyl-V-15-Y peptide (Biotinyl-Val-Asp-Ser-Val-Glu-Gly-Glu-Gly-Glu-Glu-Glu-Gly-Glu-Glu-Tyr) (SEQ ID NO:14) was coated on plate at $10^{-8}$ M in PBS followed by rinsing with Tween 0.05% in PBS. VASH/SVBP enzyme (0.2 μM), pre-incubated 2 hours at 0° C. with DMSO or inhibitor at varying concentration, was then added for a 30 min reaction onto the peptide. The reaction was stopped by 3 rinsing with 0.05% Tween in PBS. Immunodetection was then performed using anti-tyrosinated tubulin (YL1/2, 1/2000) as primary antibody, anti-rat HRP (1/5000) as secondary antibody, and with TMB solution as HRP substrate for ELISA (Sigma) on a PIERAstar system (BMG Labtech).

Ni-NTA columns (HiTrap 5 ml)

VASH1 was co-expressed with SVBP having a 6 histidine tag on its C-terminus in *E Coli*. The complex was purified on Ni-NTA columns followed by size exclusion chromatography.

3 Results

The results are shown on FIG. 18.

The Data Clearly Show that the Biotinyl-V-15-Y Peptide is a Substrate of VASH/SVBP Enzymatic Complex and Thus Usable to Screen Inhibitor of Activity.

Example 7: Cell Free Assay for Studying the Activity of TCP Inhibitors

Studying Tubulin Carboxypeptidase (TCP) or Tubulin-Tyrosin Ligase (TTL) by RapidFire®/Mass Spectrometry (MS) offers numerous advantages over other existing assay formats. First, the system circumvents the costs and special handling procedures required when using radioactive substrates. Second, RapidFire®/MS based assays do not involve secondary or coupled reactions that can complicate data interpretation. Third, because the peptide species are measured directly by MS, there is no need for fluorescent tags which can cause data artifacts.

Two peptides were used to monitor the enzyme activities. The first one represents the substrate of TTL enzyme or the product of reaction of TCP: Biotinyl-V-D-S-V-E-G-E-G-E-E-E-D-E-E (SEQ ID NO: 12). The second peptide represents the product of reaction with TTL or the substrate of TCP Biotinyl-V-D-S-V-E-G-E-G-E-E-E-D-E-E-Y (SEQ ID NO: 13) in which the tyrosine (Y) is located at the end of the biotinylated peptide.

The enzyme, either TCP or TTL, is pre-incubated with compound during 15 min at room temperature. Then, the peptide substrate is added. Peptide was incubated at room temperature with different concentrations (10-100 μM) for TCP or TTL at a final concentration of 55 nM in a reaction volume of 50 μl (MES 50 mM; KCl 100 mM; MgCl2 25 mM; DTT 0.00 i M; ATP 0.0003M et L-Tyrosine 0.001M in 5% DMSO) during 30 min. After 30 min, reaction was stopped by the addition of TFA to a final concentration of 1%. The final volume was about 100 μl.

Reaction products were analyzed by RapidFire®/MS using the conditions described above The RapidFire®, 365 (Agilent Technology) high-throughput system (RF) was coupled to a G-6460 triple quadrupole mass spectrometer (Agilent) operated in electrospray negative-ion mode. A type C cartridge was used for sample trapping and elution. The RapidFire®-method employs a solid phase extraction (SPE) sample cleanup step directly coupled to MS detection.

Samples were aspirated for 600 ms, followed by 4000 ms loading and washing with mobile phase A of 98% ddH2O+2% ACN+TFA0.01% at a flow rate of 1.5 mL/min. A fixed loop of 40 μL samples was loaded onto the cartridge. Samples were then eluted for 500 ms with mobile phase B of 80% CAN+20% ddH2O+TFA 0.01% at a flow rate of 1.25 ml/min, followed by reequilibrating the cartridge with mobile phase A at 0.7 mL/min for 500 ms.

MS parameters: Gas Temp: 200; Drying Gas: 9; Nebulizer: 40; Sheath Gas Temp: 400; Seath Gas Flow: 12; VCap: 3500; Nozzle Voltage: 300; Delta EMV: 400

MRM transitions for tubulin peptide substrate and reaction products were m/z 858.3→669.5, m/z 939.8→719.8, respectively. The dwell time for each transition was 4 ms. Peak areas were integrated, and the areas under curves are converted into the amount of substrate remaining and the product formed using a substrate and reaction product calibration curve (see FIG. 19).

REFERENCES

Throughout this application, various references describe the state of the art to which this invention pertains. The disclosures of these references are hereby incorporated by reference into the present disclosure.

H. S. Barra, C. A. Arce, C. E. Argarana. Molecular neurobiology 2, 133 (Summer, 1988).

C. Erck et al., Proceedings of the National Academy of Sciences of the United States of America 102, 7853 (May 31, 2005).

A. C. Badin-Larcon et al., Proceedings of the National Academy of Sciences of the United States of America 101, 5577 (Apr. 13, 2004).

M. Barisic et al., Science (New York, N.Y. 348, 799 (May 15, 2015).

L Peris et al., The Journal of cell biology 174, 839 (Sep. 11, 2006).

P. Gobrecht et al., J Neurosci 36, 3890 (Apr. 6, 2016).

Y. Konishi, M. Setou, Nat Neurosci 12, 559 (May, 2009).
S. Marcos et al., PloS one 4, e5405 (2009).
J. P. Kerr et al., Nature communications 6, 8526 (Oct. 8, 2015).
P. Robison et al., Science (New York, N.Y. 352, aaf0659 (Apr. 22, 2016).
L. Lafanechere et al., Journal of cell science 111 (Pt 2), 171 (January, 1998).
R. A. Whipple et al., Cancer Res 70, 8127 (Oct. 15, 2010).
S. Belmadani, C. Pous. R. Ventura-Clapier, R. Fischmeister, P. F. Mery, Molecular and cellular biochemistry 237, 39 (August, 2002).
M. E. Hallak, J. A. Rodriguez, H. S. Barra, R. Caputto, FEBS Lett 73, 147 (Feb. 1, 1977).
A. Bosson et al., PloS one 7, e33490 (2012).
M. A. Child et al., Nat Chem Biol 9, 651 (October, 2013).
X. Fonrose et al., Cancer Res 67, 3371 (Apr. 1, 2007).
L, Sanchez-Pulido, C. P. Ponting, Bioinformatics 32, 1441 (May 15, 2016).
Y. Sato. Journal of biochemistry 153, 5 (January, 2013).
Y. Suzuki et al., Journal of cell science 123, 3094 (Sep. 15, 2010).
Y. Ditamo, Y. M. Dentesano, S. A. Purro, C. A. Arce, C. G. Bisig. Scientific reports 6, 38140 (Dec. 1, 2016).
G. G. Deanin, S. F. Preston, R. K. Hanson, M. W. Gordon, Eur J Biochem 109, 207 (August, 1980).
N. Kumar, M. Flavin. The Journal of biological chemistry 256, 7678 (Jul. 25, 1981).
A. Rovini et al., PloS one 8, e65694 (2013).
V. Redeker, Methods Cell Biol 95, 77 (2010).
S. Nimmagadda et al., Dev Dyn 236, 1358 (May, 2007).
T. Shibuya et al., Arteriosclerosis, thrombosis, and vascular biology 26, 1051 (May, 2006).
L. Paturle-Lafanechere et al., Journal of cell science 107 (Pt 6), 1529 (June, 1994).
D. R. Webster. G. G. Gundersen, J. C. Bulinski, G. G. Borisy, Proceedings of the National Academy of Sciences of the United States of America 84, 9040 (December 1987).
R. Norita et al., Cancer science 108,419 (March, 2017).
V. K. Khodiyar et al., Genomics 90, 285 (August 2007).
C. Aillaud et al., Molecular biology of the cell 27, 640 (Feb. 15, 2016).
K. Rogowski et al., Cell 143, 564 (Nov. 12, 2010).
S. Ramirez-Rios et al., Molecular biology of the cell 27, 2924 (Oct. 1, 2016).
C. E. Argarana, H. S. Barra, R. Caputto. Journal of neurochemistry 34, 114 (January, 1980).
J. Milbradt et al., Mol Cell Proteomics 13, 2132 (August, 2014).
J. D. Pedelacq, S. Cabantous, T. Tran, T. C. Terwilliger, G. S. Waldo, Nat Biotechnol 24, 79 (January, 2006).
I. Arganda-Carreras, R. Fernandez-Gonzalez, A. Munoz-Barrutia. C. Ortiz-De-Solorzano, Microsc Res Tech 73, 1019 (October 2010).
M. Barnat. J. Le Friec. C. Benstaali, S. Humbert, Neuron 93, 99 (Jan. 4, 2017).
J. J. Belanto, J. T. Olthoff. T. L. Mader, C. M. Chamberlain. D. M. Nelson, P. M. McCourt. D. M. Talsness, G. G. Gundersen, D. A. Lowe, J. M. Ervasti, Human Molecular Genetics 25, 45951 (2016).
C. Yingxian Chen, M. A. Caporizzo, K. Bedi, A. Vite, A. I. Bogush. P. Robison, J. G. Heffier, A. K. Salomon, N. A Kelly, A. Babu, M. P. Morley, K. B. Margulies, B. L. Prosser, Nature Medicine 24, 1225 (2018).
P. Robison, M. A. Caporizzo, H. Ahmadzadeh, A. I. Bogush, C. Yingxian Chen, K. B. Margulies, V. B. Shenoy, B. L. Prosser, Science 352, 428 (Apr. 22, 2016).
R. van den Berg, C. C. Hoogenraad, R. Q. Hintzen, Acta Neuropathology 134, 1 (2017).
J. Y. Li, L., Conforti, Experimental Neurology 246, 62 (2013).
S. Psilodimitrakopoulos, V. Petegnief, N. de Vera, O. Hernandez, D. Artigas, A. M. Planas. P. Loza-Alvarez, Biophysical Journal 104, 968 (March 2013).
X. Ma, W. Yang, X. Jiang, F. Li, X. Li, L. Ye, K. Liu, Neural Regeneration Research 5, 209 (February 2010).
D. Cartelli, G. Cappelletti, Molecular Neurobiology 54, 6762 (2017).
F. J. Baird, C. L. Bennett, Journal of Genetic Syndromes and Gene Therapy 4, 203 (Feb. 20, 2014).
J. Dubey, N. Ratnakaran, S. P. Koushika, Frontiers in Cellular Neuroscience 9, 343 (September 2015).
J. Eira, C. Santos Silva, M. Mendes Sousa, M. Almeida Liz, Progress in Neurobiology 141.61 (2016).
R. Brandt, L. Bakota, Journal of Neurochemistry 143, 409 (2017).
E. W. Dent, Molecular Biology of the Cell 28, 1 (January 2017).
S. S. Matsuyama, L. F. Jarkik, Proceedings of the National Academy of Sciences USA 86, 8152 (October 1989).
O. Blanquie, F. Bradke, Current Opinion in Neurobiology 51, 60 (2018).
W. Song, Y. Cho, D. Watt, V. Cavalli, The Journal of Biological Chemistry 290, 14765 (June 2015).
J. P. Kerr, P. Robison. G. Shi, A. I. Bogush, A. M. Kempema, J. K. Hexum, N. Becerra, D. A. Harki, S. S. Martin, R. Raiteri, B. L. Prosser, C. W. Ward, Nature Communications 6, 8526 (October 2015).
Aillaud, C., Bose, C., Peris, L, Bosson, A., Heemeryck, P., Van Dijk, J., Le Friec, J., Boulan, B., Vossier, F., Sanman, L. E., et al. (2017). Vasohibins/SVBP are tubulin carboxypeptidases (TCPs) that regulate neuron differentiation. Science (New York, N.Y. 358, 1448-1453.
Bosson, A., Soleilhac, J. M., Valiron, O., Job, D., Andrieux, A., and Moutin, M. J. (2012). Cap-Gly proteins at microtubule plus ends: is EB1 detyrosination involved? PloS one 7, e33490.
Frandemiche, M. L., De Seranno, S., Rush, T., Borel, E., Elie, A., Arnal, I., Lante, F., and Buisson, A. Activity-dependent tau protein translocation to excitatory synapse is disrupted by exposure to amyloid-beta oligomers. J Neurosci 34, 6084-6097.
Hsieh, H., Boehm, J., Sato, C., Iwatsubo, T., Tomita, T., Sisodia, S., and Malinow, R. (2006). AMPAR removal underlies Abeta-induced synaptic depression and dendritic spine loss. Neuron 52, 831-843.
Paturle-Lafanechere, L., Manier, M., Trigault, N., Pirollet, F., Mazarguil, H., and Job, D. (1994). Accumulation of delta 2-tubulin, a major tubulin variant that cannot be tyrosinated, in neuronal tissues and in stable microtubule assemblies. Journal of cell science 107 (Pt 6), 1529-1543.
Webland, J., and Willingham, M. C. (1983). A rat monoclonal antibody reacting specifically with the tyrosylated form of alpha-tubulin. II. Effects on cell movement, organization of microtubules, and intermediate filaments, and arrangement of Golgi elements. J Cell Biol 97, 1476-1490.

The invention claimed is:

1. A method for identifying inhibitors of tubulin carboxypeptidase (TCP) comprising the steps of:
   (i) incubating a candidate TCP inhibitor with a mouse or human vasohibin (VASH)/Small Vasohibin-Binding Protein (SVBP) complex, and the biotinylated peptide of sequence Biotinyl-V-D-S-V-E-G-E-G-E-E-E-D-E-E-Y (SEQ ID NO:13);
   (ii) quantifying, by Mass Spectrometry, the biotinylated peptide Biotinyl-V-D-S-V-E-G-E-G-E-E-E-D-E-E-Y (SEQ ID NO:13) and/or the biotinylated peptide Biotinyl-V-D-S-V-E-G-E-G-E-E-E-D-E-E (SEQ ID NO:12); present in the mixture obtained at the end of step (i); and
   (iii) determining whether the candidate TCP inhibitor is an inhibitor of VASH/SVBP complex activity from the results obtained in step (ii).

2. The method of claim 1, further comprising a step of isolating the biotinylated peptide(s) of Biotinyl-V-D-S-V-E-G-E-G-E-E-E-D-E-E (SEQ ID NO: 12) and/or Biotinyl-V-D-S-V-E-G-E-G-E-E-E-D-E-E-Y (SEQ ID NO: 13) after step (i) and before step (ii).

* * * * *

UNITED STATES PATENT AND TRADEMARK OFFICE
CERTIFICATE OF CORRECTION

PATENT NO. : 11,613,753 B2  
APPLICATION NO. : 16/758104  
DATED : March 28, 2023  
INVENTOR(S) : Annie Andrieux et al.

Page 1 of 1

It is certified that error appears in the above-identified patent and that said Letters Patent is hereby corrected as shown below:

On the Title Page

Column 1:  
Under "Assignees":  
The third Assignee should read: UNIVERSITE GRENOBLE ALPES, Saint Martin d'Hères (FR).  
The fourth Assignee should read: COMMISSARIAT A L'ENERGIE ATOMIQUE ET AUX ENERGIES ALTERNATIVES, Paris (FR).

Signed and Sealed this  
Twentieth Day of June, 2023

Katherine Kelly Vidal  
*Director of the United States Patent and Trademark Office*